United States Patent
Smith et al.

(10) Patent No.: US 6,282,264 B1
(45) Date of Patent: Aug. 28, 2001

(54) DIGITAL FLAT PANEL X-RAY DETECTOR POSITIONING IN DIAGNOSTIC RADIOLOGY

(75) Inventors: Andrew P. Smith, Medford; Jay A. Stein, Boston; Kevin E. Wilson, Cambridge; Richard E. Cabral, Tewksbury; Remo Rossi, Sterling, all of MA (US); James D. Miller, Perryville, MD (US)

(73) Assignee: Hologic, Inc., Bedford, MA (US)

( * ) Notice: Subject to any disclaimer, the term of this patent is extended or adjusted under 35 U.S.C. 154(b) by 0 days.

(21) Appl. No.: 09/449,457

(22) Filed: Nov. 25, 1999

Related U.S. Application Data

(63) Continuation-in-part of application No. 09/413,266, filed on Oct. 6, 1999, now abandoned.

(51) Int. Cl.[7] ............................................. G03B 42/04
(52) U.S. Cl. .......................... 378/189; 378/167; 378/177; 378/192
(58) Field of Search ...................... 378/167, 177, 378/181, 189, 192, 154, 98.8

(56) References Cited

U.S. PATENT DOCUMENTS

| | | | |
|---|---|---|---|
| 4,365,344 | 12/1982 | Dornheim | 378/189 |
| 4,468,803 | 8/1984 | Ronci | 378/181 |
| 4,741,014 | 4/1988 | Lajus | 378/189 |
| 4,807,272 | 2/1989 | Guenther et al. | 378/196 |
| 4,894,855 | * 1/1990 | Kresse | 378/196 |
| 4,905,265 | 2/1990 | Cox et al. | 378/98.8 |
| 5,023,899 | 6/1991 | Ohlson | 378/196 |
| 5,157,707 | 10/1992 | Ohlson | 378/181 |
| 5,319,206 | 6/1994 | Lee et al. | 250/370.09 |
| 5,434,418 | 7/1995 | Schick | 250/370.11 |
| 5,581,592 | * 12/1996 | Zarnoch et al. | 378/154 |
| 5,636,259 | 6/1997 | Khutoryansky et al. | 378/197 |
| 5,661,309 | 8/1997 | Jeromin et al. | 250/580 |
| 5,764,724 | 6/1998 | Ohlson | 378/177 |
| 5,818,898 | * 10/1998 | Tsukamoto et al. | 378/98.8 |
| 5,883,937 | 3/1999 | Schmitt | 378/189 |
| 5,920,606 | 7/1999 | Sohr | 378/177 |
| 6,152,598 | * 11/2000 | Tomisaki et al. | 378/209 |
| 6,155,713 | * 12/2000 | Watanabe | 378/197 |

FOREIGN PATENT DOCUMENTS 463237   10/1990   (SE) .

OTHER PUBLICATIONS

Sophisticated Raster Recording Technology also in the Lateral Path of Rays, "Diagnost 76" and informal English translation.

Reissue Application Serial No. 09/590,633, filed Jun. 8, 2000 and concurrently filed Request for Approval of Drawing Changes Pursuant to 37 CFR §1.174 and 37 CFR §1.121(b)(3).

Direct Radiography Corp. A Hologic Company "MultiDR General Rad System".

Fischerimaging "Digital Traumex".

ddRMulti-System "Swissray".

Merrills's Atlas of Radiographic Positions and Radiologic Procedures, vol. 2, Ballinger P.W. and Frank E.D., pp. 42, 44, 174, 184, 256, 333, 346, 368, 392, 398, 410 and 431.

* cited by examiner

*Primary Examiner*—Robert H. Kim
*Assistant Examiner*—Allen C. Ho
(74) *Attorney, Agent, or Firm*—Cooper & Dunham LLP

(57) ABSTRACT

A digital, flat panel, two-dimensional x-ray detector moves reliably, safely and conveniently to a variety of positions for different x-ray protocols for a standing, sitting or recumbent patient. The system makes it practical to use the same detector for a number or protocols that otherwise may require different equipment, and takes advantage of desirable characteristics of flat panel digital detectors while alleviating the effects of less desirable characteristics such as high cost, weight and fragility of such detectors.

50 Claims, 47 Drawing Sheets

PEDESTAL WITH CANTILEVERED TABLE;
HORIZONTAL SID APPLICATIONS

PEDESTAL WITH CANTILEVERED TABLE;
VERTICAL SID APPLICATIONS

PEDESTAL WITH CANTILEVERED TABLE;
CROSS-TABLE LATERAL APPLICATIONS

PEDESTAL WITH CANTILEVERED TABLE;
HORIZONTAL SID WHEELCHAIR APPLICATIONS

PEDESTAL WITH CANTILEVERED TABLE;
CROSS-TABLE LATERAL APPLICATIONS

PEDESTAL WITH CANTILEVERED TABLE;
CHEST APPLICATIONS

PEDESTAL WITH CANTILEVERED TABLE;
IN-TABLE APPLICATIONS

PEDESTAL WITH CANTILEVERED MOBILE TABLE;
CROSS-TABLE LATERAL APPLICATIONS

PEDESTAL WITH CANTILEVERED MOBILE TABLE;
CHEST APPLICATIONS

PEDESTAL WITH CANTILEVERED MOBILE TABLE;
IN-TABLE APPLICATIONS

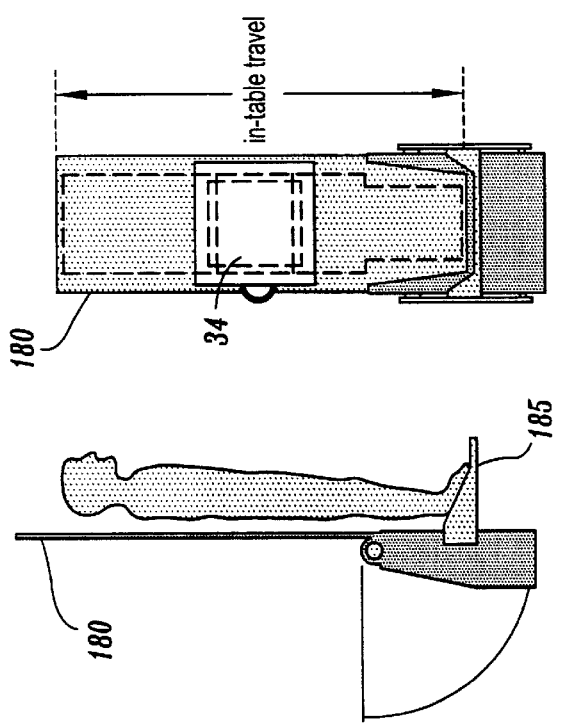
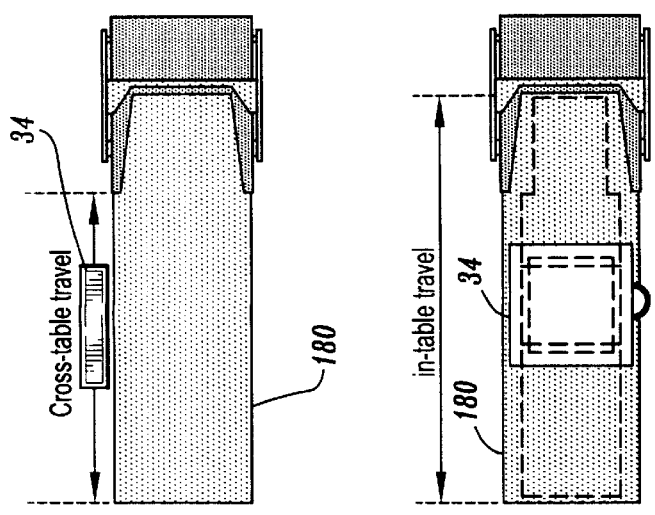
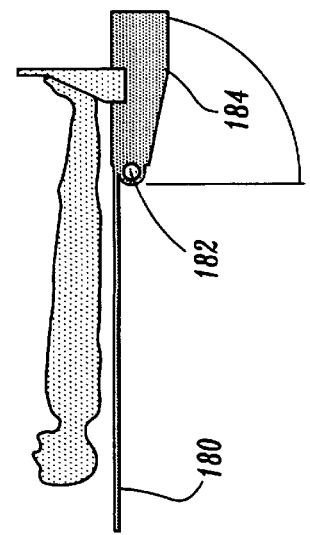
FIG. 50
FIG. 49
FIG. 46
FIG. 47
FIG. 48

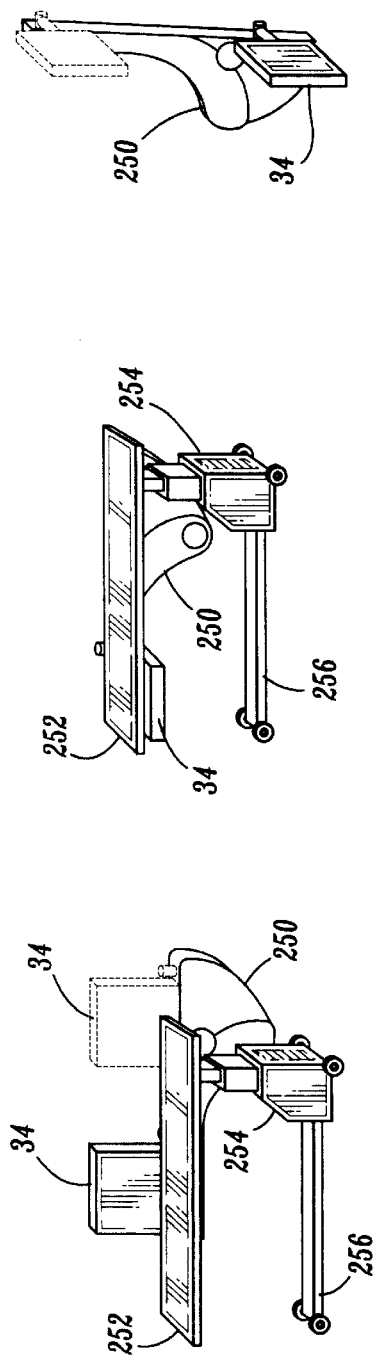
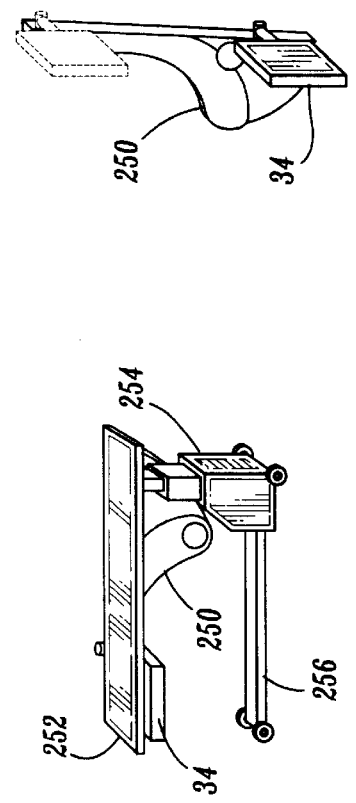
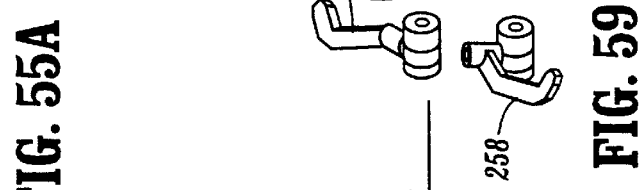
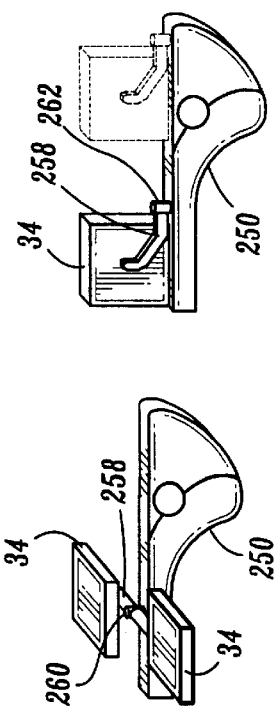
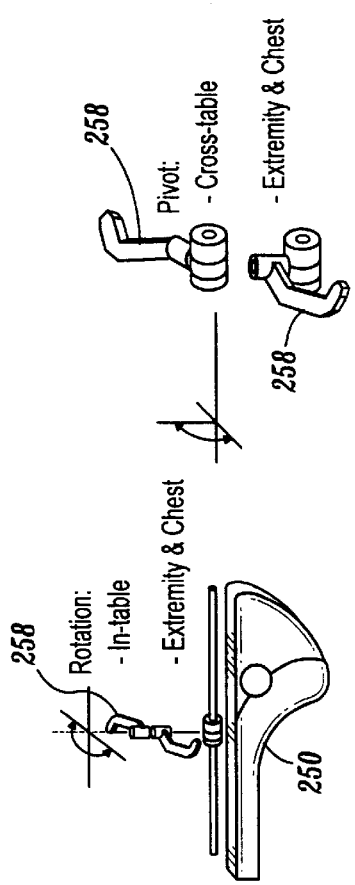
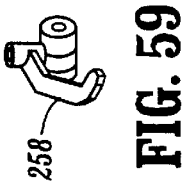

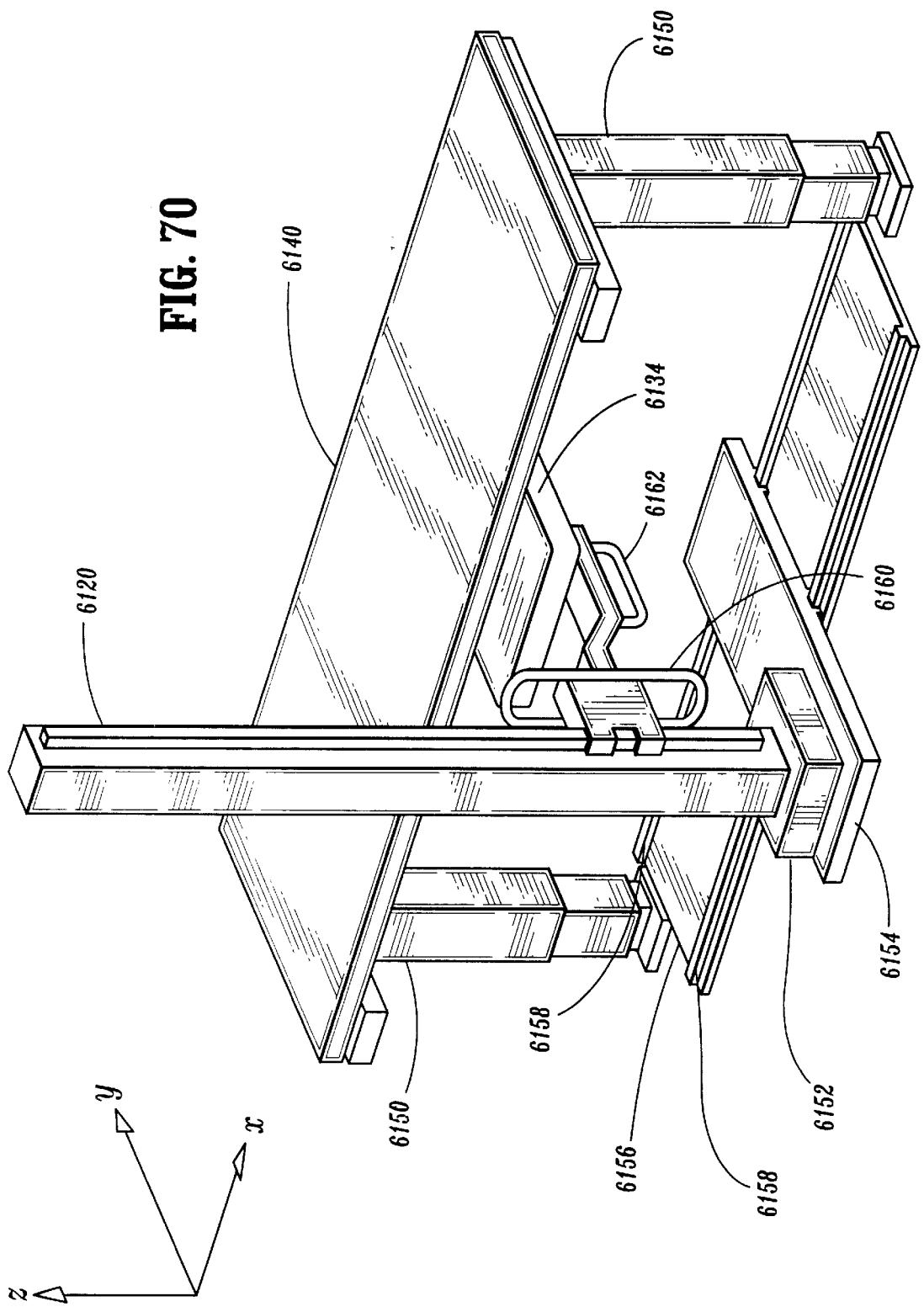

DIGITAL FLAT PANEL X-RAY DETECTOR POSITIONING IN DIAGNOSTIC RADIOLOGY

REFERENCE TO RELATED APPLICATION

This application is a continuation-in-part of parent application Ser. No. 09/413,266 filed on Oct. 6, 1999, allowed on Dec. 1, 2000 and now expressly included in (and abandoned in favor of) this patent application.

FIELD

This patent specification is in the field of radiography and pertains more specifically to the field of x-ray equipment using a digital flat panel detector.

BACKGROUND

Medical diagnostic x-ray equipment has long used x-ray film contained inside a lightproof cassette, with the cassette at one side of the patient and an x-ray source at the opposite side. During exposure, x-rays penetrate the desired body location and the x-ray film records the spatially varying x-ray exposure at the film. Over the years, medical experience has developed and optimized a variety of standard protocols for imaging various parts of the body, which require placing the film cassette in different positions relative to the patient. Chest x-rays, for example, are often performed with the patient standing, chest or back pressed against a vertical film cassette. Imaging of the bones in the hand might be done with the cassette placed horizontally on a surface, and the hand placed on top of the cassette. In another procedure the patient might cradle the cassette under an arm. A collection of such standard protocols is described in Merrill's Atlas of Radiographic Positions and Radiologic Procedures, by Philip W. Ballinger, et.al., 9th edition, published by Mosby-Year Book, Incorporated, hereby incorporated by reference.

Advances in digital x-ray sensor technology have resulted in the development of arrays of sensors that generate electrical signals related to local x-ray exposure, eliminating film as the recording medium. An example is discussed in U.S. Pat. No. 5,319,206, incorporated herein by reference, and a current version has been commercially available from the assignee of this patent specification. Such digital arrays are often called flat panel x-ray detectors, or simply flat panel detectors, and offer certain advantages relative to x-ray film. There is no need for film processing, as the image is created and comes from the cassette in electronic digital form, and can be transferred directly into a computer. The digital format of the x-ray data facilitates incorporating the image into a hospital's archiving system. The digital flat panel detectors or plates also offer improved dynamic range relative to x-ray film, and can thus overcome the exposure range limitations of x-ray film that can necessitate multiple images to be taken of the same anatomy. On the other hand, digital flat panel detectors currently have a higher capital cost than film cassettes, and are more fragile. They often incorporate lead shielding to protect radiation-sensitive electronics, and can be heavy. If they are connected to a computer with a cable, cable handling needs to be taken into consideration when moving the cassette and/or the patient. Alternatively, the cassette can be self-contained, as for example in U.S. Pat. No. 5,661,309, in which case it includes a power supply and storage for the image information, increasing its weight and possibly size. Such detectors commonly are used in a system comprising a suitable anti-scatter or Bucky plate.

The high initial cost of the digital detector can hinder outfitting of an x-ray room with multiple detectors premounted in a variety of positions, such as a vertically-mounted unit for chest, and a horizontal unit under a bed. The fragility, weight, and initial cost of the units make them difficult to use in procedures where the patient cradles the detector. The unique characteristics of digital flat panel detectors can make conventional film cassette holders impractical for use with flat panel detectors.

A number of proposals have been made for x-ray systems using flat panel detectors. A C-arm arrangement has been offered under the name Traumex by Fisher Imaging Corporation of Denver, Colo., with the participation of a subsidiary of the assignee hereof. Another C-arm arrangement is believed to be offered under the name ddRMulti-System by Swissray, and literature from Swissray has stated that a ddRCombi-System is scheduled for launch in early 2000 and would offer the same functionality as the ddRMulti-System but would use existing third party suspension equipment for the x-ray tube (an illustration therein appears to illustrate a detector arrangement mounted for vertical movement on a structure separate from a ceiling-mounted x-ray tube support. A vertically moving and rotating image intensifier appears to be illustrated in FIG. 3 of U.S. Pat. No 4,741,014. U.S. Pat. No. 5,764,724 proposes yet another a patient table and can be moved to a number of position along the table edge.

A number of other proposals have been made for positioning x-ray film cassettes but the different physical characteristics and requirements of flat panel detectors systems do not allow for direct application of film cassette positioning proposals. For example, U.S. Pat. No. 4,365,344 proposes a system for placing a film cassette in a variety of positions and orientations relative to a floor mounted x-ray source support. U.S. Pat. No. 5,157,707 proposes moving a film cassette to different positions relative to a ceiling mounted x-ray tube support to allow taking AP (anterior-posterior) and lateral chest images of a patient sitting on a bed. The figures of Swedish patent document (Utlaggningsskrif [B]) 463237 (application 8900580-5) appear to show a similar proposal as well as a proposal to mount the x-ray cassette and the x-ray source on the same structure extending up from the floor. U.S. Pat. No. 4,468,803 proposes clamping an articulated support for a film cassette on a patient table, and U.S. Pat. No. 5,920,606 proposes a platform on which a patient can step and into which a film cassette can be inserted to image a weight-bearing foot.

With a view to the unique characteristics and requirements of digital flat panel detector systems, it is believed that a need exists to provide a safe, reliable, convenient and effective way to position such systems for a wide variety of imaging protocols, and this patent specification is directed to meeting such a need.

SUMMARY

An exemplary and non-limiting embodiment comprises a digital, flat panel, two-dimensional x-ray detector system that is not mechanically coupled to x-ray source motion and can safely and conveniently move to any one of a wide variety of positions for standard or other x-ray protocols and can securely maintain the selected position to take x-ray images, thus making it possible to use a standard x-ray source in an x-ray room, such as a ceiling-mounted source, with a single digital flat panel detector for x-ray protocols that might otherwise require plural detectors.

One preferred embodiment, described by way of an example and not a limitation on the scope of the invention set forth in the appended claims, comprises a detector that is free of a mechanical connection with an x-ray source and includes a digital flat panel x-ray detector arrangement and an anti-scatter grid. A floor-supported base supports an articulated structure that in turn supports and selectively moves the detector with at least five degrees of freedom to position it for any one of a variety of standard or other diagnostic x-ray protocols for standing, sitting, and recumbent patients. In a non-limiting example, the degrees of freedom include at least two translational and three rotational motions. For example, a first translational motion comprises moving a lower slide along the base, a first rotational motion comprises rotating about a vertical axis a lower arm having a near end mounted on the lower slide, a second rotational motion comprises rotating about another vertical axis a column mounted at a far end of the lower arm, a second translational motion comprises moving an upper slide up and down the column, and a third rotational motion comprises rotating about a horizontal axis an upper arm having a near end mounted on the upper slide and a far end coupled to the detector. In addition, the detector can be rotationally mounted on the far end of the upper arm to rotate about an axis transverse to its face, for a sixth degree of freedom. The detector can also be rocked, i.e. rotated about a vertical axis when vertically oriented, to provide angulation for cross-table oblique imaging, as is commonly done for the axiolateral projection of the hip. The more general case is that the detector can be rotated about and axis extending along or generally parallel to its viewing surface.

For certain x-ray protocols, it can be desirable to couple vertical motion of the detector to vertical motion of a patient table, and such provisions are included in the disclosed system. To make moving and positioning the detector easier, motion in at least some of the degrees of freedom is regulated with detents that bias the motion to preferred steps and can lock to prevent undesired motion. The motion in one or more degrees of freedom can be motorized. Further, the motion in some or all of the degrees of freedom can be computer-controlled. A collision avoidance system can be provided to help prevent pinch-points and collisions for the motions in one or more of the degrees of freedom. Encoders coupled with moving parts can provide digital information regarding motion and position, and the information can be used by a programmed computer to control the motions in various ways. For example, the information can be used in pinch-point and collision avoidance and/or in computer-controlling motions that position the detector at selected positions and orientations.

The disclosed system can be used with a patient table on a pedestal that drives the table up and down and can move the table along its length and, additionally, can pivot the table about a horizontal and/or vertical axis to allow for a greater variety of x-ray protocols. The system can be used without a table, for example for x-ray protocols involving a standing patient or a patient on a bed or gurney or wheelchair. The detector can have a rectangular imaging area, in which case provisions can be made for rotating the detector between landscape and portrait orientations, and further provisions can be made for automatically detecting the orientation, such as by providing exposure sensors that also serve to provide orientation information. The detector can be made with a square imaging area, in which case it need not rotate between landscape and portrait orientation, but rotation can still be provided, for example to image a limb or some other structure along the diagonal of the imaging area, or alternatively to align the anti-scatter grid in a desired orientation. A variant of the disclosed system can be made for use with a step stool for imaging weight-bearing extremities, where the detector moves with at least two degrees of freedom between a horizontal orientation under a stool portion on which the patient stands and a vertical orientation alongside that portion of the stool. Another variant can be directed to x-ray protocols that do not involve the upper body of a standing patient.

BRIEF DESCRIPTION OF THE DRAWINGS

FIGS. 42–49 illustrate another embodiment.

FIGS. 46–50 illustrate yet another embodiment.

FIGS. 54–59 illustrate another embodiment.

FIG. 70 illustrates the embodiments of FIG. 69, with the detector in another position.

DETAILED DESCRIPTION OF PREFERRED EMBODIMENTS

Figure 1:
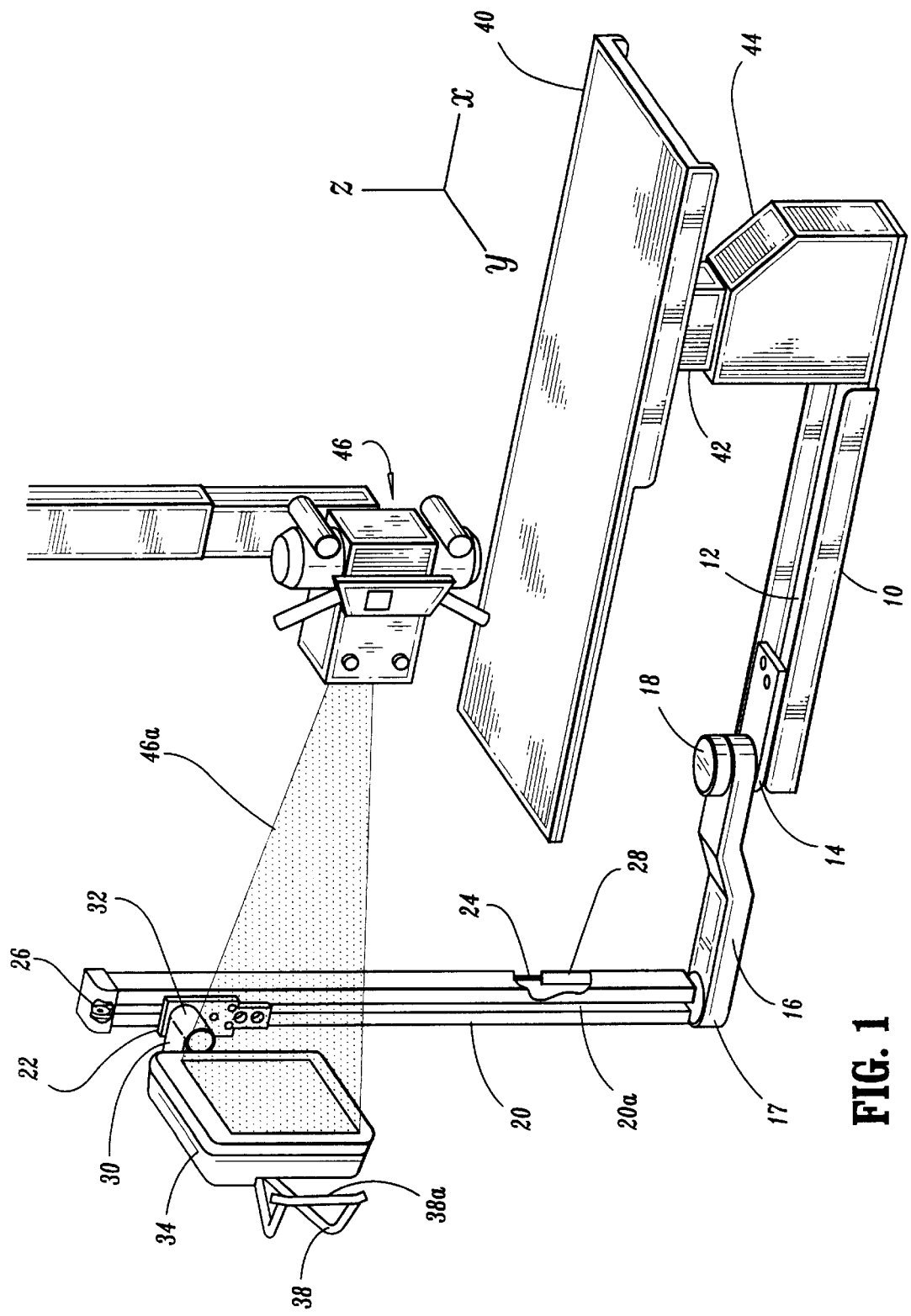
FIG. 1 illustrates a digital flat panel detector in a vertical orientation, for example for a chest-x-ray of a standing patient, using a ceiling-mounted x-ray source.

Referring to FIG. 1, a main support 10 can be secured to the floor of an x-ray room (or to a movable platform, not shown), and has a track 12 on which a lower slide 14 rides for movement along an x-axis. Slide 14 supports the proximal or near end of a generally horizontal lower arm 16 through a bearing at 18 allowing rotation of arm 16 about an upwardly extending axis, e.g., a z-axis. The distal or far end of lower arm 16 in turn supports an upwardly extending, e.g., vertical, column 20, mounted for rotation about an upwardly extending, e.g, vertical, axis though a bearing at 17. Column 20 has a slot 20a along its length. An upper slide 22 engages slot 20a to ride along the length of column 20 and is supported by a cable or chain system 24 that reverse direction over pulleys 26 at the top and bottom of column 20 (only the top pulley is illustrated) and connect to counterweights 28 riding inside column 20. Upper slide 22 in turn supports an upper arm 30 through a bearing arrangement at 32 allowing rotation of upper arm 30 about a lateral, e.g., horizontal, axis extending along the length of upper arm 30. Preferably, the bearing arrangement is situated along the center of mass of the detector system, which offers a safety feature in case of an accidental brake or detent release that could turn the detector against the patient. Upper arm 30 supports an x-ray detector 34 containing a two-dimensional digital flat panel detector array, for example of the type discussed in the U.S. patents cited above, and typically also containing an anti-scatter grid and electronics for receiving control and other signals and sending out digital image and other information through cables (not shown) and/or in a different way. Detector 34 can be connected to upper arm 30 through a bearing arrangement at 36 (FIG. 7) to allow rotation of detector 34 about an axis normal to the x-ray receiving face of the flat panel detector. This can be desirable if the imaging area of detector 34 is rectangular, to allow using it in portrait or landscape orientations, or if such rotation is desirable for other reasons, for example to align the detector diagonal with a patient's limb or other anatomy of interest. Alternatively, the bearing arrangement at 36 can be omitted. A handle 38 is attached to detector 34, for example when a bearing at 36 is used, or can be attached directly to upper arm 30 otherwise, and has a manual switches or other controls at 38a for control purposes, such as to lock and unlock various motions and/or to control motorized movements.

A patient table 40 is supported on a telescoping column 42 that moves table 40 up and down, e.g., along the z-axis, within a guide 44 that can be floor-mounted, or mounted on a movable support, and may or may not be secured to main support 10. Table 40 is made of a material that minimizes distortion of the spatial distribution of x-rays passing through it. If desired, table 40 can be made movable along the x-axis, in a manner similar to the bed in the QDR-4500 Acclaim system commercially available from the assignee of this patent specification, and/or can be made to tilt about one or more lateral axis, e.g., the x-axis and the y-axis, and/or rotate about an upwardly extending axis, e.g., the z-axis. A console and display unit 41 (FIG. 9) can be connected by cable or otherwise to detector 34 to supply power and control signals thereto and to receive digital image data therefrom (and possibly other information) for processing and display. The display at unit 41 can be, for example, on a CRT or a flat panel display screen used in the usual manner and image and other information can be suitably archived and/or printed as is known in the art. The usual image manipulation facilities can be provided at unit 41, for example for level and window controls of the displayed digital x-ray image, for image magnification, zoom, cropping, annotation, etc. The cabling can be run through upper arm 30, column 20, and lower arm 16 to avoid interference with motion of the articulated support structure between main support 10 and detector 34. Alternatively, detector 34 can be powered and controlled in some other way, and image data can be extracted therefrom in some other way. For example, detector 34 can be a self-contained detector, with an internal power supply and with control switches on or in detector 34 to control its operation. Detector 34 can further contain storage for the data of one or more x-ray images. Image data can be taken out of detector 34 by way of a wireless connection, or by temporarily plugging in a cable therein when it is time to read image data, or in some other way. Detector 34 can include one or more exposure sensors (not illustrated) such as ion chambers used as is known in the art to control x-ray exposure. By arranging five exposure sensors around detector 34 such that three would be along the top of the detector for a chest x-ray in either orientation of detector 34, and providing a microswitch or some other sensor (not shown) to detect the orientation of detector 34 and provide a signal directing the use of the three exposure sensors that at along the top of detector 34 at the time.

Detector 34 typically is used with a ceiling-suspended x-ray source 46 of the type commonly present in x-ray rooms. Such x-ray sources typically are suspended through telescoping arrangements that allow the source to be moved vertically and rotated about an axis so the x-ray beam, illustrated schematically at 46a, can be aligned with an x-ray receptor such as a film cassette and, in the case of using the system disclosed herein, a digital flat panel detector. A translational motion of source 46 may also be possible. Such x-ray sources typically have an optical arrangement beaming light that indicates where the collimated x-ray beam will strike when the x-ray tube is energized, and have appropriate controls for beam collimation and x-ray technique factors.

The first embodiment disclosed herein employs five degrees of freedom for motion of detector 34, and a sixth degree as well if desired to rotate detector 34 about an axis transverse to its plane. Detector 34 is free of mechanical connection to motions of x-ray source 46, so all motions of detector 34 are independent of the position or motions of the x-ray source. Further, detector 34 is free of a mechanical connection with table 40, so all motions of detector 34 are independent of the positions or motions of the patient table. However, as explained below, provisions can be made to selectively couple up and down movements of detector 34 and table 40 for certain procedures, and provisions can be made for collision avoidance between the detector 34 and its support structure with table 40 and/or x-ray source 46.

Figure 7:
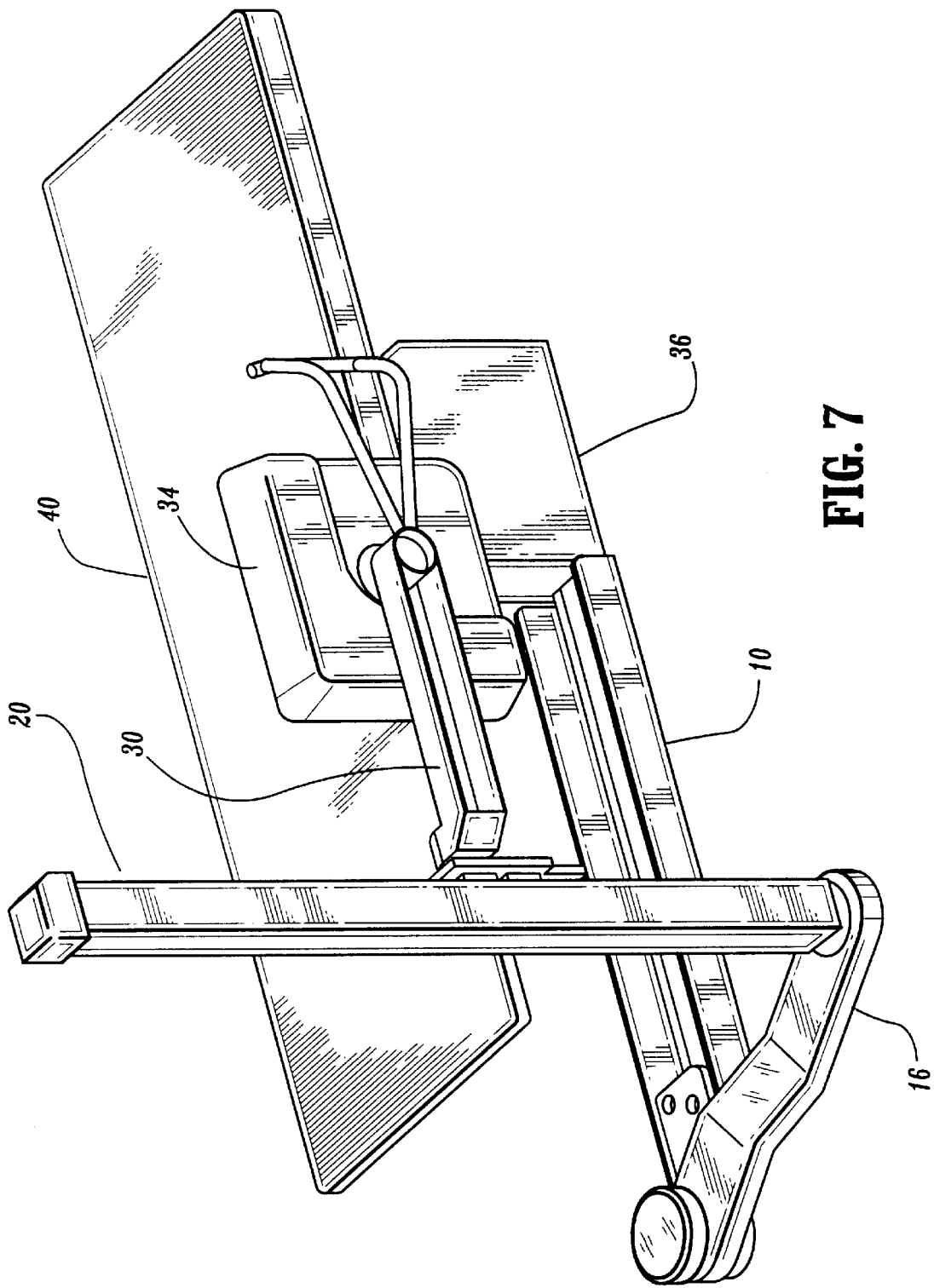
FIG. 7 is a similar illustration, showing the detector in a vertical orientation next to a side of the patient table and parallel thereto.

A first degree of freedom for detector 34 relates to translational motion of slide 14 along main support 10. A second related to rotation of lower arm 16 about the bearing at 18. A third relates to rotation of column 20 about the bearing at 17. A fourth relates to up/down motion of upper slide 22 along column 20. A fifth relates to rotation of upper arm 30 about the bearing at 32. A sixth degree of freedom, if desired, relates to rotation of detector 34 about the bearing at 36 (FIG. 7).

Through a combination of translating lower slide 14 along base 10 and rotating lower arm 16 about the bearing at 18, detector 34 moves along and across the length of table 40 as desired. The height of detector 34 is adjusted by moving slide 22 up or down column 20. The orientation of detector 34 is adjusted through rotation about the bearing at 32 and, if provided for and desired, through rotation about the bearing at 36. Rotation of column 20 about the bearing at 17 further helps position and orient detector 34.

Patient table 40 and its supporting structure 42 and 44 need not be used at all for many x-ray protocols and can be omitted altogether from embodiments of the disclosed system in which detector 34 and its articulated support structure are otherwise the same as illustrated in FIGS. 1–9, 11 and 12. As earlier noted, the embodiment illustrated in FIG. 10 does not use a patient table. Patient table 40 can be mounted for rotation about column 42 through a suitable bearing arrangement (not illustrated), for example though an angle of 90° or more, if desired to move it out of the way for certain x-ray procedures, or because of the configuration of the x-ray room or for other reasons. In addition, or alternatively, table 40 can be mounted for pivoting about a y-axis, for example an axis at the top of column 42, and/or can be mounted for pivoting about an x-axis, for example at the top of column 42. The table 40 could also be mounted for pivoting about a vertical z-axis. The pivoting can be through any desired angle the mechanical arrangement permits. Of course, suitable arrangements for locking table 40 in position can be made.

In the position of detector 34 illustrated in FIG. 1, the x-ray protocol can be a chest x-ray of a standing patient. For this protocol, slide 14 moves to the left in the drawing, lower arm 16 rotates to point away from base 10, column 20 rotates to point upper arm normal to base 10 and lower arm 16, and upper arm 30 rotates to orient detector 34 vertically, facing x-ray source 46 that has been, or is, moved to a suitable position so that its optical arrangement shows proper alignment with detector 34. The vertical position of detector 34 is adjusted by sliding upper slide 22 along column 20. If detector 34 has portrait and landscape orientation, it is rotated to the desired orientation, and an x-ray exposure is taken after setting the x-ray technique factors and positioning a patient as is known in the art. In an embodiment employing manual movement, the operator pushes appropriate buttons 38a on handle 38 to release the articulated structure between detector 34 and base 10 for the appropriate movement, and pushes or releases appropriate buttons at the end of the movement to lock the structure in place for the x-ray procedure. A single button or other operator interface can be used to release all parts of the articulated structure for movement and to lock them for an x-ray procedure, or respective buttons of other interface devices can be used for individual movements of combinations of less than all movements. If some or all of the movements are motorized, the operator uses suitable buttons or other controls to unlock the movements and direct the motorized motions and then lock the articulated structure in position.

If greater distance between detector 34 and table 40 is desired, lower arm 16 is rotated to be transverse to base 10, e.g., perpendicular to base 10, and column 20 is rotated to keep upper arm 30 pointing as shown in FIG. 1. In addition, table 40 can be moved all the way to the right in FIG. 1 along is permitted x-axis motion, and/or can be rotated or tilted as earlier described.

Figure 2:
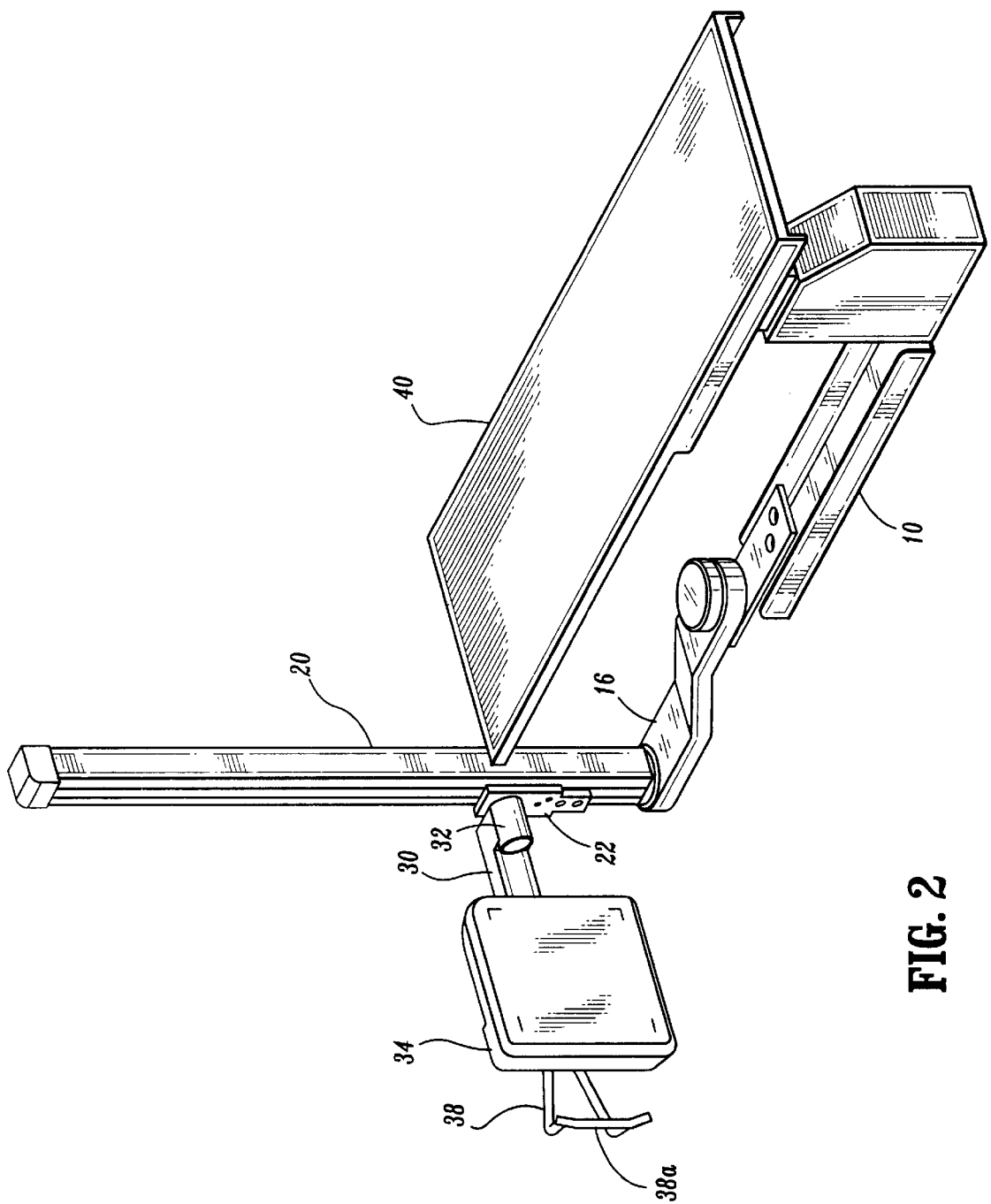
FIG. 2 is a similar illustration, showing the detector at a lower position, for example for imaging the legs of a standing patient or for a chest x-ray of a patient on a wheelchair, a gurney or some other support.

The position illustrated in FIG. 2 can be used for a protocol such as imaging the leg or legs of a standing patient, or imaging a patient on a wheelchair or a gurney. It is similar to the position FIG. 1 illustrates, and detector 34 can be moved thereto similarly, except to a lower vertical position. Again, if greater distance from the side of table 40 is desired, lower arm 16 can be angled transverse to the length of base 10. X-ray source 46 is not shown in FIG. 2 but is in a position to direct the x-ray beam at detector 34 through the patient.

Figure 3:
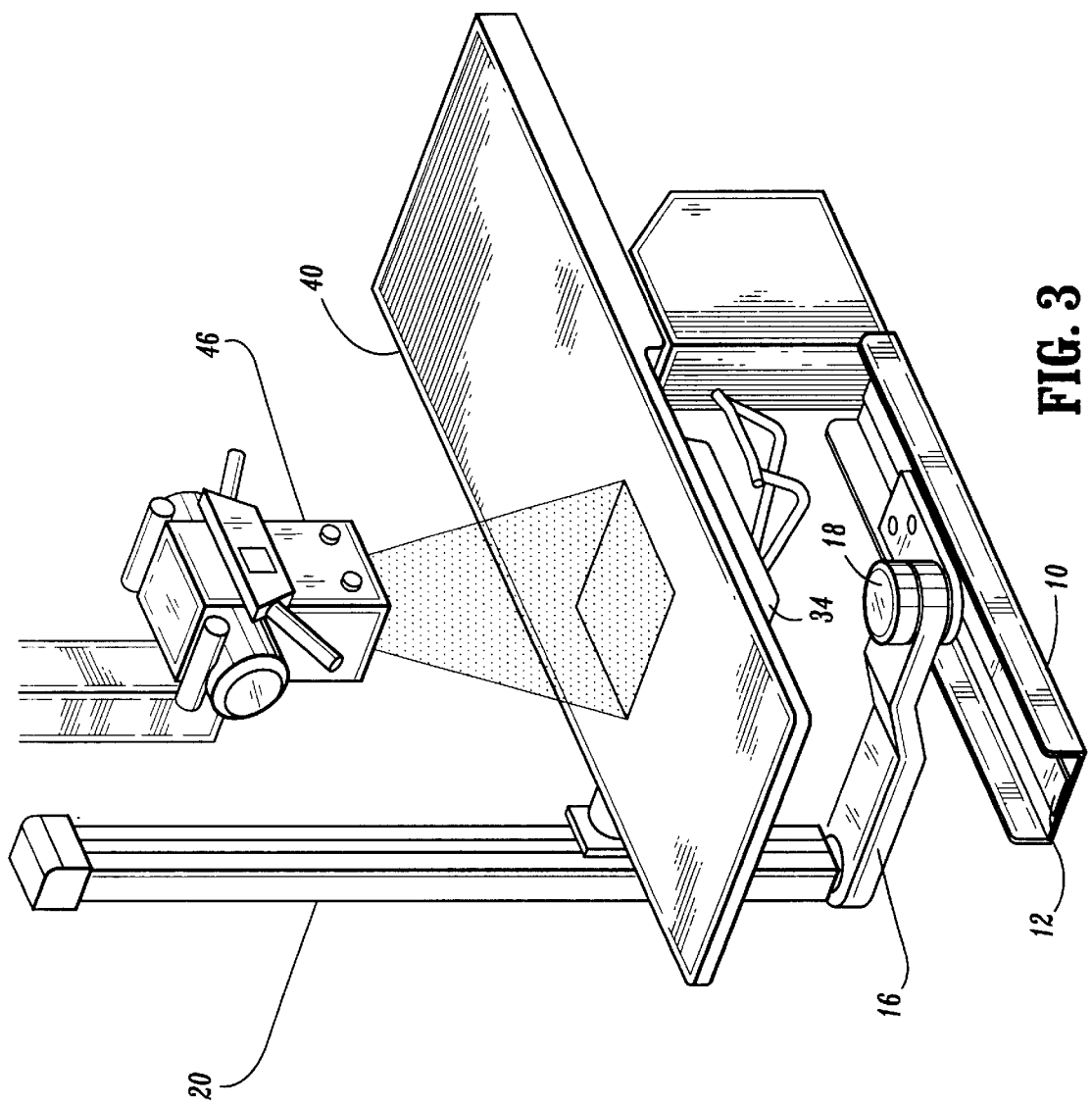
FIG. 3 is a similar illustration, showing the detector in a horizontal orientation under a patient table.

FIG. 3 illustrates a position suitable for example for a chest AP image of a recumbent patient, e.g., in the supine position on table 40. Table 40 can be lowered to make it easier for the patient to get on and then raised if desired. For this x-ray protocol, detector 34 is moved to a horizontal orientation below patient table 40 by moving the articulated support structure as earlier described. If desired, detector 34 and table 40 can be interlocked when in the illustrated positions, to thereafter move up or down as a unit. The interlock can be mechanical, by a clamp or pin (not shown) in case upper slide 30 is moved manually along column 20, so that detector 34 would be driven vertically by motorized vertical motion of table 40. If slide 30 is motorized, the vertical motion of slide 30 and table 40 can be synchronized through known electronic controls. Table 40 is moved all the way to the left as seen in FIG. 3 in this example.

Figure 4:
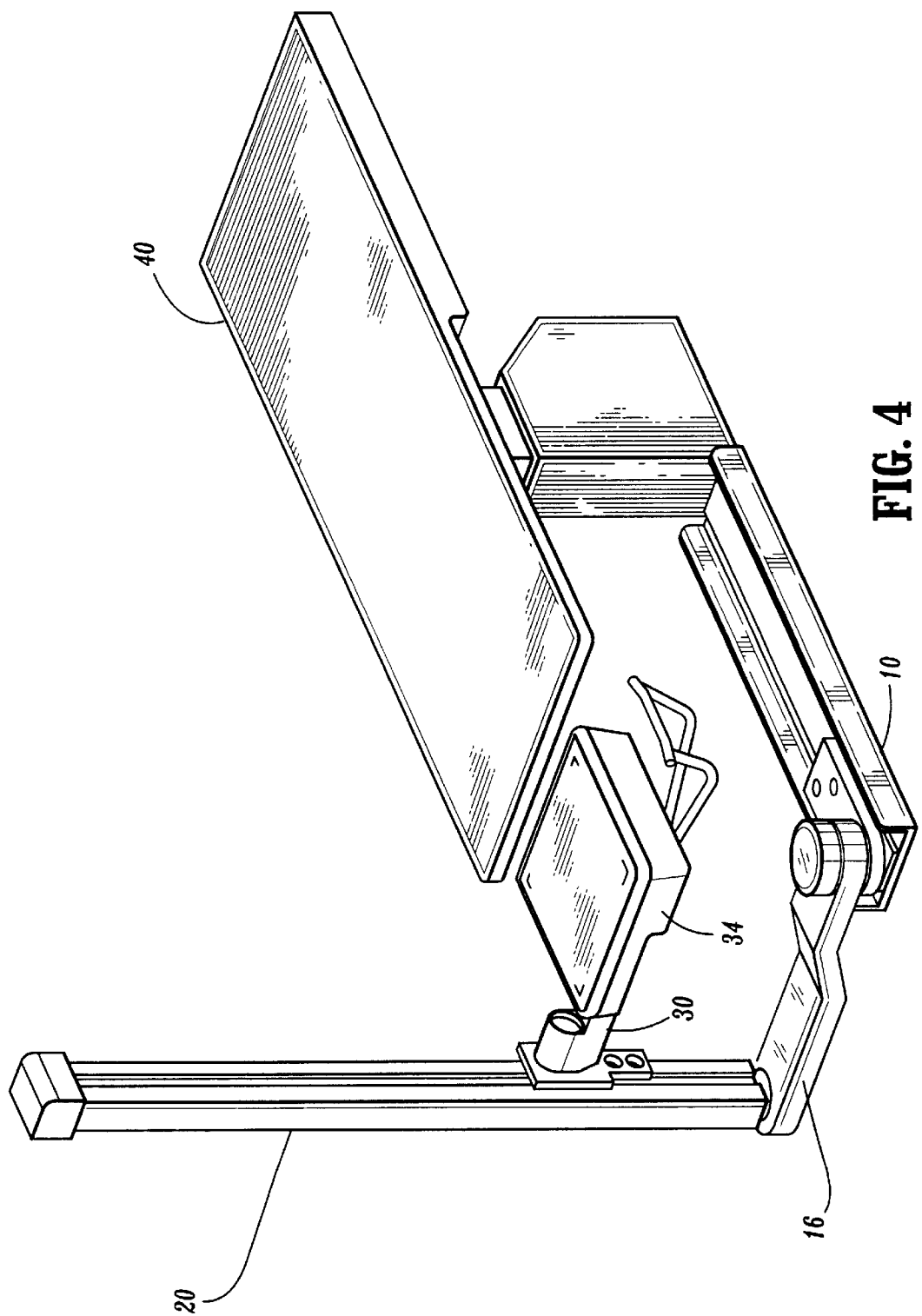
FIG. 4 is a similar illustration, showing the detector in a horizontal orientation, next to the head of foot of the patient table and at the same level, for example for imaging a patient's extremity.

FIG. 4 illustrates a position in which detector 34 is also in a horizontal orientation and faces up, but is at the head or foot of table 40 and substantially coplanar therewith. X-ray protocols such as imaging a limb or the head of a patient recumbent on table 40 can be carried out in this position of detector 34 and table 40. Table 40 is moved to the right as seen in FIG. 4 in this example. X-ray source 46 is not shown in FIG. 4 but would be above detector 34.

Figure 5:
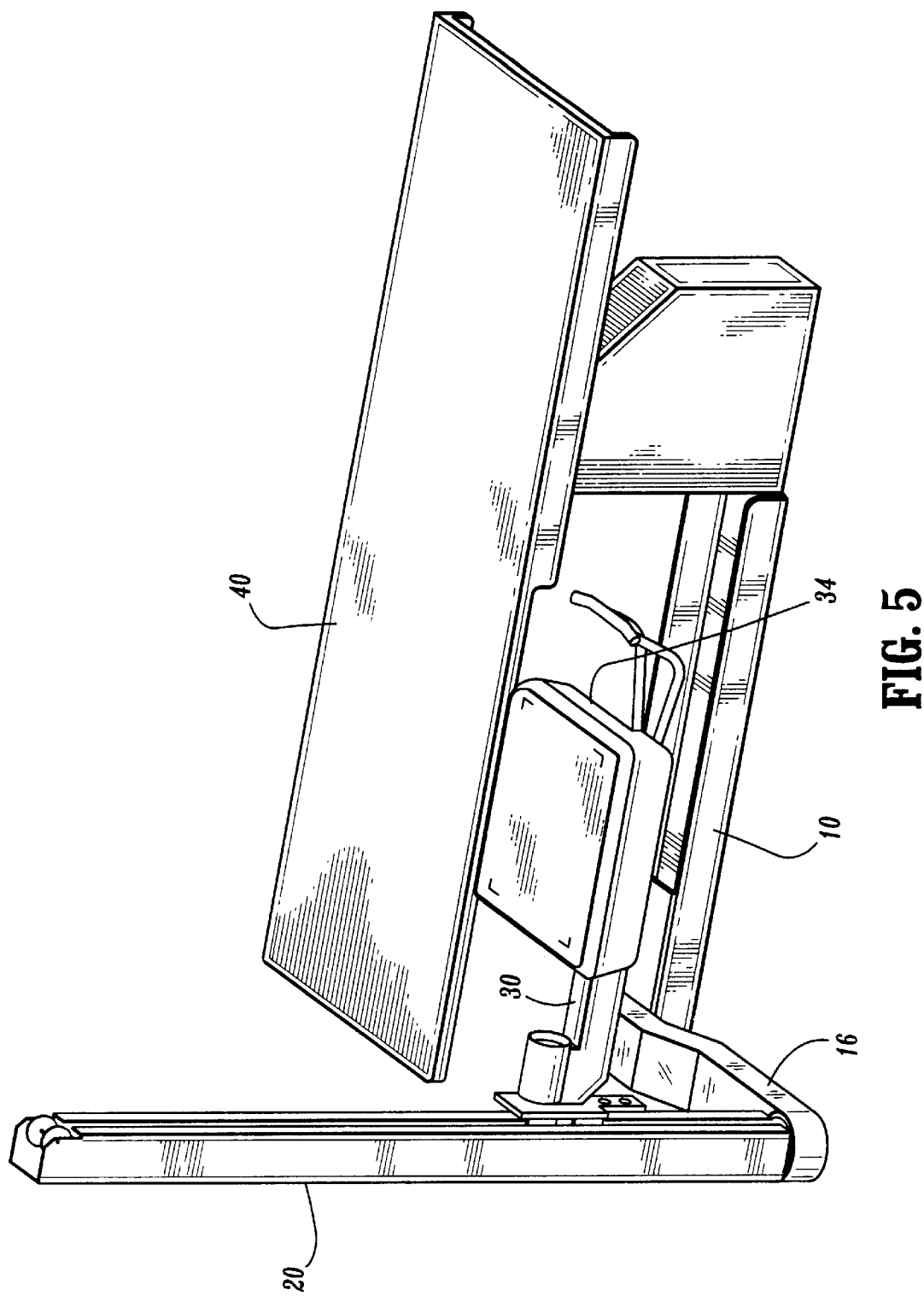
FIG. 5 is a similar illustration, showing the detector in a similar horizontal orientation but next to a side of the patient table, for example for imaging a patient's arm or hand.

FIG. 5 illustrates a position of detector 34 and table 40 suitable for x-ray protocols such as imaging an arm or a hand of a patient recumbent on table 40. For this protocol, detector 34 is moved to one side of table 40, in a horizontal orientation and facing up. Detector 34 can be coplanar with table 40 or can be vertically offset therefrom by a selected distance. The disclosed system allows detector 34 to be moved to either side of table 40 and to be at any one of a number of positions along a side of table 40 and to be spaced from table 40 both laterally and vertically by selected distances. X-ray source 46 is not shown in FIG. 5 but would be above detector 34.

Figure 6:
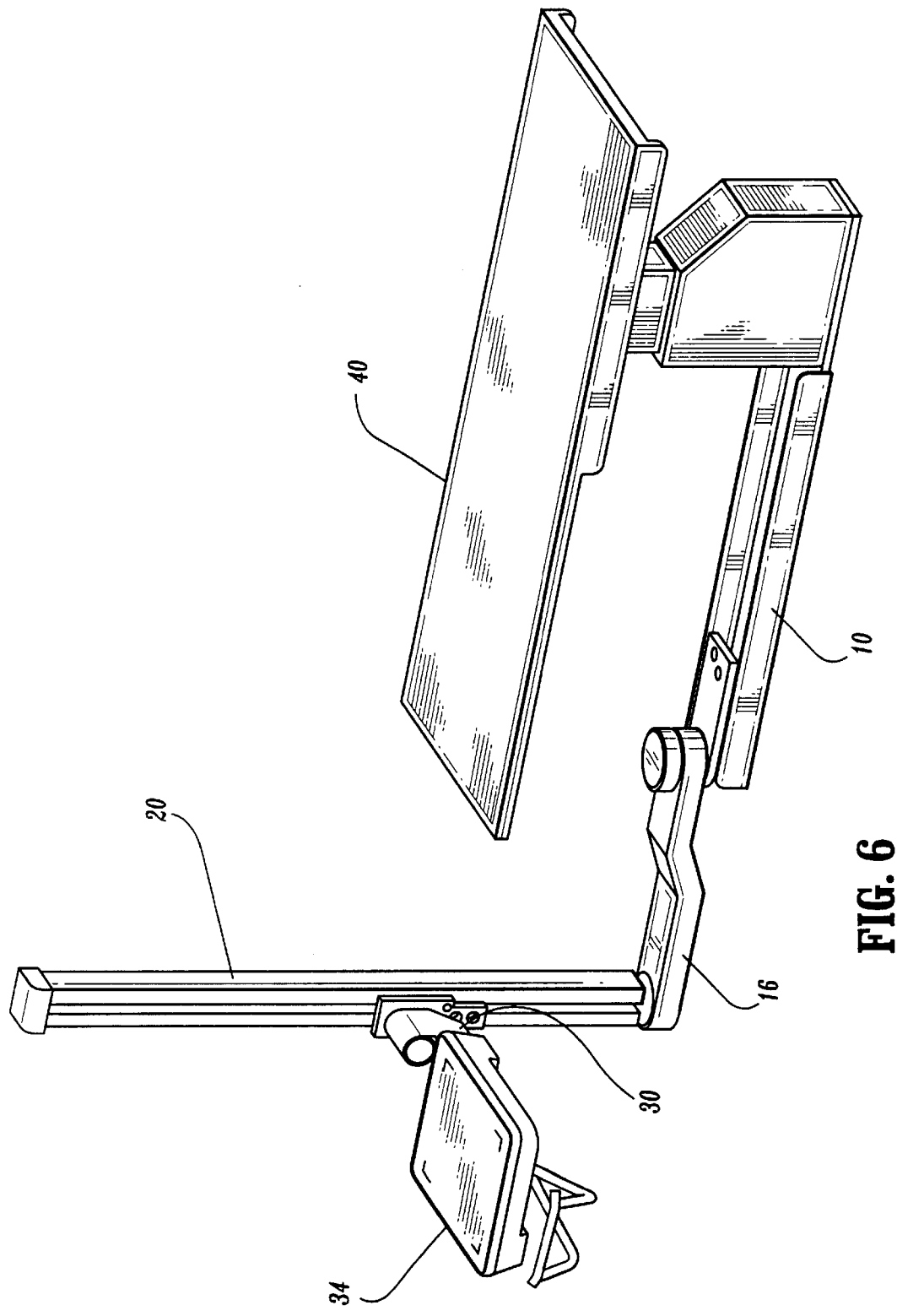
FIG. 6 is a similar illustration, showing the detector also in a horizontal position but spaced from the table, for example to image the arm of a patient without using the patient table.

FIG. 6 illustrates a position of detector 34 suitable for a protocol such as imaging an arm or a hand of patient who can be on a wheelchair, a gurney, or can be standing. The positioning in FIG. 6 is similar to that in FIG. 1 except that detector 34 is lower vertically and is oriented horizontally and facing up. X-ray source 46 again is not shown in FIG. 6 but would be above detector 34.

FIG. 7 illustrates a position of detector 34 suitable for x-ray protocols such as a cross-table lateral view of a patient recumbent or sitting on table 40. For this protocol, detector 34 is oriented vertically, facing a side of table 40. Typically, the lower edge of the image area of detector 34 is at or higher than table 40. X-ray source 46 in this case would be at the other side of table 40, with its x-ray beam directed horizontally at detector 34.

Figure 8:
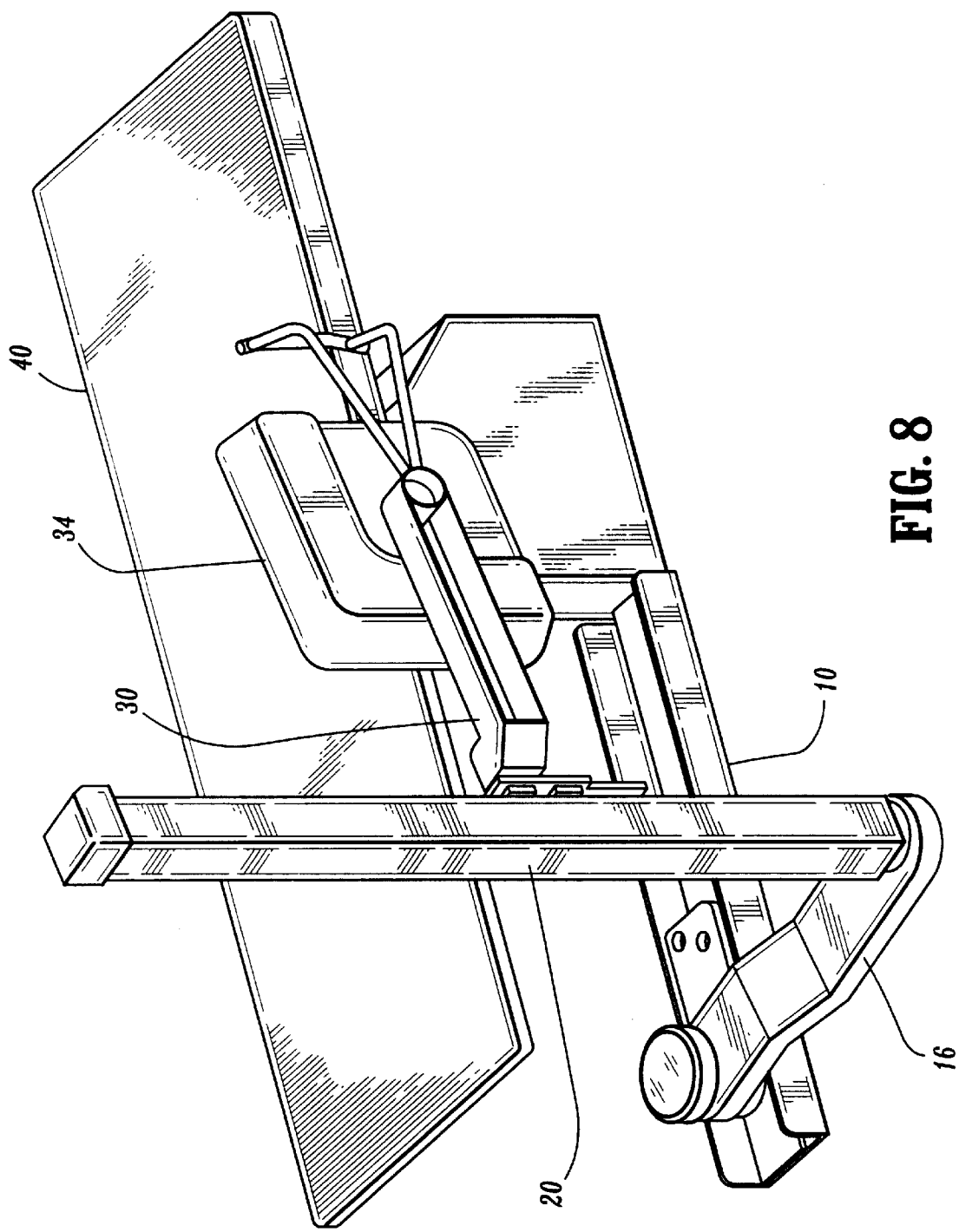
FIG. 8 is a similar illustration, showing the detector in a vertical orientation next to a side of the patent table but angled relative to table side.

FIG. 8 illustrates detector 34 in a position similar to that in FIG. 7, also in a vertical orientation but angled relative to a side edge of table 40, through rotation of lower arm 16 and/or of column 20. X-ray source 46 would be across table 40 from detector 34, typically with the central ray of the x-ray beam normal to the imaging surface of detector 34.

Figure 9:
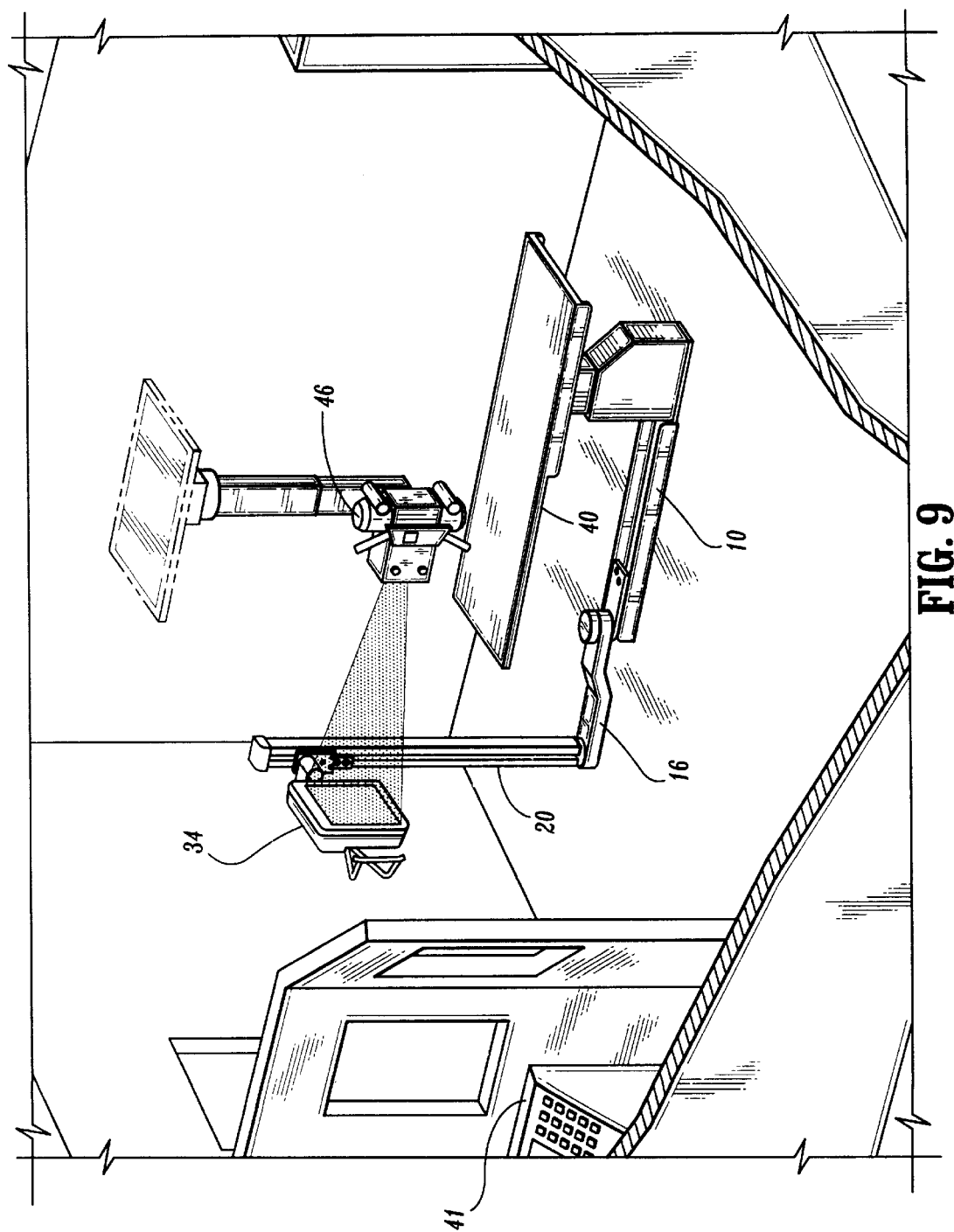
FIG. 9 illustrates the detector as used in an x-ray room that has a ceiling-mounted x-ray source and further illustrates an operator's console processing the detector output and controlling the x-ray examination.

FIG. 9 illustrates detector 34 in a position similar to that in FIG. 1 but shows more of the structure suspending x-ray source 46 from the ceiling, and illustrates a console 41 coupled electrically and electronically with detector 34 and, if desired, with x-ray source 46 and placed behind a known x-ray protection screen.

Figure 10:
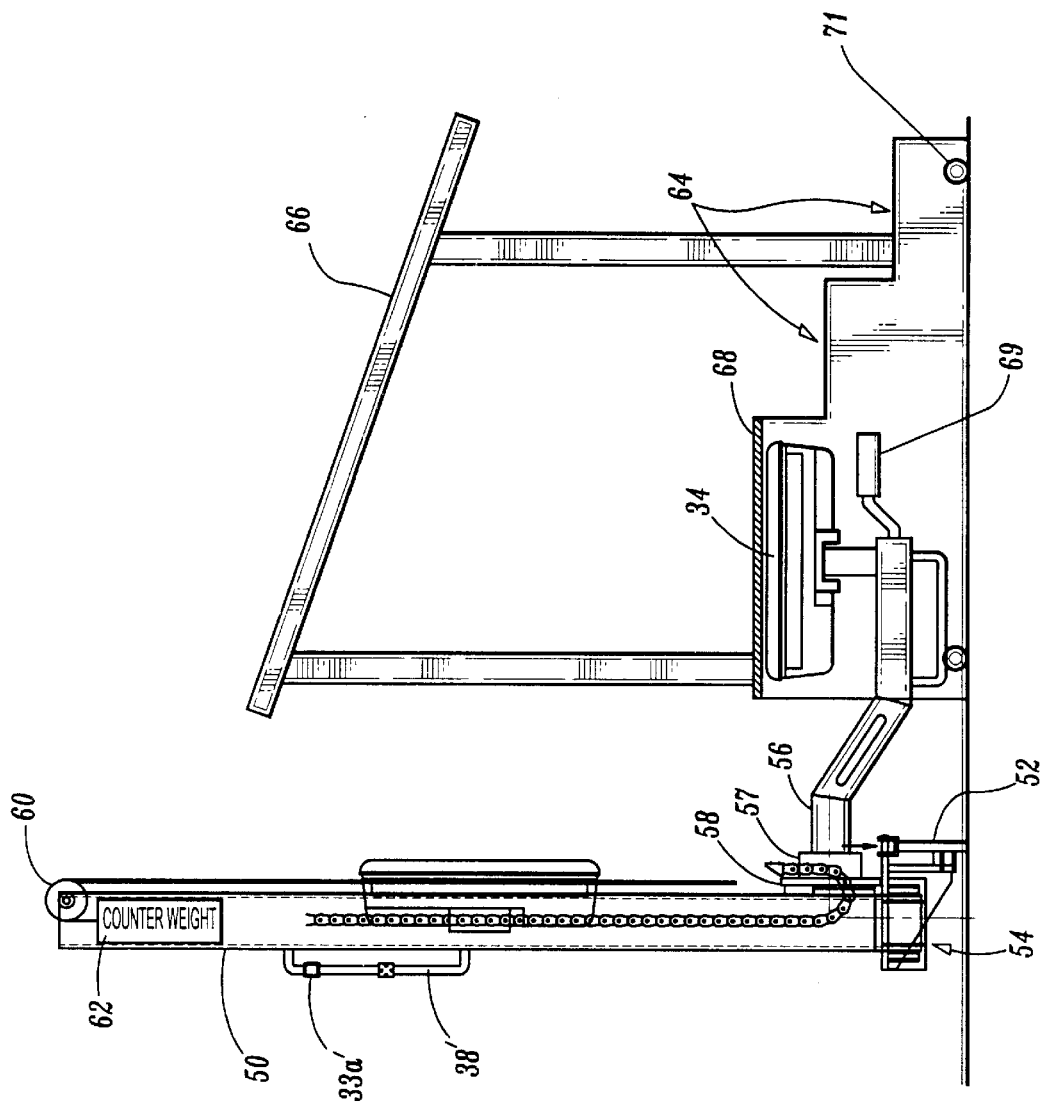
FIG. 10 illustrates another embodiments, suitable for x-ray examination of weight bearing feet or other anatomy.

FIG. 10 illustrates an embodiment that can use only two degrees of freedom for detector 34 and is suitable for x-ray protocols such as imaging patients' feet when weight-bearing. Column 50 in this embodiment is similar to the earlier-described column 20, except that column 50 need not be on a lower arm 16 but can be on a support 52 that can be floor-mounted or can be mounted on a movable platform. Column 50 is rotatably mounted on support 52 through a bearing at 54, to rotate about an upwardly extending axis such as its long axis. An arm 56 is mounted on a slide 58 that moves along column 50, for example through a chain-and-pulley arrangement 60 counter-weighted with a weight 62. Arm 56 is mounted on slide 58 through a bearing at 57 to rotate about a lateral, e.g., horizontal, axis. In use, a patient climbs on steps 64, holding onto a floor or wall mounted handrail 66 if desired, and stands on a low platform 68 that is essentially transparent to x-rays. Detector 34 can be positioned as illustrated, in a horizontal orientation under platform 68, facing up. X-ray source 46 would be above the patient's feet, with the x-ray beam directed down toward detector 34. By grasping a handle 69, an operator can pull detector 34 from under platform 68 by rotating column 50 through arm 56, and can then rotate arm 56 about bearing 57 to move detector 34 to a vertical orientation adjacent to and aligned or above platform 60 for an x-ray protocol calling for a lateral image of the patient's feet. An assembled unit comprising steps 64, platform 68 and a handrail 66 secured thereto can be on wheels 71 so that it can be moved as needed.

Figure 11:
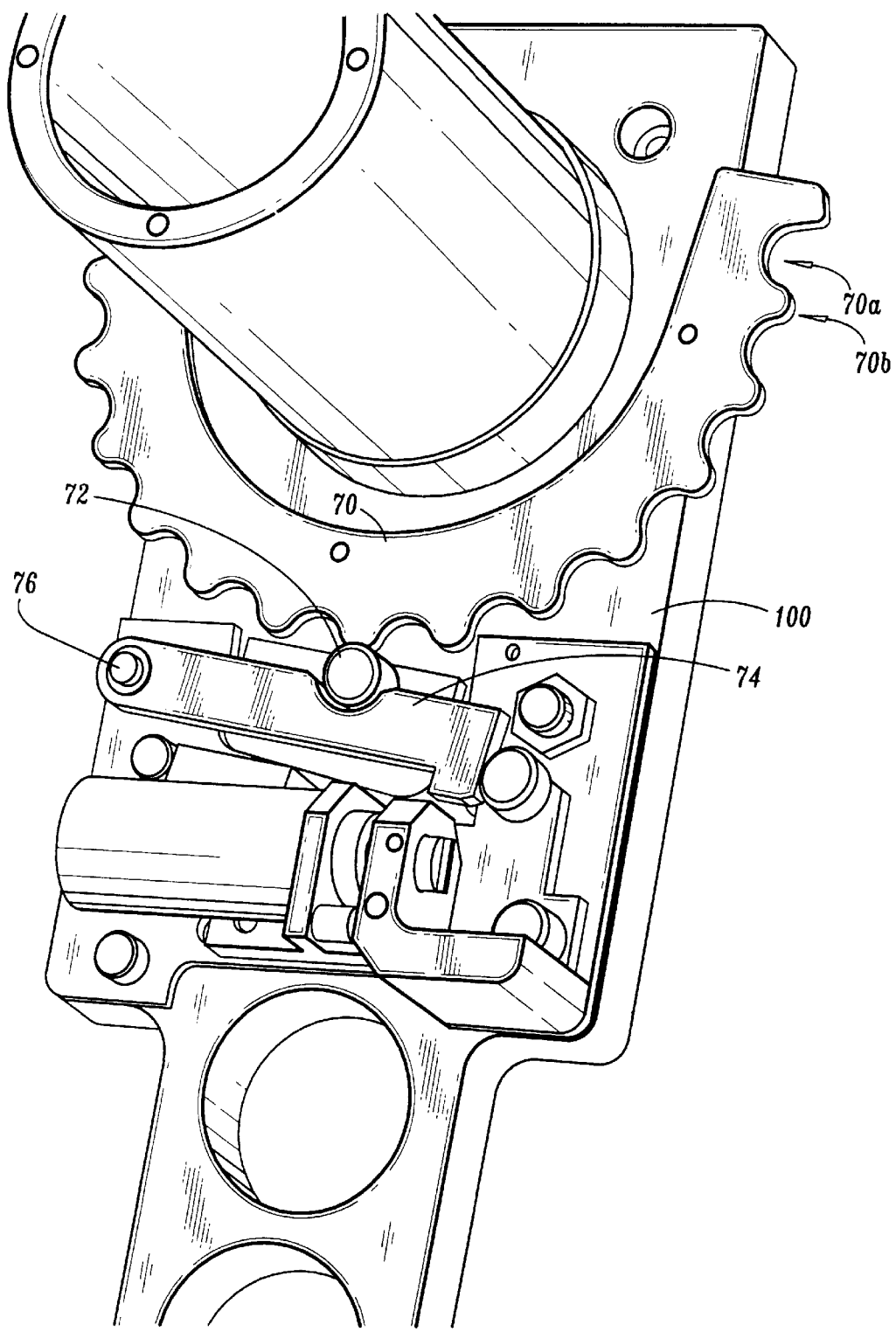
FIG. 11 illustrates a locking detent used in positioning the detector, with the detent in a position during detector motion.
Figure 12:
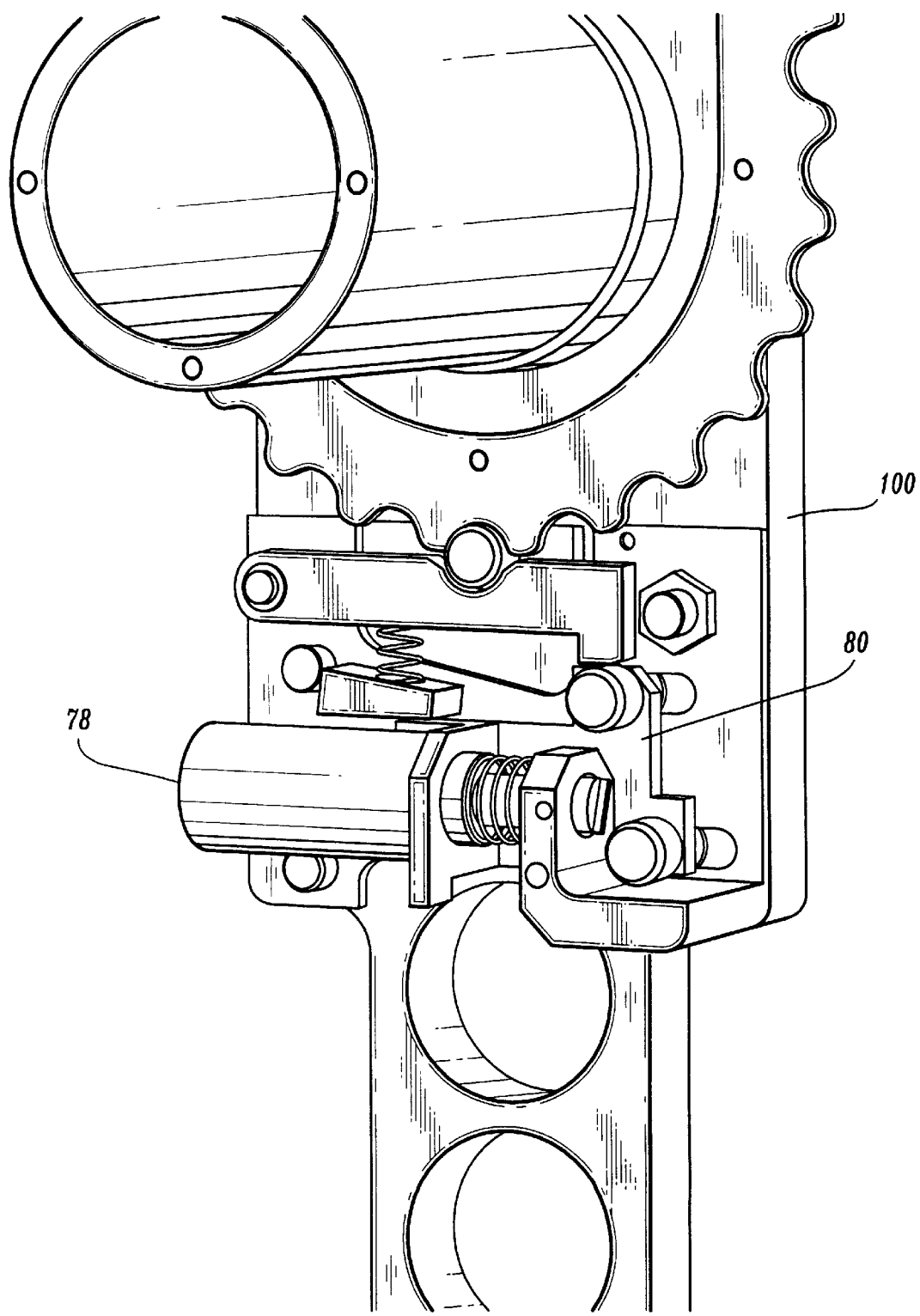
FIG. 12 illustrates the detent in a locked position.

FIGS. 11 and 12 illustrate a locking detent mechanism that can be used for one or more of the rotational motions described above. In a currently preferred embodiment, such a detent is used for the rotation of lower arm 16, column 20 and upper arm 30, and can be used for rotation of detector 34 about bearing 36 (FIG. 7). A similar detent can be used for the rotation of column 50 and arm 56 in the embodiment of FIG. 10. Taking as a representative example the rotation of lower arm 16 about lower slide 14, and referring to FIGS. 11 and 12, a plate 100 is secured to, or is a part of the non-rotating element, in this example slide 14, and a cogwheel 70, or a segment of such a cogwheel is secured to the rotating part, in this example lower arm 16. Cogwheel 70 has a pattern of valleys 70a and teeth 70b. A cam wheel 72 is mounted for free rotation on a lever 74, which in turn is pivotally mounted on plate 100 at a pivot 76 and is biased toward cogwheel 70 by a spring 77 (FIG. 12). When lower arm 16 is urged into rotation with a force sufficient to overcome the bias of spring 77, as well as inertial and friction, camwheel 72 rides over the teeth of cogwheel 70 but when the force rotating lower arm 16 is below a threshold, the mechanism forces camwheel 72 into a valley 70a, so that the rotation of lower arm 16 stops at one of the several preferred positions, spaced approximately 15° apart in a currently preferred embodiment. When lower arm 16 is in a desired position, the detent mechanism is locked by releasing a solenoid 78 to allow its spring to force lever 80 to its position illustrated in FIG. 12, in which it comes under the right side of lever 74 to keep camwheel 72 in a valley and thus prevent rotation of lower arm 16. To allow rotation of arm 16, solenoid 78 must be energized to pull lever 80 to the position thereof illustrated in FIG. 11, which can be done, for example, by operation of a control button 38a on handle 38 in the case of the embodiment of FIGS. 1–9 or similar button 38'a on handle 38' in the embodiment of FIG. 10. While identical types of detents can be used for each rotational motion, a different arrangement of cogwheel teeth may be desired. For example, rotation about bearing 36 may require only two or three preferred positions C portrait, landscape and diagonal orientations C in which case the cogwheel may need only three valleys between teeth. Other rotations may require a different angular range, in which case the segment of cogwheel 70 that is used may have a different inclusion angle.

Alternatively, electronic, electromechanical and/or mechanical brakes and clutches can be used to immobilize and release the connections between parts that can move relative to each other. Using such brakes and clutches can allow the operator to move detector 34 to the desired position manually with ease, and can securely fix detector 34 in a position for exposure. For example, the operator can trip switch 38a to engage such clutch or clutches and/or brake or brakes to thereby allow motion, and can trip the switch to disengage such clutch(es) and/or brake(s) to thereby prevent motion. Such a clutch and/or brake arrangement can be used for one or more of the motions described above. Separate such arrangements can be used for different ones of the motions.

Instead of manually moving detector 34 to the desired position as described above, respective electric or other motors can be used to drive some or all of the motions discussed above, under operator control. Alternatively, some or all of the motions can be automated, so that the operator can select one of several preset motion sequences, or can select vertical, horizontal and angular positions for detector 34, and computer controls can provide the necessary motor control commands. Particularly when movements are power-driven rather than manual, proximity and/or impact sensors can be used at the moving parts as a safety measure, generating stop-motion signals when a moving part gets too close to, or impacts with, an object or a patient.

Detector 34 can contain a flat panel detector that converts x-rays directly into electrical signals representing the x-ray image, using a detection layer containing selenium, silicon or lead oxide. Alternatively, detector 34 can contain a flat panel detector that uses a scintillating material layer on which the x-rays impinge to generate a light pattern and an array of devices responsive to the light pattern to generate electrical signals representing the x-ray image.

The disclosed system can be used for tomosynthesis motion, where the x-ray source and the detector move relative to each other and the patient, or at least one of the source and detector moves, either in a continuous motion or in a step-and-shoot manner. The image information acquired at each step (or each time increment) can be read out and the detector reset for an image at the next step (or time increment). An alternative method of performing tomosynthesis can be used where the source and detector motions relative to the patient occur as described above, but only one image is generated from the entire motion sequence, representing a composite image acquired over all the positions.

The disclosed system provides for a number of motions to accommodate a wide variety of imaging protocols: the x-ray detector image plane rotates between vertical and horizontal and can be locked at intermediate angles as well; the detector moves horizontally along the length of the patient table as well as across the length of the patient table so that it can be positioned at either side of the table; the detector moves vertically, the detector can move between portrait and landscape orientations for non-square detector arrays and/or for desired orientation of the array grid even for square arrays; and the detector can combine some or all of these motions in order to get to any desired position and orientation.

Safety can be enhanced by moving the detector by hand, so the operator can observe all motion and ensure safety. Sensors can be provided for collision detection when any motion is motorized. When any motion is motorized, easy-stall motors can be used to enhance safety. In addition, when any motion is motorized, encoders can be provided to keep track of the positions of moving components, and the encoder outputs can be used for software tracking and collision avoidance control. When motions are motorized, preset motor controls can be stored in a computer and used to drive the detector motion for specified imaging protocols or detector positions so that the detector can automatically move to a preset position for a given imaging protocol. Undesirable motion can be avoided or reduced by using clutch controls, hand brakes, counter-balancing, and/or detents that help identify and maintain a desired detector position and orientation and help prevent grid oscillation and focusing grid misalignment.

Figure 13:
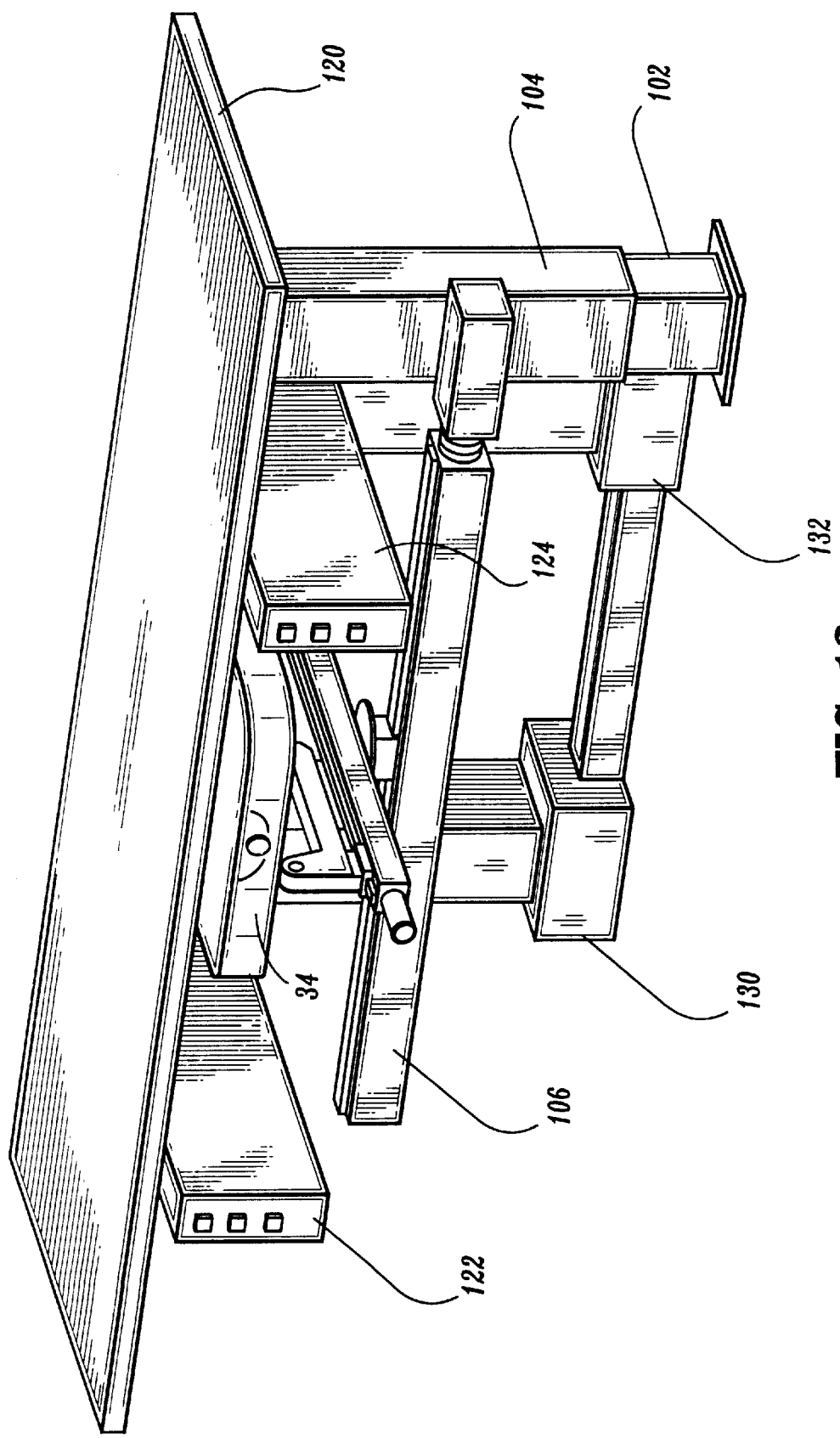
FIGS. 13–27 illustrate another embodiment.
Figure 14:
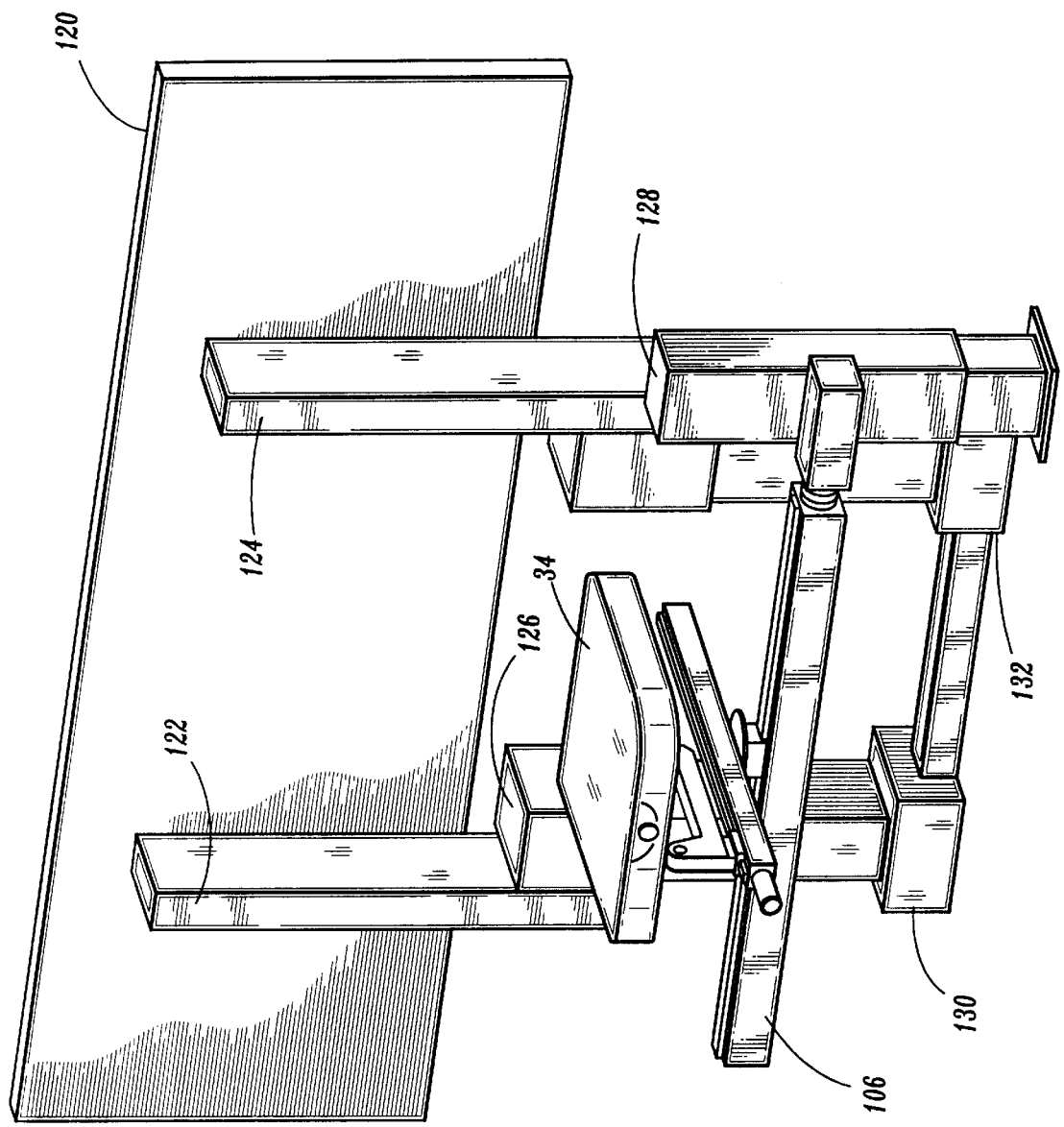
Figure 15:
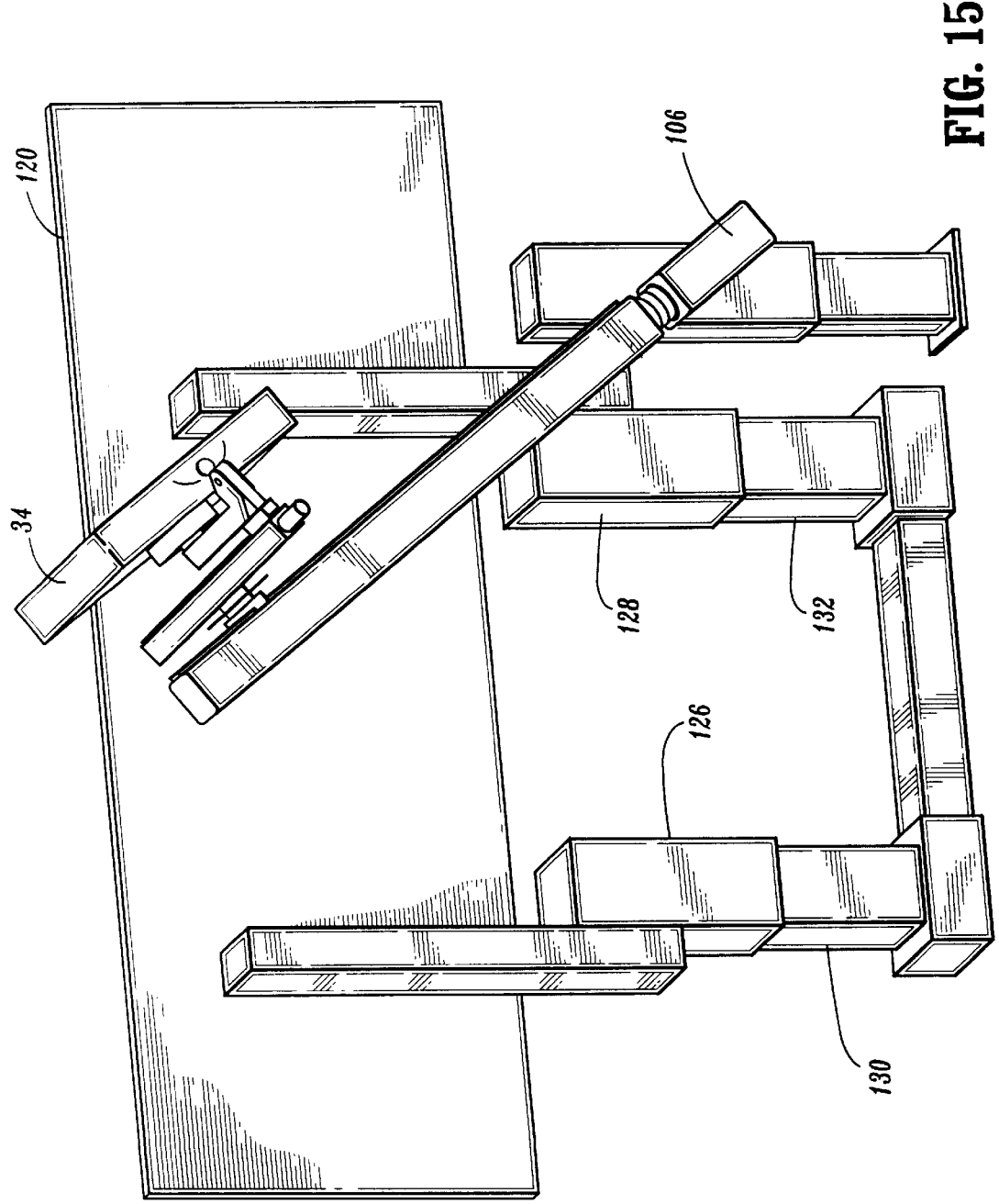
Figure 16:
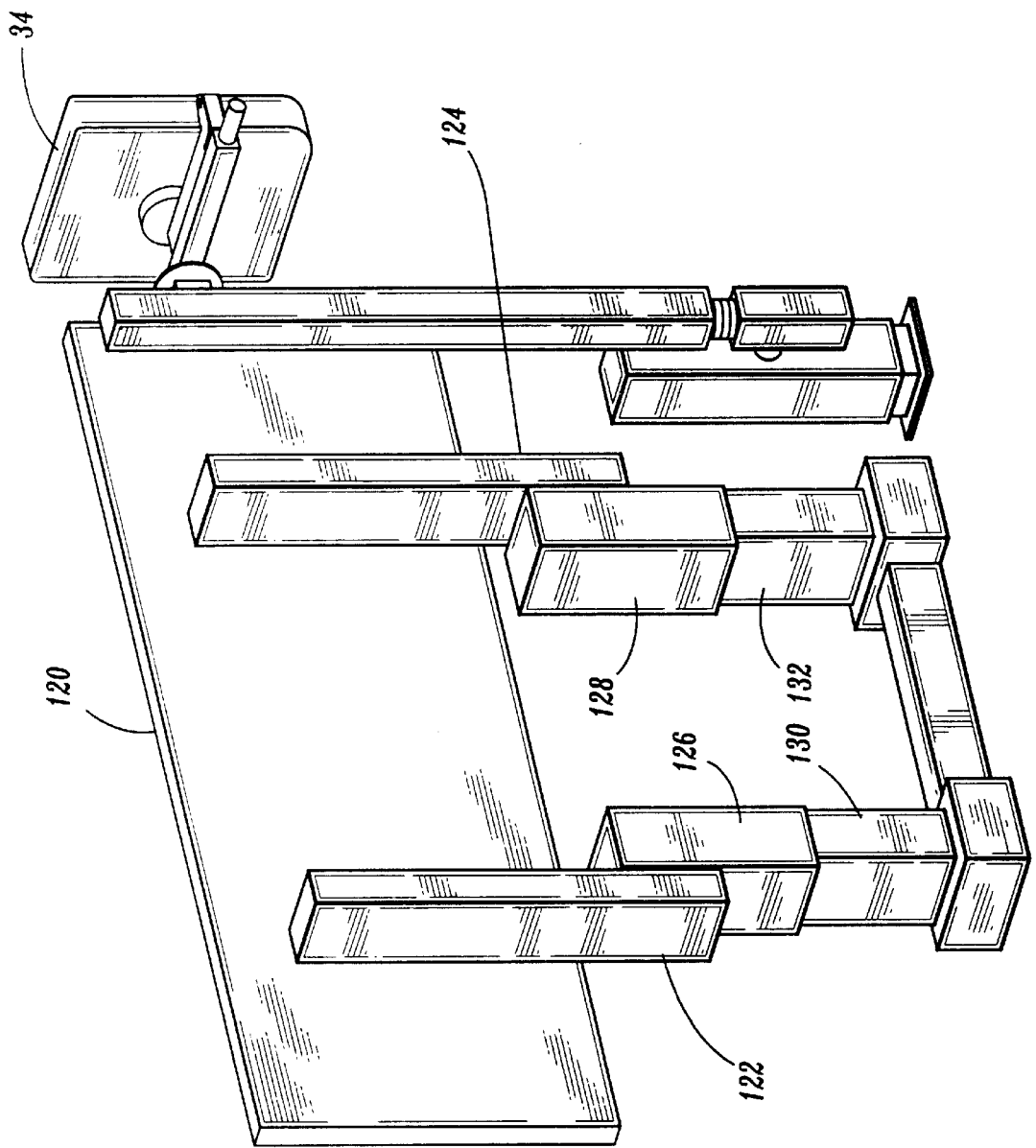
Figure 17:
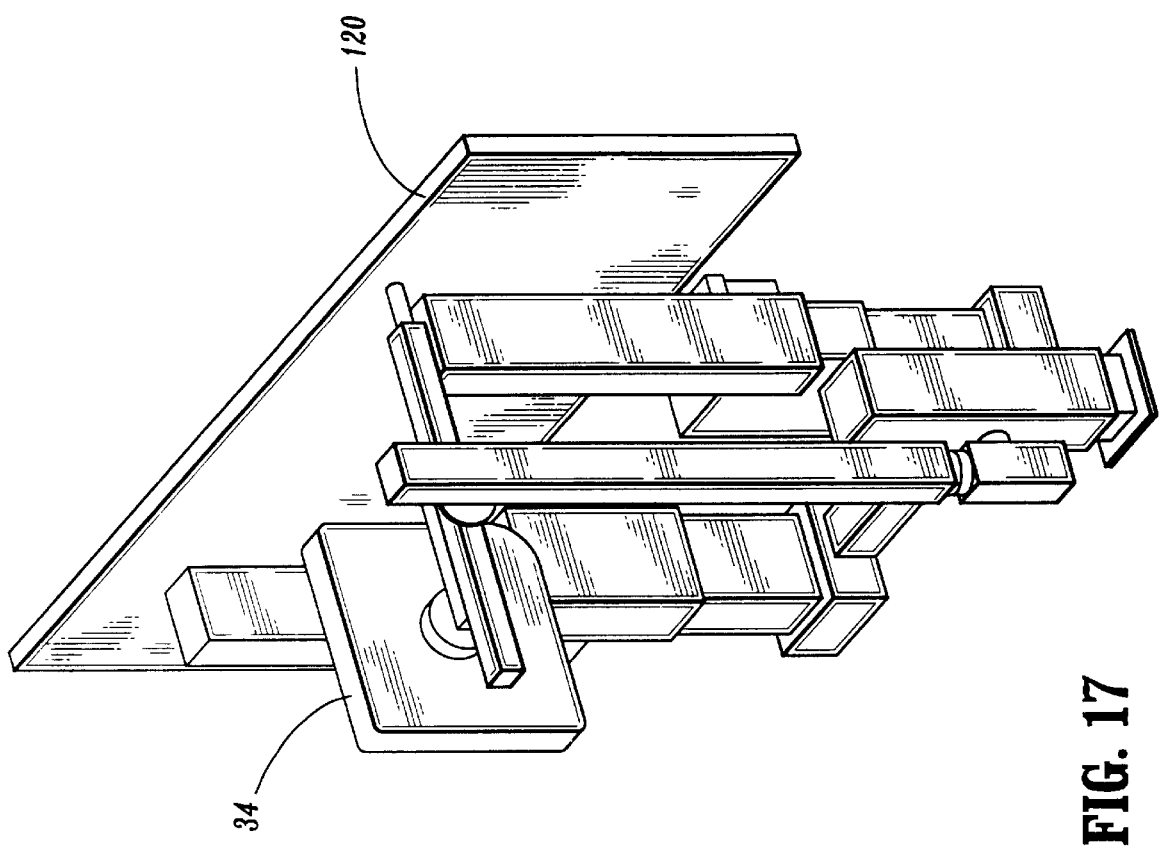
Figure 18:
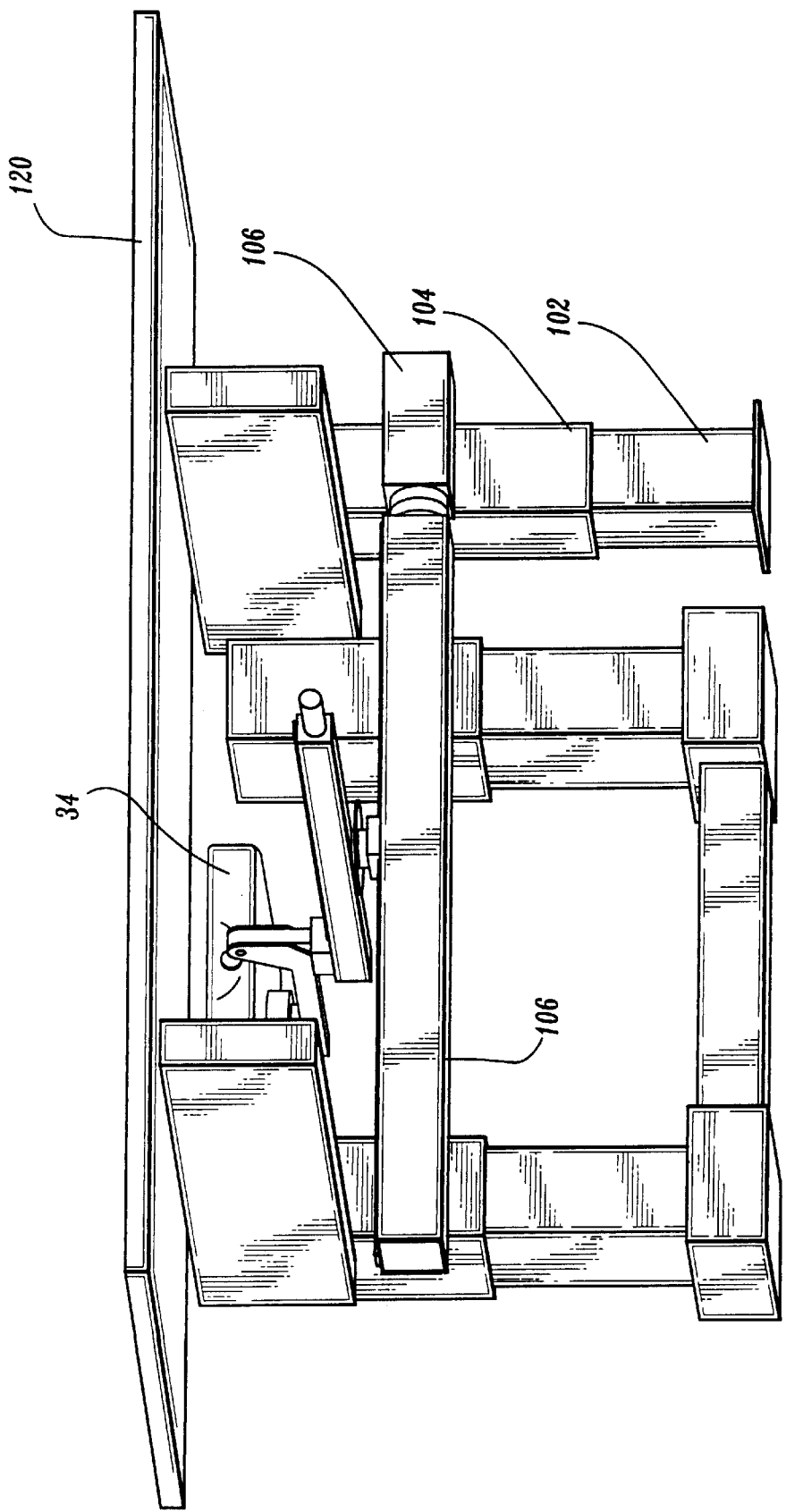
Figure 19:
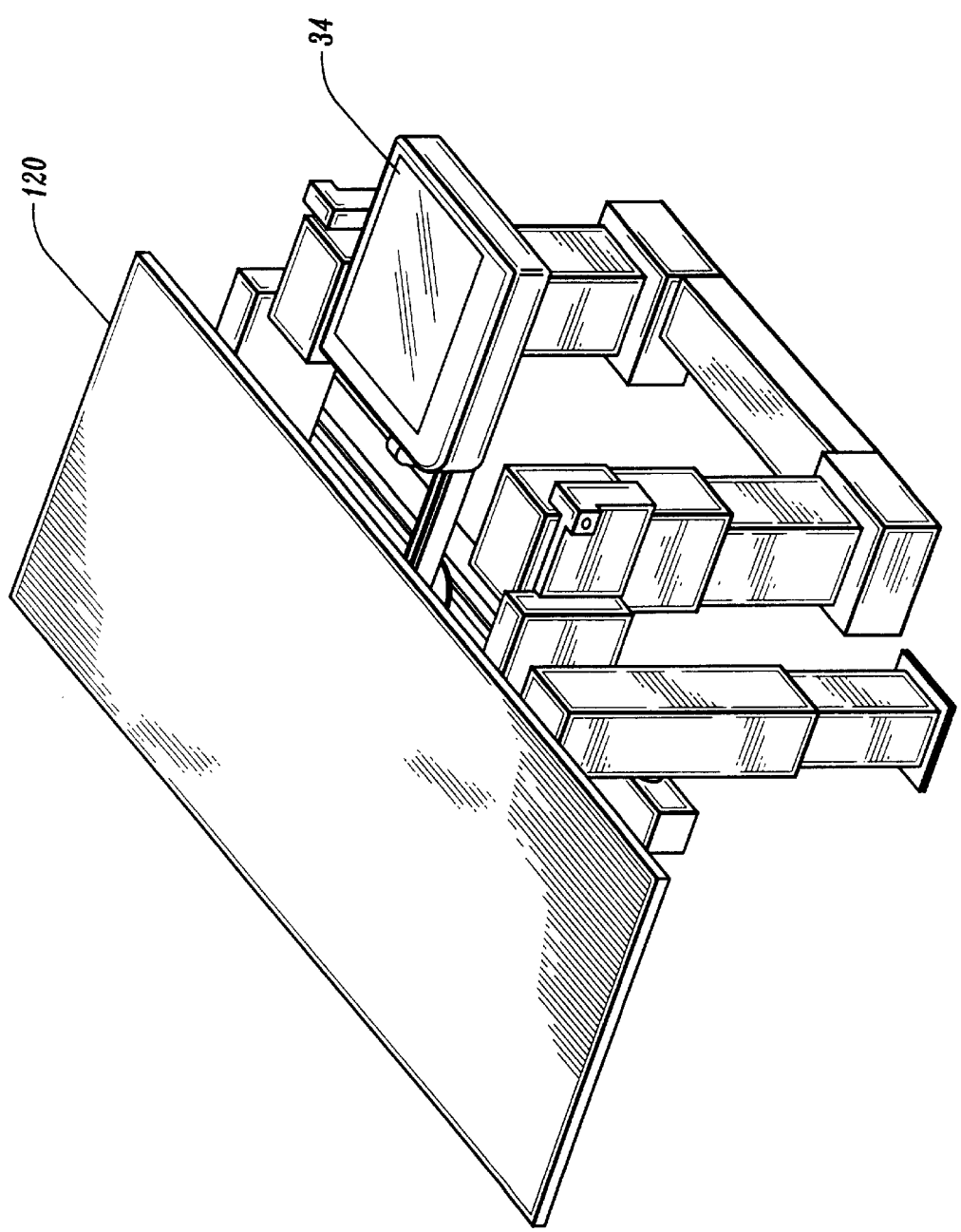
Figure 20:
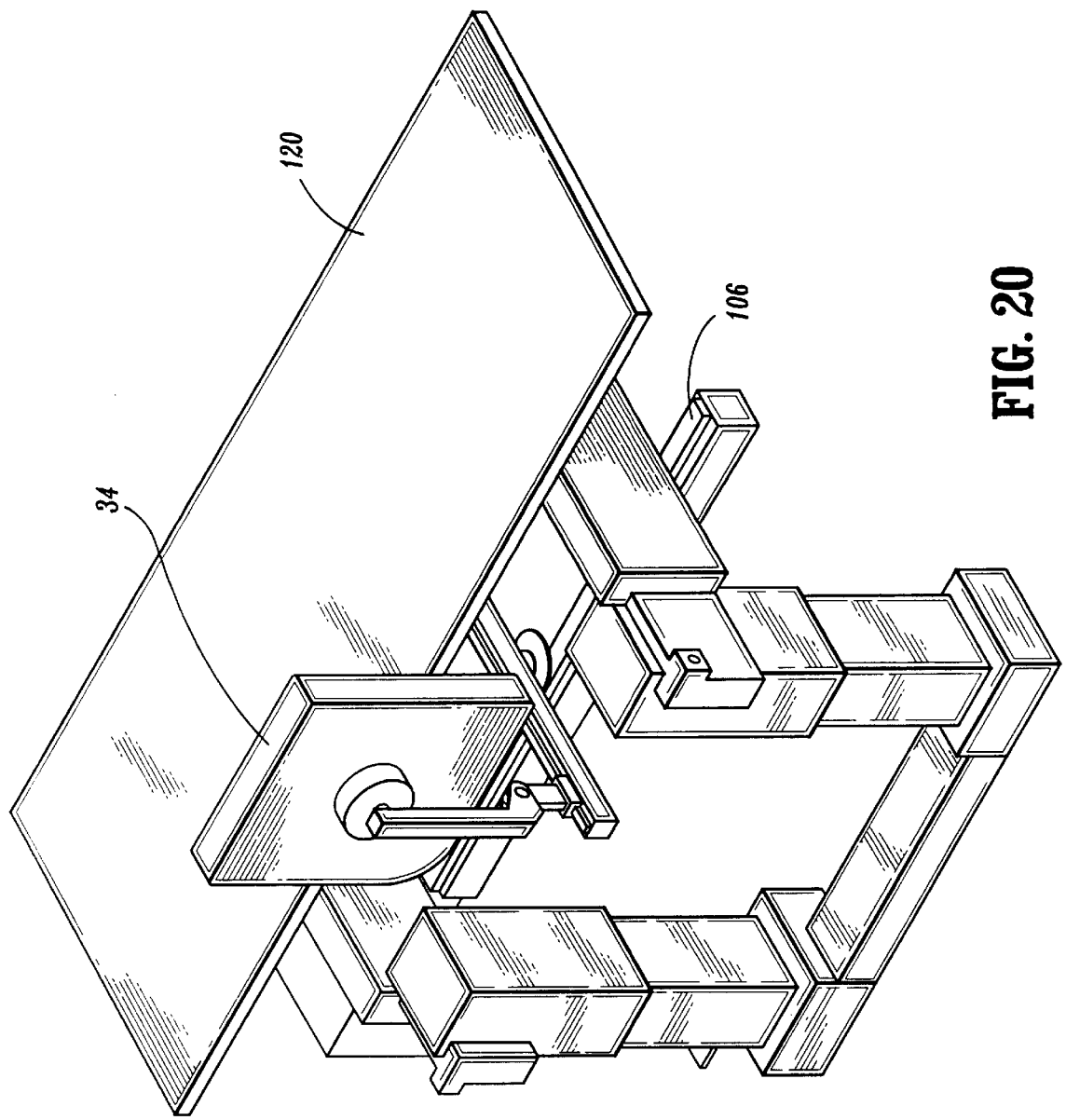
Figure 21:
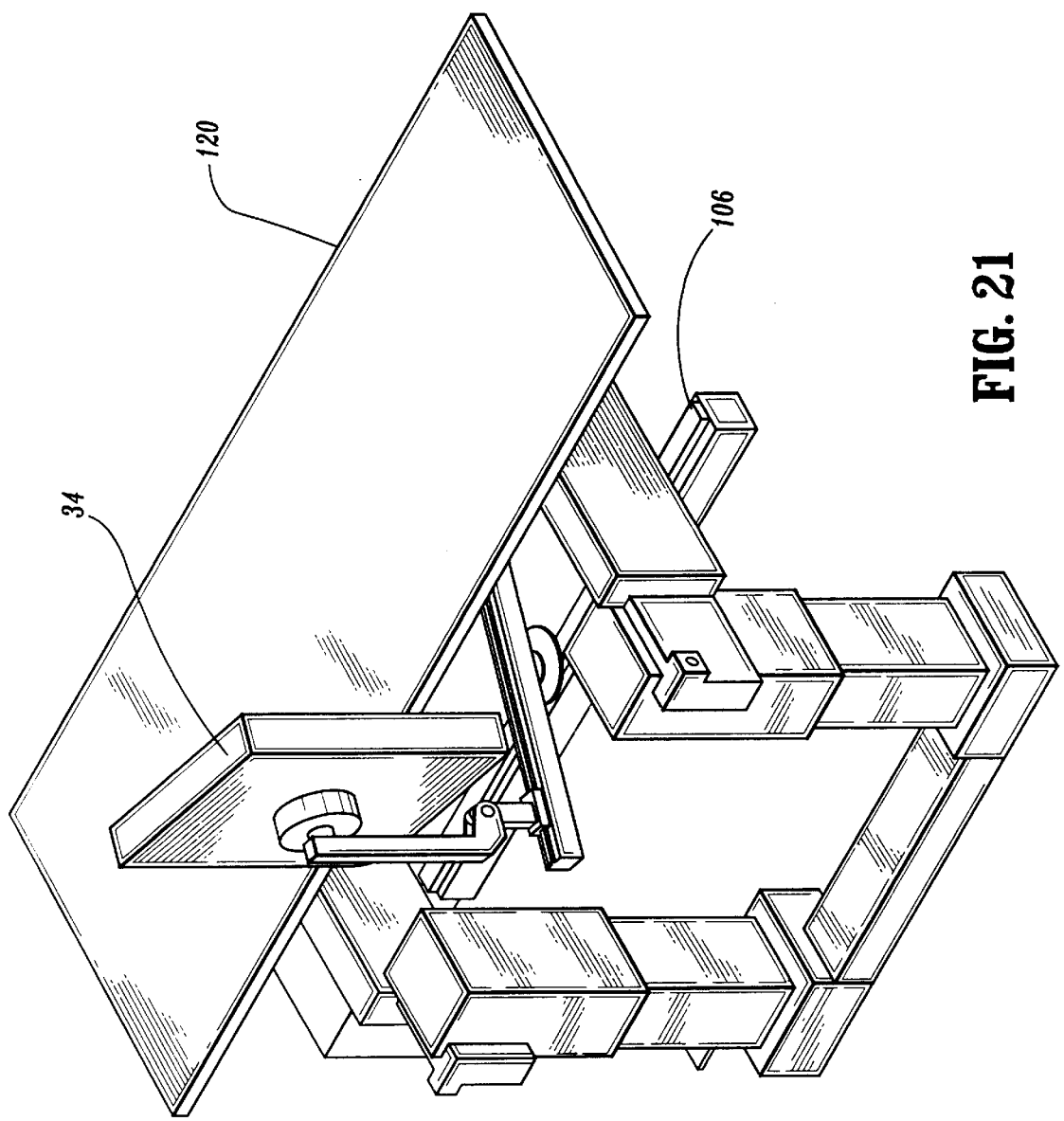
Figure 22:
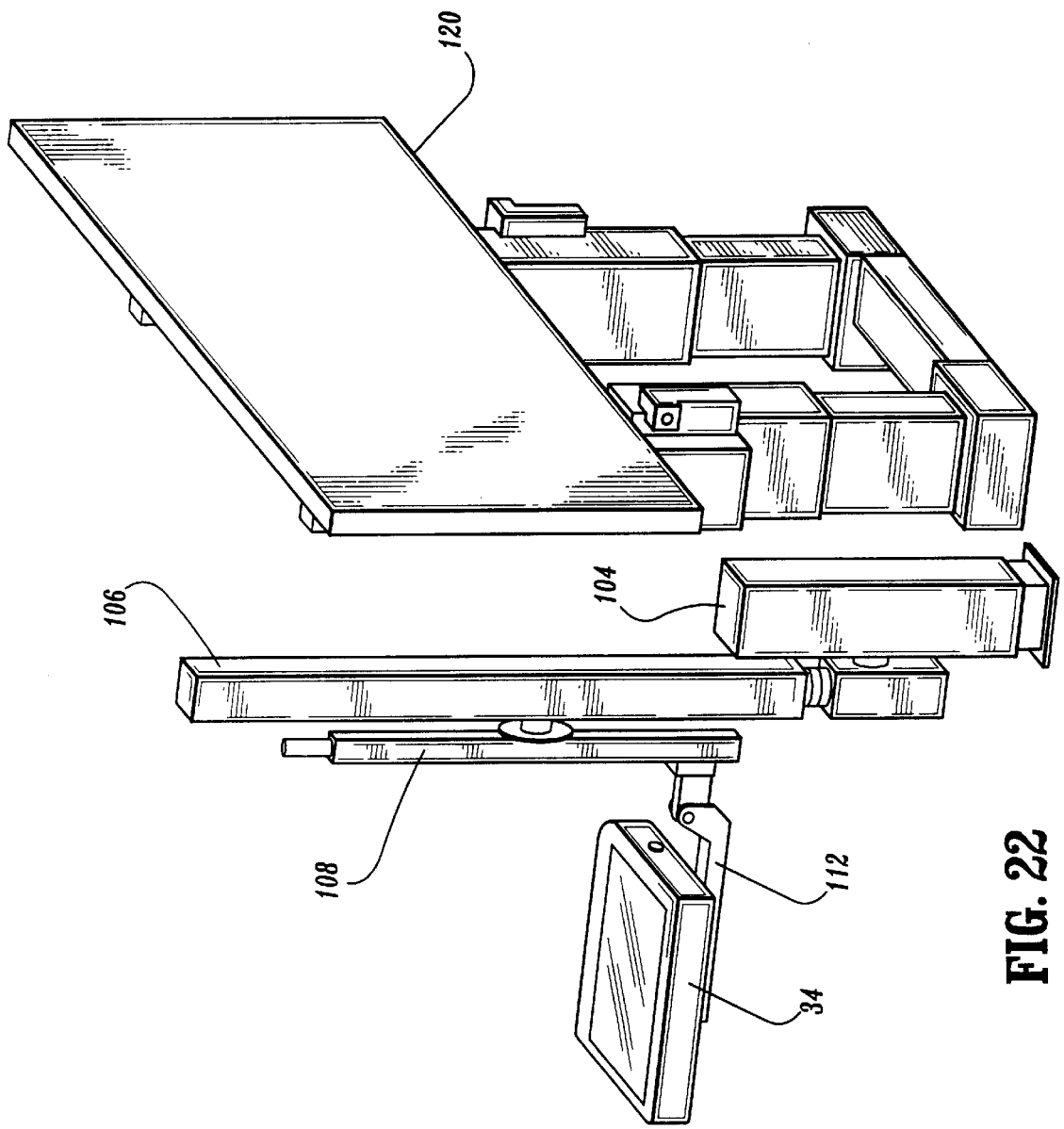
Figure 23:
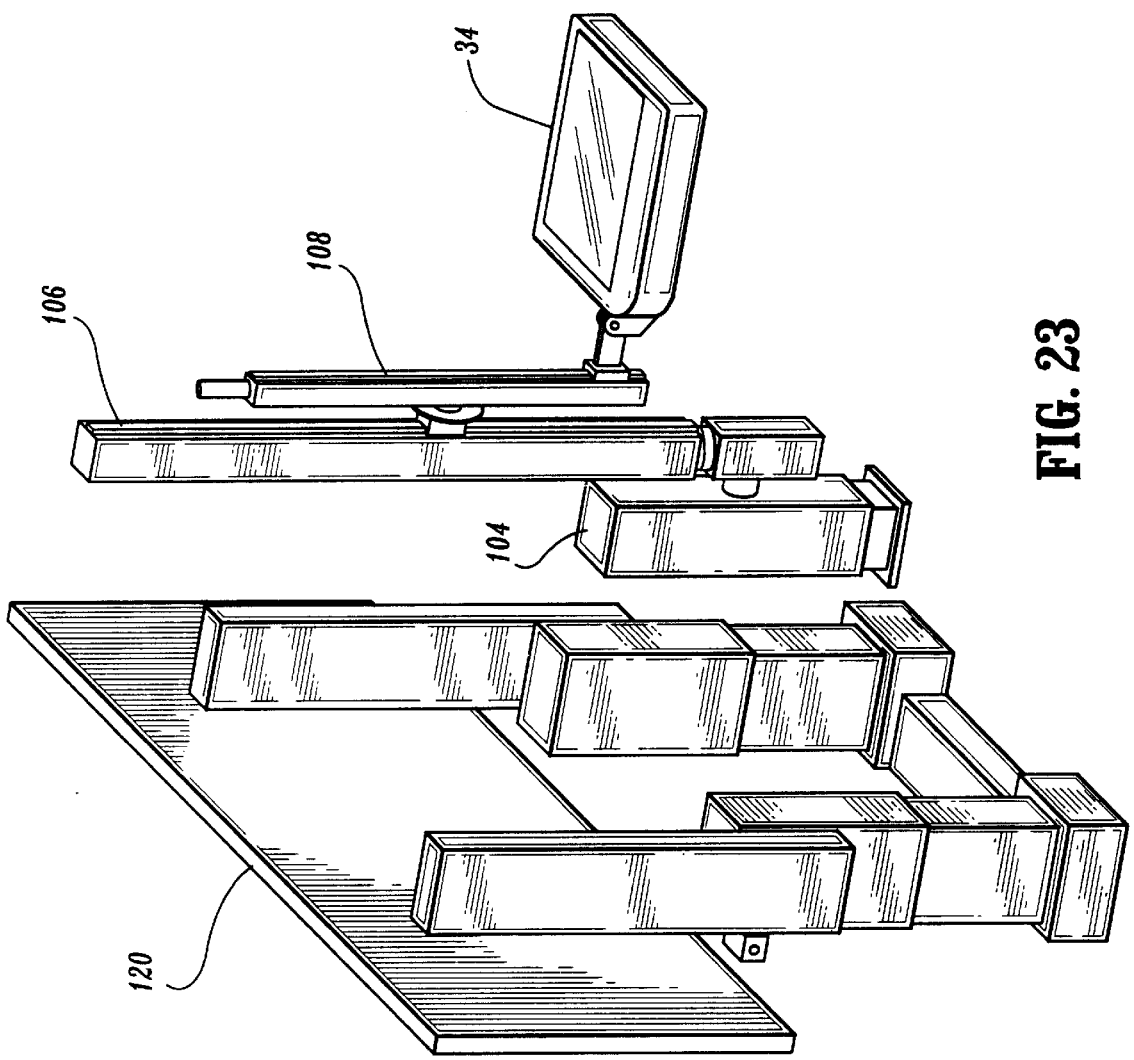
Figure 24:
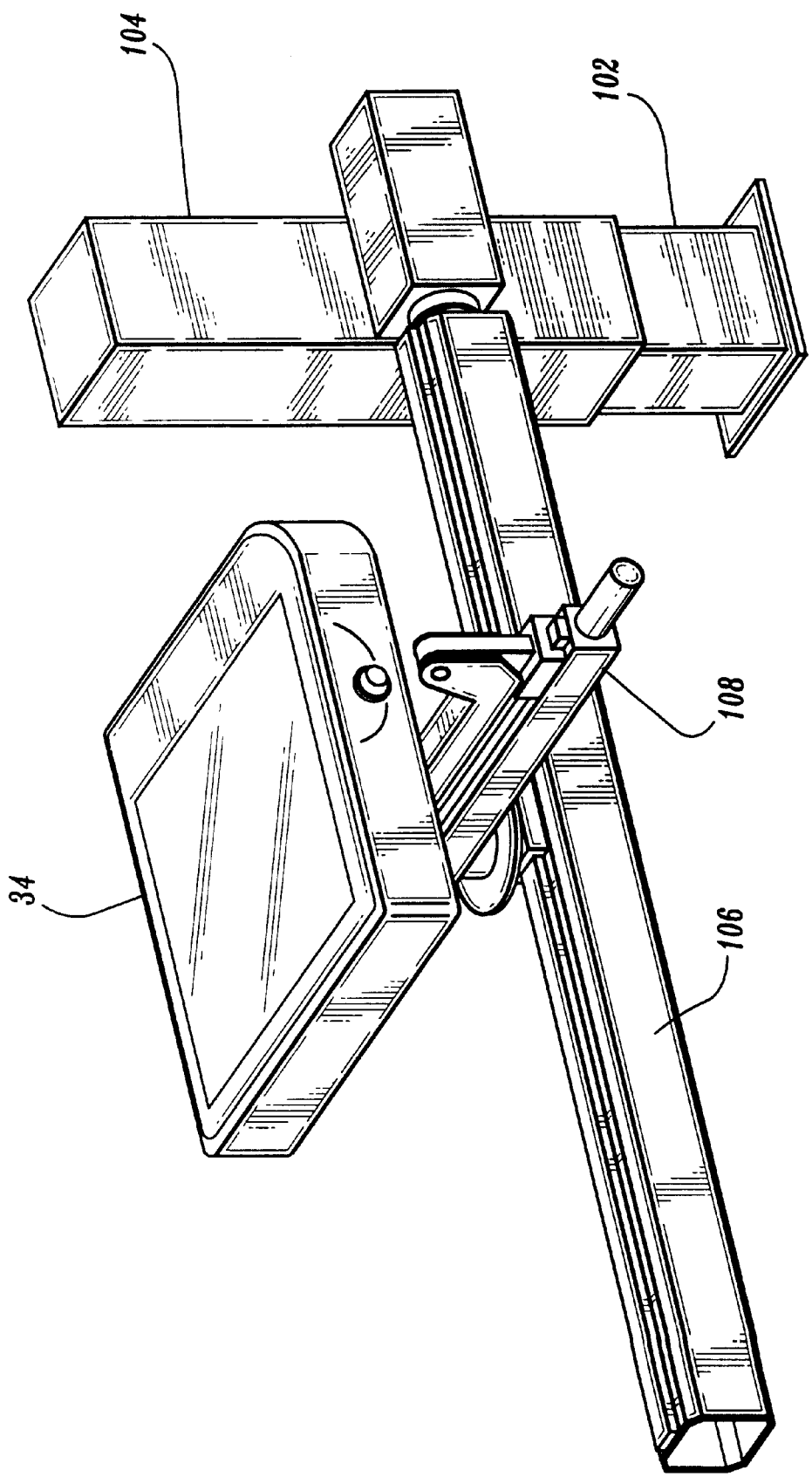
Figure 25:
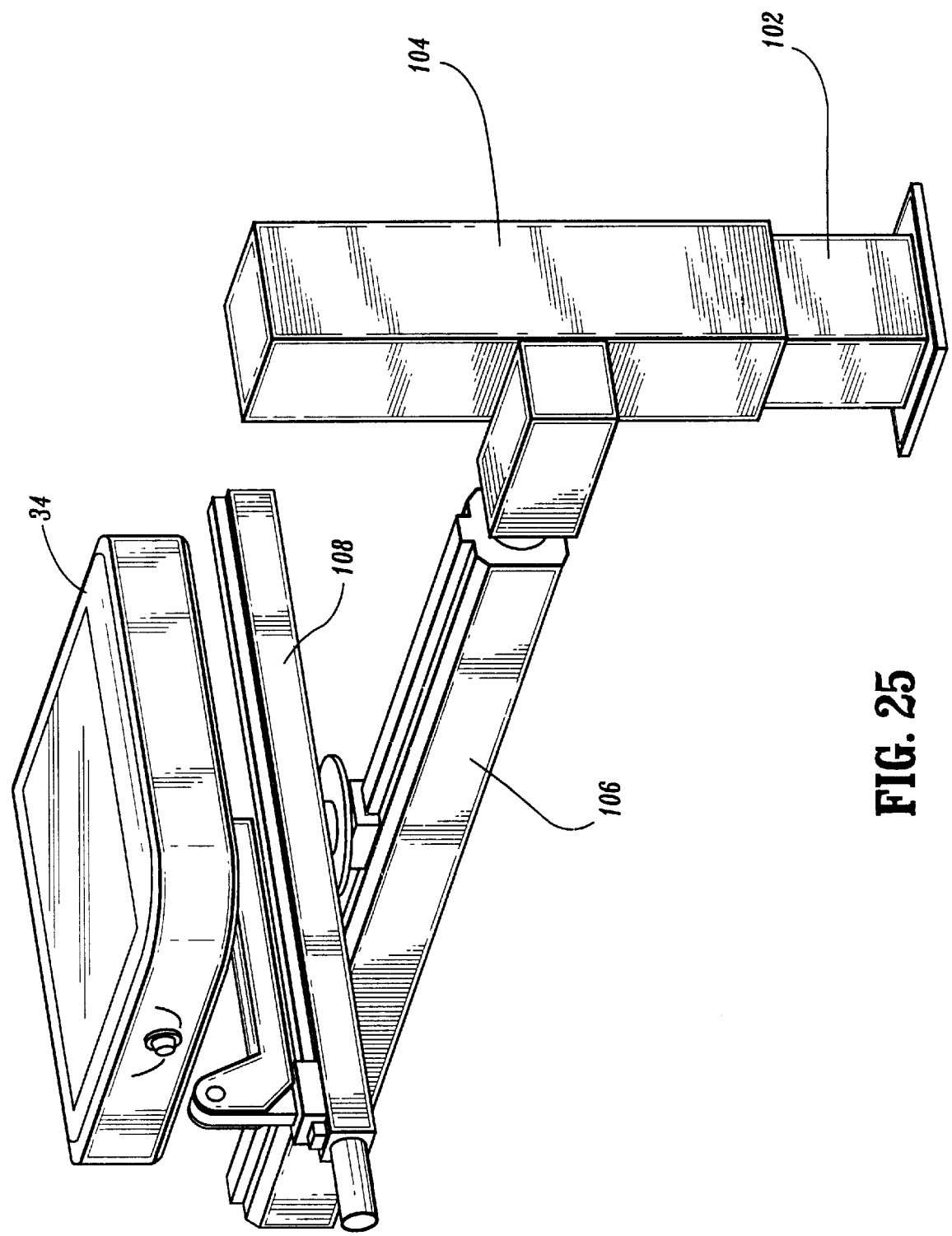
Figure 26:
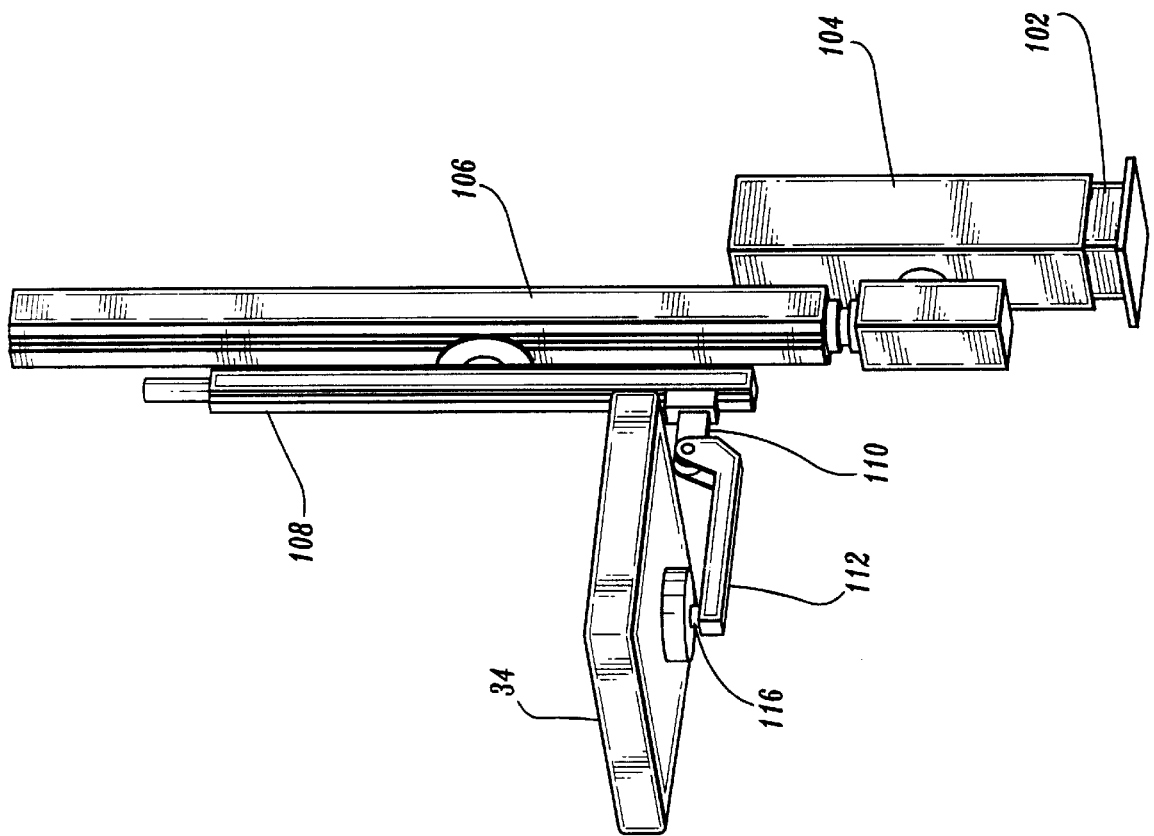
Figure 27:
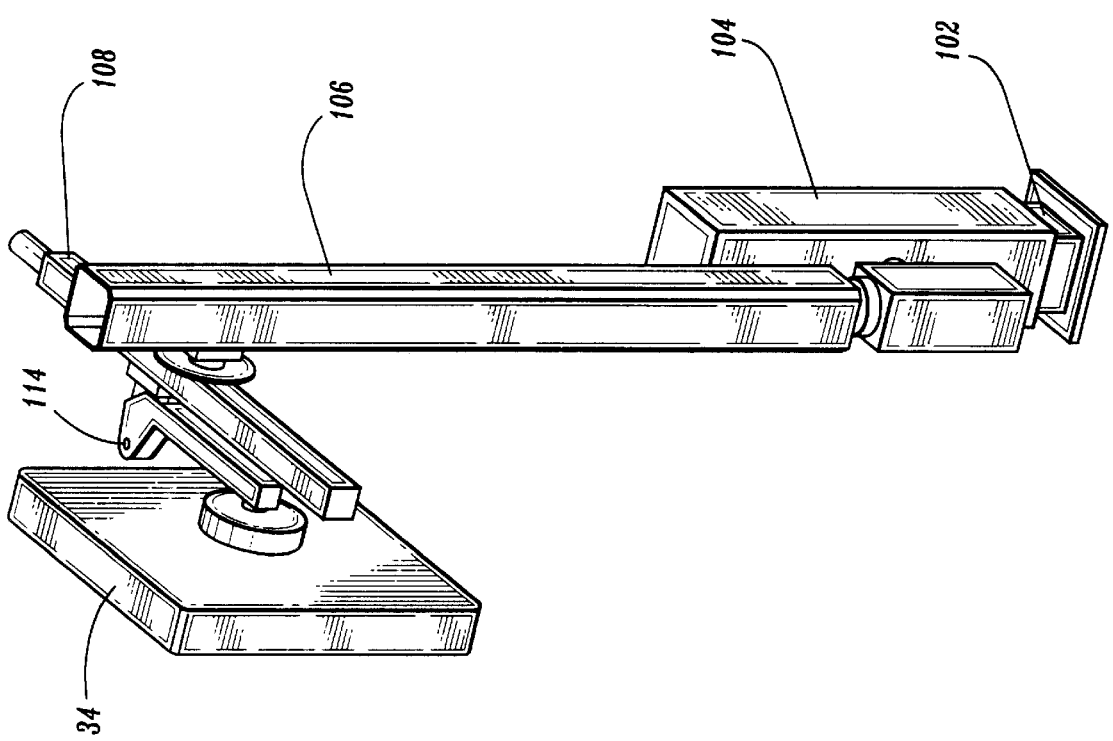
Figure 30:
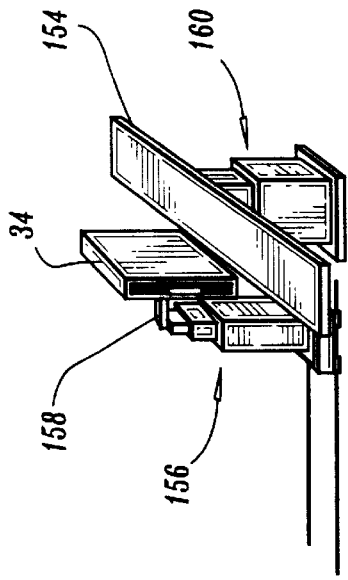
FIGS. 28–38 illustrate yet another embodiment.
Figure 31:
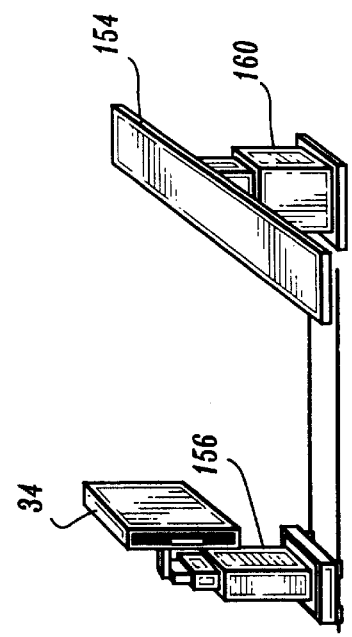
Figure 28:
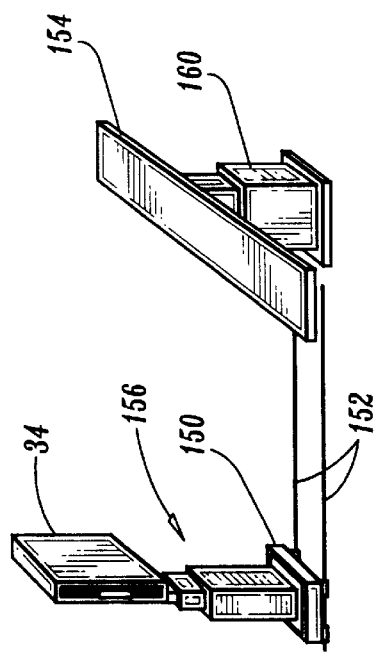
Figure 29:
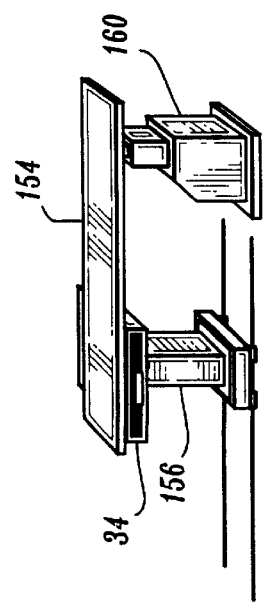
Figure 32:
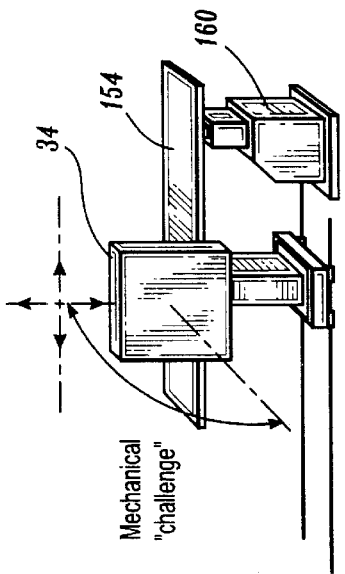
Figure 33:
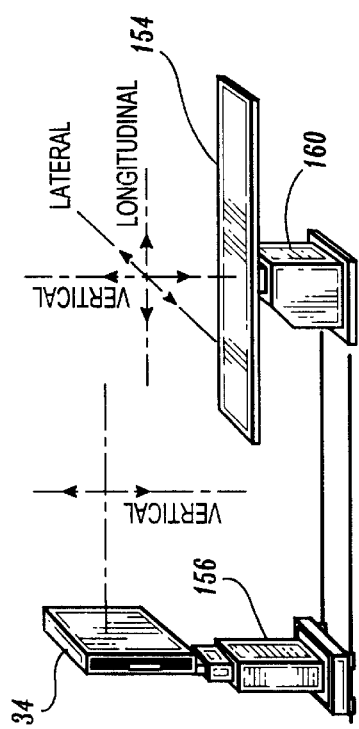
Figure 34:
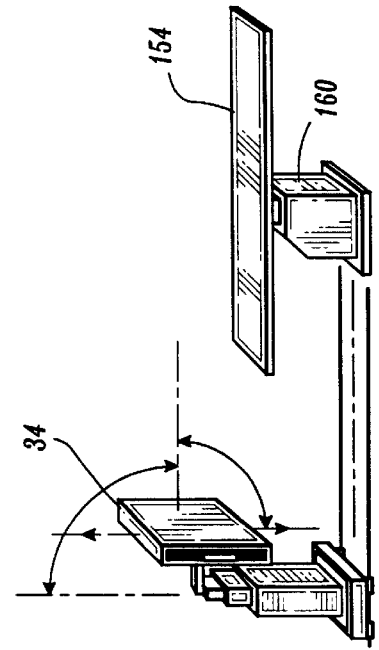
Figure 35:
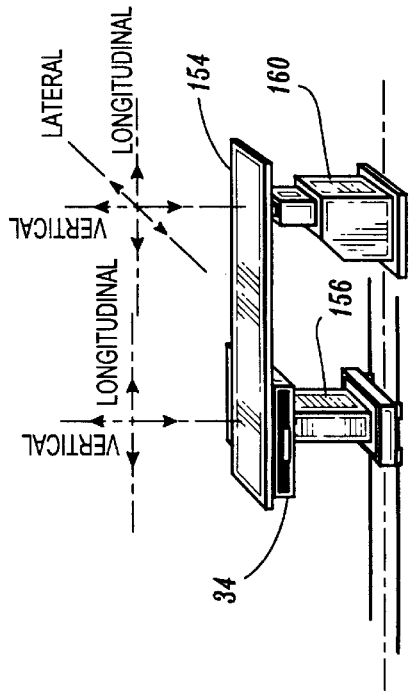
Figure 38:
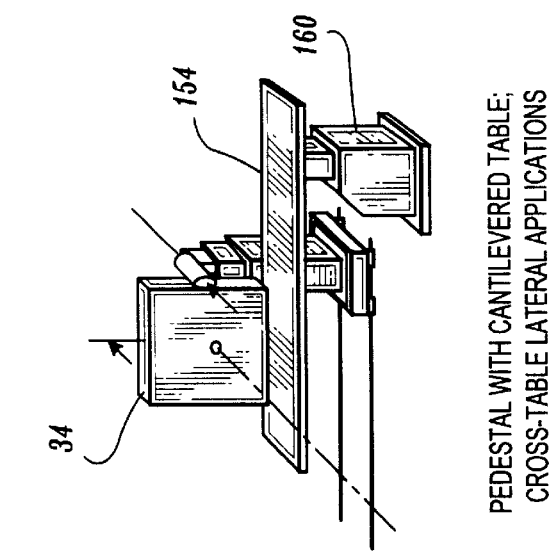
Figure 36:
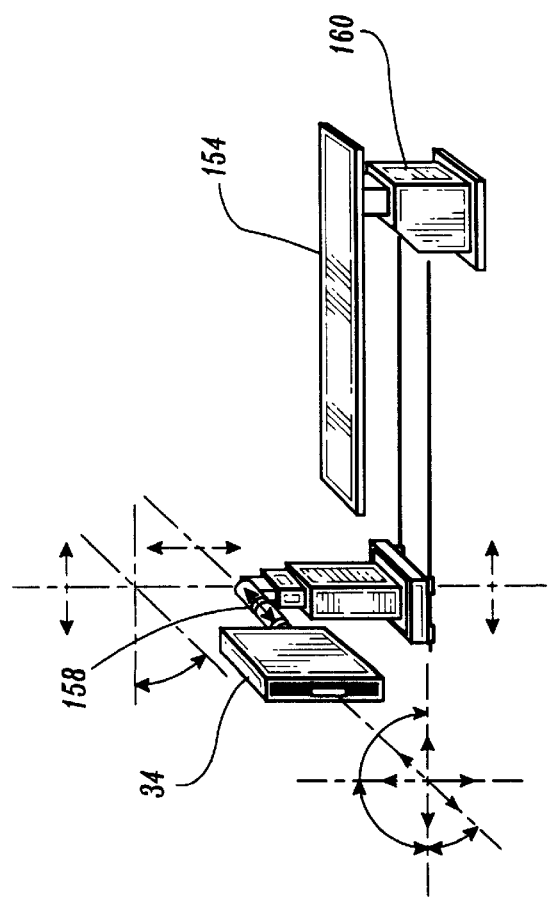
Figure 37:
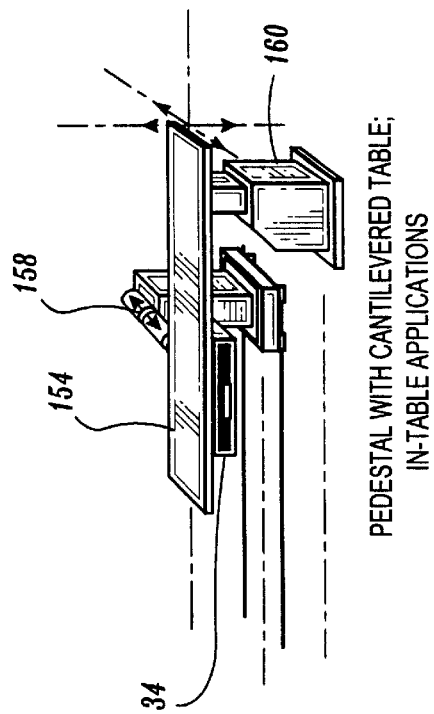

FIGS. 13 through 27 illustrate another embodiment. The articulated structure supporting detector 34 in this embodiment comprises a main support 102 (FIGS. 26 and 27) that typically is floor-mounted but can be mounted on a moving platform or on some other support such as wall. A telescoping sleeve 104 rides up and down on support 102. A column 106 is pivotally mounted on sleeve 104 to pivot about a horizontal axis, and an arm 108 is pivotally mounted on column 106 to ride along its length and to pivot about a horizontal axis. A support 10 extends from arm 108 and another arm 112 is pivotally secured to support 110 at a pivot axis 114 (FIG. 27). Detector 34 is secured to the other end of arm 112, to pivot about an axis 116 normal to the detector's imaging surface. Suitable brakes, clutches, locks , detents and/or counterweights are provided to facilitate positioning detector 34 for a multiplicity of x-ray protocols, either by moving some or all of the articulated structure by hand or by motorizing some or all of the motions. Some of the positions of detector 34 are illustrated in FIGS. 13–27 but it should be apparent that many more positions are possible with this articulated support arrangement. A patient table 120 (FIGS. 13–15) is mounted on two cross-members 122, 124 supported on respective sleeves 126, 128 that can telescope up and down on respective main supports 130, 132. In this manner, table 120 can move up and down (see difference between FIGS. 14 and 15) and can tilt, e.g. to move out of the way for a chest x-ray of a standing patient (see difference between FIGS. 13 and 14). This embodiment can thus be used with or without the patient table and its supports, for a multiplicity of x-ray protocols for standing, sitting or recumbent patients.

Yet another embodiment is illustrated in FIGS. 28–37. In this embodiment, the articulated structure supporting detector 34 comprises a main support 150 mounted on rails 152 for motion along the rails toward and away from patient table 154. A vertically telescoping column, generally illustrated at 156, moves up and down an arm 158 having one end mounted thereon for rotation about the vertical central axis of column 156. Detector 34 is mounted at the other end of arm 158 to rotate at least about an axis parallel to its imaging surface, so that detector 34 can rotate between horizontal and vertical orientations (compare FIGS. 28 and 29). Preferably, detector 34 is mounted on arm 158 for rotation about an additional axis as well, normal to the imaging surface, for changing between portrait and landscape orientations or for other purposes. In this embodiment, patient table 154 is mounted on a telescoping support generally illustrated at 160. Table 154 moves up and down by the telescoping motion of column 160 (compare FIGS. 32 and 33), and rotates about a vertical axis (compare FIGS. 28 and 29). In addition, arm 158 can be made to telescope (FIGS. 36–38) to further facilitate the positioning of detector 34 for different x-ray protocols for standing, sitting and recumbent patients. Only some of these positions are illustrated in FIGS. 28–38, for use with an independently mounted x-ray source.

Figure 41:
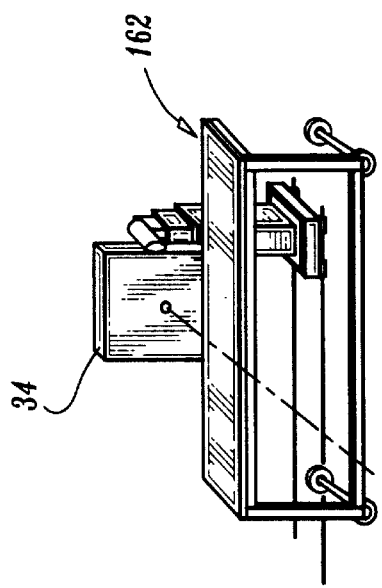
FIGS. 39–41 illustrate a further embodiment.
Figure 39:
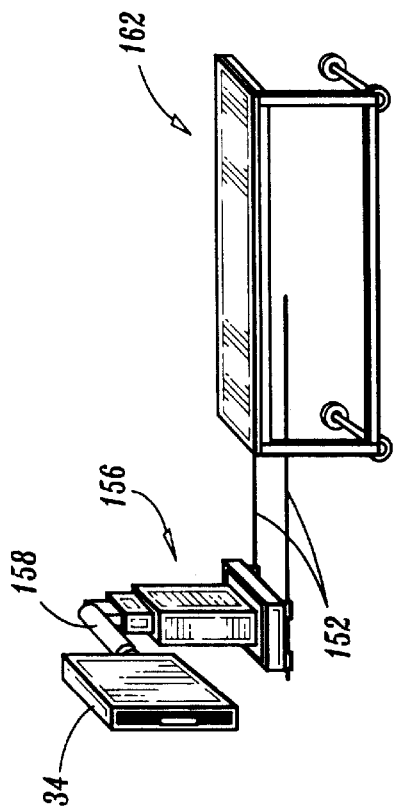
Figure 40:
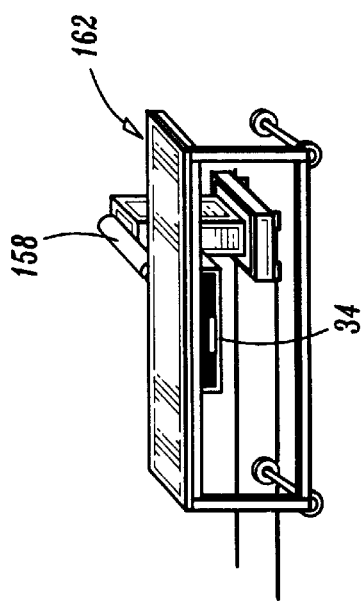
Figure 42:
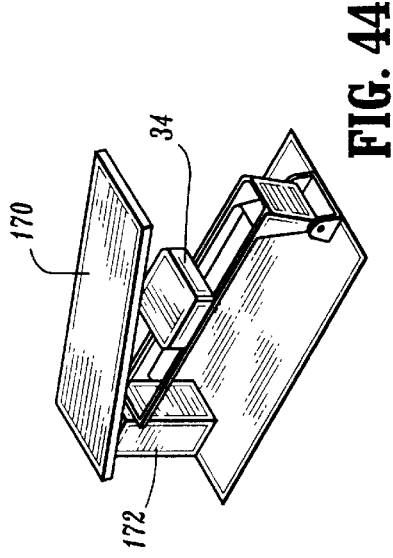
Figure 44:
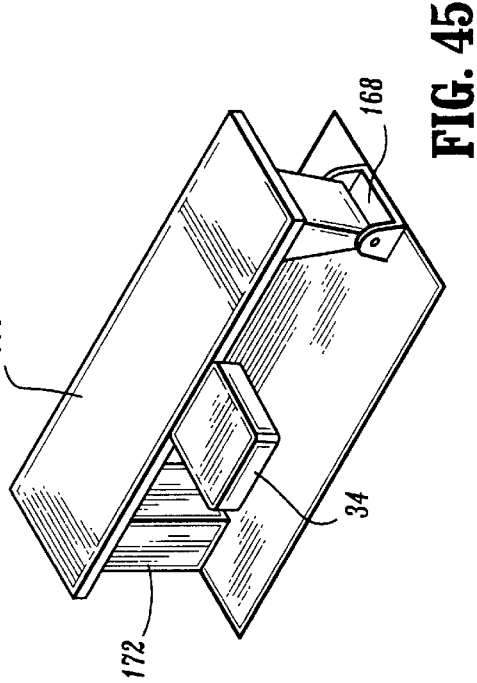
Figure 43:
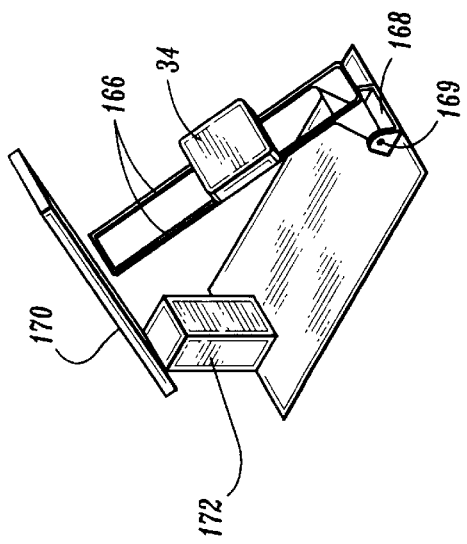

As illustrated in FIGS. 39–41, the articulated support for detector 34 can be used for x-ray protocols that do not call for a patient table such as table 154. In FIGS. 39–41, a gurney 162 supports the patients and is wheeled to the support for detector 34 that can be on rails 152. Detector 34 in this embodiment can be positioned as illustrated in FIGS. 39–42 or in other positions, some of which are illustrated in connection with FIGS. 28–38, for a multiplicity of standard x-ray protocols.

Figure 45:
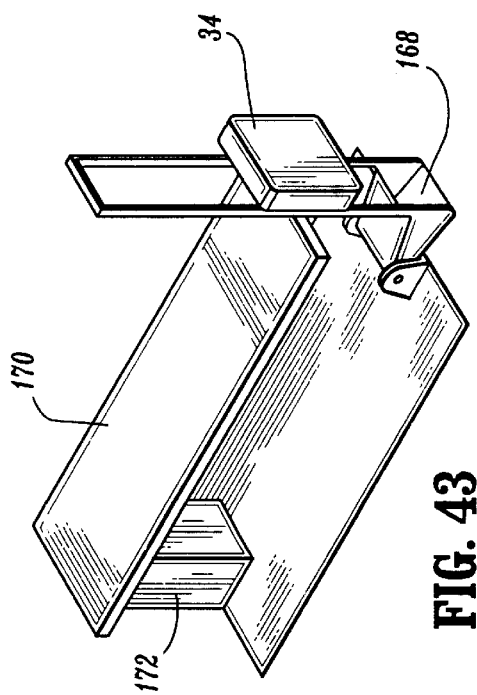

Yet another embodiment is illustrated in FIGS. 42–45. In this embodiment, detector 34 is mounted for motion along and across rails 166 that are mounted on a support 168 and pivot about a horizontal axis at 169, between a horizontal and vertical orientations of detector 34 (compare FIGS. 42 and 43). Patient table 170 is mounted on a support to pivot about an axis parallel to axis 169, at least between the positions illustrated in FIGS. 42 and 43. Detector 34 can slide across the length of rails 166, between the positions illustrated in FIGS. 44 and 45, on another set of rails (not shown). In this manner, detector 34 can be used for a variety of protocols, including but not limited to x-rays of a standing patient or a patient on a wheelchair (FIG. 43), a patient recumbent on table 170 (with detector 34 under the table), and for a body part extending to the side of table 170 (FIG. 45).

Another embodiment for positioning detector 34 relative to a patient bed is illustrated in FIGS. 46–50. In this embodiment, detector 34 is secured to a patient platform 180 mounted at 182 for pivoting about a horizontal axis at least between the positions of FIGS. 48 and 49. A counterweight 184 facilitates the pivoting motion. Detector 34 is secured to platform 180 through rails (not shown) extending along the length of the platform, and rails (not shown) extending across the length of the platform, for sliding motion along each set of rails. In this manner, detector 34 can slide along the length of platform, under the platform so a patient recumbent on the platform can be x-rayed with an independently supported x-ray source, such as ceiling-supported source. In addition, detector 34 can slide across the length of platform 180 so it clears the platform (in top plan view) and in that position can pivot about an axis at its edge closer to the platform to assume a vertical orientation, e.g. as illustrated in FIG. 46. In the upright position of patient platform 180, the patient can stand on a support 185 that can be made to move up and down the upright platform 180, for example by motorizing the motion. While detector 34 is not illustrated in FIGS. 48 and 49, it should be apparent that it is at the side of platform opposite the patient.

Figure 53:
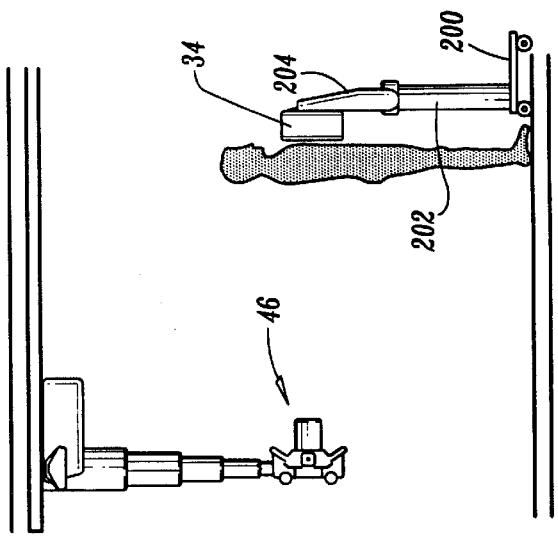
FIGS. 51–53 illustrate a further embodiment.
Figure 52:
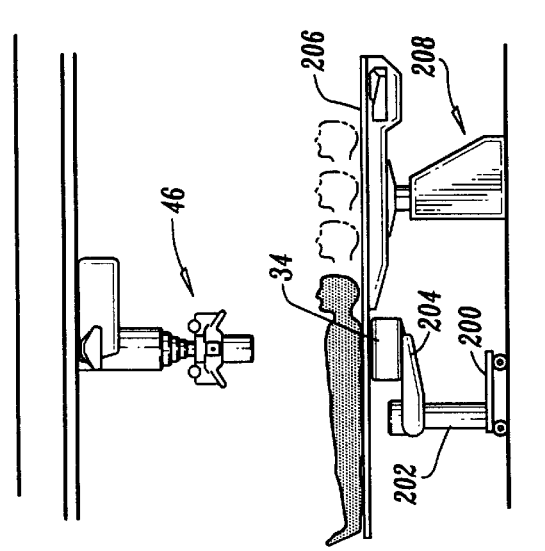
Figure 51:
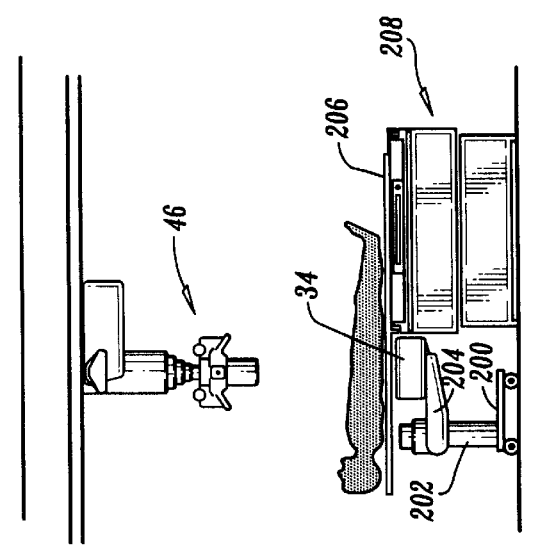

Detector 34 can be on a rolling articulated support structure, as illustrated in FIGS. 51–53. In this embodiment, a wheeled platform 200 supports a vertical column 202 that in turn supports an arm 204 movable up and down column 202 (compare FIGS. 51 and 52) and pivoting about a horizontal axis (compare FIGS. 52 and 53). The rolling structure can be used with a patient bed 208 that can move up and down on its telescoping support 208 (compare FIGS. 51 and 52) and along its length (see different positions of bed 206 illustrated in FIG. 52). The detector support structure can be used without a patient bed, for example for a chest x-ray of a standing patient, as illustrated in FIG. 53, or for a number of other x-ray protocols. A standard x-ray source 46 can be used.

In yet another embodiment, illustrated in FIGS. 54–59, detector 34 can be supported on structure generally indicated at 250 that in turn is supported for sliding motion along the length of a patient table 252 (compare FIGS. 54 and 55) and for rotation about a horizontal axis transverse to the length of table 252 (compare FIGS. 54 and 55a). Table 252 is in turn mounted on a vertically telescoping pedestal 254 that is on a rolling platform 256. As seen in FIG. 56, detector 34 is mounted on an arm 258 articulated at 260 for rotation about an axis normal to the imaging surface of detector 34 to allow the detector to move between the two illustrated positions, one under patient table 252 and one to the side of the patient table. In addition, as seen in FIG. 57, arm 258 can rotate about an axis parallel to one of its sides, to a vertical orientation, and can slide along the length of support 250 to position detector at different points along the length of patient table 252. FIGS. 58 and 59 illustrate the mounting of arm 258 for rotation about the two axis of interest. In addition, detector 34 can be mounted on arm 250 for rotation between portrait and landscape orientations.

The system as described can be enhanced in a variety of other ways to improve functionality and to take advantage of the flexibility of the digital image generation.

When using x-ray film, the sharpest images typically occur when the patient is positioned as close as practical to the film. This protocol also avoids object magnification and the file has a 1:1 image and so geometric distances can be easily measured. In a digital image, there is no requirement that the image be 1:1 to the object. Display monitors come in a variety of sizes. In a digital image, the pixel size in the object plane can be calculated, and distances on the image can be thus calibrated. In addition, the optimum object-imaging detector distance (OID) for a digital detector is different than that for film. For film, the OID that maximizes object sharpness in the object plane is 0, i.e. the object plane is as close to the film as practical. In a digital detector, the optimum distance can be where the combined effective system resolution, in the object plane, due to the focal spot blur and the pixel size is a minima. This occurs for non-zero OID, and in a flat panel system with a pixel size of 139 microns and a x-ray tube focal spot size of 0.5 mm, the optimum OID is roughly 7 cm.

The calibration of the pixel size in the object plane depends on the magnification factor, which is a function of both the source-imaging detector distance (SID) and the OID. Once the magnification factor is determined, the effective pixel size is known, and the magnification factor [M=SID/(SID-OID)] and/or pixel size can be inserted into the patient record, for example in the appropriate fields in the DICOM header. The display workstation software can use or display the information to establish a metric for the pixel size. Alternatively, the image could be remapped into one where the pixel size had a magnification factor of 1; this is useful in situations where the image is printed on hardcopy and manual measuring means are used. The determination of the magnification factor requires knowing the SID and the OID. One method is to measure the SID and OID. In one embodiment of this, encoders or sensors (not illustrated) can determine the SID and OID. In another embodiment, the SID and OID can be inferred from the acquisition protocol, for example in a standing chest image, the SID might be known to be 72 inches. In yet another embodiment, image processing of the acquired image might allow the determination of the magnification factor, such as though the measurement of a known fiducial phantom in the field of view, or through direct analysis of the acquired image.

The acquisition parameters such as x-ray tube voltage kVp and power mAs and knowledge of the SID and/or OID can be used to estimate the patient entrance dose. In a preferred embodiment of the system, this dose information is inserted into the patient record or DICOM header.

The fact that in a digital flat plate system the optimum OID is non-zero implies that means to keep the object being imaged at the optimum OID is a useful addition to a digital radiographic system. One embodiment of this would be a radiolucent frame (not shown in the drawings) that prevented the patient from being imaged closer than some predetermined distance.

Because the detector 34 vertical position can be positioned independently of the patient bed's vertical position, a situation where the detector is positioned under the bed allows the possibility that the detector might erroneously be a considerable distance under the bed. This could happen if the bed were raised without raising the detector through a corresponding vertical distance. Thus, a system to prevent or alert the operator to this improper situation would be useful. In one embodiment of this, an encoder or sensor (not shown) determines the distance from the detector to the bed. This distance determination can be used to automatically move the detector into the desired distance from the bed, or alert the operator of the improper position so as to avoid unnecessary exposure, or prevent exposure through an interlock until the detector is properly positioned. In another embodiment, the detector mechanically locks into the bed frame, so it would move vertically along with the patient bed.

As described in one preferred embodiment, the detector can be rotated from portrait to landscape orientation, especially useful for non-square panels, or rotated by 45° or some other angle to align the diagonal of the panel to a long object being imaged. In situations where the detector can be rotated, it is useful for the control system to know the orientation of the panel. This allows the determination of up and down, left and right on the image. One method of determining the detector orientation is through the use of encoders or sensors (not shown in the figures) that measure the detector orientation, and transmit this information into the control system. Once determined, this information can be used in a variety of ways. The orientation information can be inserted in the patient record or DICOM header file on the coordinate system of the acquired image. This information could be printed on the image itself. This information can also be used to control the automatic collimation of the x-ray source, to minimize radiation exposure to the patient areas not imaged on the detector. This information can additionally be used to reorient the image into a standard display format. For example, if an image of a hand was acquired with the bones of the fingers aligned horizontally, but the radiologists preferred seeing hand images with fingers aligned vertically, the software can determine from the detector orientation that the image needed to be rotated by 90° before storage or display.

In a variant of the above that does not require the measurement of the detector orientation, the image can be computer-analyzed and the orientation of the imaged body part determined through image processing means. The image can then be rotated before storage or display to present the body part in a standard orientation.

The determination of the orientation of the detector relative to the x-ray source is useful for other reasons. X-ray sources have an emission pattern that is non-uniform. In particular, the so-called heel effect causes the energy and flux to vary depending upon the relative angle of the detector to the anode. In film-screen imaging, the anode is positioned relative to the body so as to minimize this effect- the high-output side of the x-ray tube is positioned over the thicker body parts, if possible, so as to produce a more uniform illumination on the film. In a digital image, the heel effect can be corrected. In one embodiment of this, the orientation of the detector relative to the x-ray source is used to correct the acquired image for the non-uniformity due to the heel effect. The heel effect non-uniformity can be calculated, measured in previous calibration procedures, or estimated from the image using image-processing means.

The use of an anti-scatter grid is another reason to measure the orientation of the detector and anti-scatter grid relative to the x-ray source. Anti-scatter grids are often made of thin strips (laminae) of radio-opaque material, such as lead separated by more-or-less radiolucent spacer materials. These grids often shadow the detector with a non-uniform absorption of the incident radiation, causing image non-uniformity. This non-uniformity often has a geometrical orientation to it, and may be more pronounced along a given axis. The intensity of the non-uniformity is also dependent upon the SID. In a preferred embodiment of the system, the image to be corrected to undo the effect of the modulation non-uniformity. In one embodiment of the correction method, the system uses sensors to determine the orientation of the grid relative to the detector. This information is used, along with a model of the grid behavior, to estimate the effect of the grid on the acquired image and to eliminate it. Sensors or other means of measuring the SID are used to change the intensity of the non-uniformity correction. If the grid can be removed from the system, microswitches or other sensor means can be used to disable the grid cutoff correction if the anti-scatter grid is not present, and enable it when the grid is present.

Another embodiment of the anti-scatter grid correction method involves separate previously-performed calibrations of the anti-scatter grid's effect on image non-uniformity. These calibrations can involve imaging the detector with the anti-scatter grid in various orientations and at different SID and storing these calibration tables for use in the correction algorithm. Depending on the presence and orientation of the anti-scatter grid to the detector, and the orientation and distance of the x-ray source to the detector and grid assembly, the appropriate calibration table can be accessed and used to correct the image.

In another embodiment of the invention, sensor means determine not only the presence and orientation of the anti-scatter grid, but also determine the type of grid installed. This is useful for installations where different types of anti-scatter grids are employed. The image correction methods can correct for the characteristics of the specific grid employed.

The sensor signal indicating the presence or absence of the anti-scatter grid can also be used to alert the user, or prevent x-ray exposure, in situations where the protocol specifies the use or absence of a grid, and the system determines that the actual grid status is in conflict with the desired grid status.

Still another embodiment of the anti-scatter grid correction method involves an image processing means. Computer analysis of the image can be used to extract out the slowly-varying non-uniformity caused by the anti-scatter grid and to correct for it. The heel effect can be analyzed and corrected similarly.

The anti-scatter grid and the detector do not have to maintain a specified orientation relative to each other. There are situations where the grid would be preferentially rotated 90° or other angle relative to the detector, to allow independent alignment of the grid and detector. The system as described in this patent specification can allow this possibility. Sensors, encoders, or switches can be used to measure these parameters, and the system can utilize this information for control and correction means.

Under certain imaging protocols, the detector and x-ray source are tilted relative to each other, so that the central axis of the x-ray source is not normal to the surface of the detector. If the anti-scatter grid's laminae are not properly oriented with respect to the x-ray source, well-known imaging artifacts and severe grid cutoffs can occur in the acquired image. This can render the image unusable, and the patient is exposed to radiation for no positive purpose. The above described sensors and measuring means to determine the presence or absence of the anti-scatter grid, and the grid's orientation relative to the x-ray source can be used by the control system to determine if the detector is improperly oriented. In this case, the x-ray exposure can be prevented using interlock means, or a warning can be presented to the operator.

In another preferred embodiment, the x-ray source can be moved into the correct orientation and SID relative to the detector, depending upon the protocol chosen by the operator. The detector is moved by hand to the desired location. The position and orientation of the detector are determined by sensor or encoder means, and then with motors and encoder means the x-ray source is moved to the corresponding correct location relative to the detector. In another embodiment, both the x-ray source and the detector move automatically under motor control to the correct positions for the procedure, which was previously selected by the operator. Sufficient collision avoidance and collision detection mechanisms provide safety for personnel and for equipment.

The position and orientation of the x-ray source and detector can be determined through any of a number of well-known encoder and sensor technologies. One specific sensor embodiment that is particularly attractive can use wireless RF or electromagnetic tracking and digitizing systems, such as currently manufactured by Polhemus Corporation or Ascension Technology Corporation. These systems measure the position and orientation of sensors with 6 degrees of freedom.

Anti-scatter grids are often employed in radiographic imaging to reduce the image-degrading character of scattered radiation on the image. Stationary anti-scatter grids can cause well-known moiré pattern artifacts that are especially troublesome in a digital detector. Several embodiments of the system disclosed in this patent specification provide for the reduction or correction of moiré patterns. One embodiment employs a mechanical means to reciprocate or move the grid relative to the detector, during the exposure, to blur out the moiré pattern. This requires synchronizing the grid motion to the exposure signal. Reciprocating grid assemblies can be expensive, and can cause unwanted vibration, so methods of reducing the moiré pattern without grid motion are especially attractive. One embodiment for stationary grids employs image processing means to remove the periodic pattern caused by the beating of the spatial frequency of the scatter grid with the spatial frequency of the pixel size repetition. This algorithm can utilize the grid sensors previously described to determine the type of grid employed, and its orientation relative to the detector.

Other embodiments reduce the moiré pattern through selective design of the anti-scatter grid. It is known, for example, that moiré patterns do not occur or are suppressed in a system where the detector pixel pitch has a period exactly 1:1 (or an integral multiple thereof) to the period of the anti-scatter grid pitch. One difficulty with such a design is that it is requires the manufacture of a grid with extremely precise dimensions, otherwise a pattern will still occur. Anti-scatter grids are composed of alternating laminae and spacers, and different batches of spacers or laminae, for example, might have slightly different dimensions. If an anti-scatter grid is manufactured with a period P slightly smaller than the detector pixel pitch D ($D=P+\epsilon$, where $\epsilon$ is small compared to P), then the reduction of moiré pattern will occur when this grid is mounted a small distance above the detector front surface, the optimal distance depending upon the relative dimensions of the pixel periodicity and the grid periodicity. This moiré pattern reduction would also work for grids and detector periods having relationship $D=NP+\epsilon$, with N an integer. In another preferred embodiment, the detector housing can allow the mechanical mounting of the grid a small, but adjustable, distance above the plate. See FIG. 60 for a schematic illustrating this. During system calibration, the optimum distance is determined, and the mounting mechanism adjusted via shims or other means to position the grid the correct distance from the plate. Such a system can have a greater insensitivity to manufacturing tolerances of the grid and detector pixels.

Figure 60:
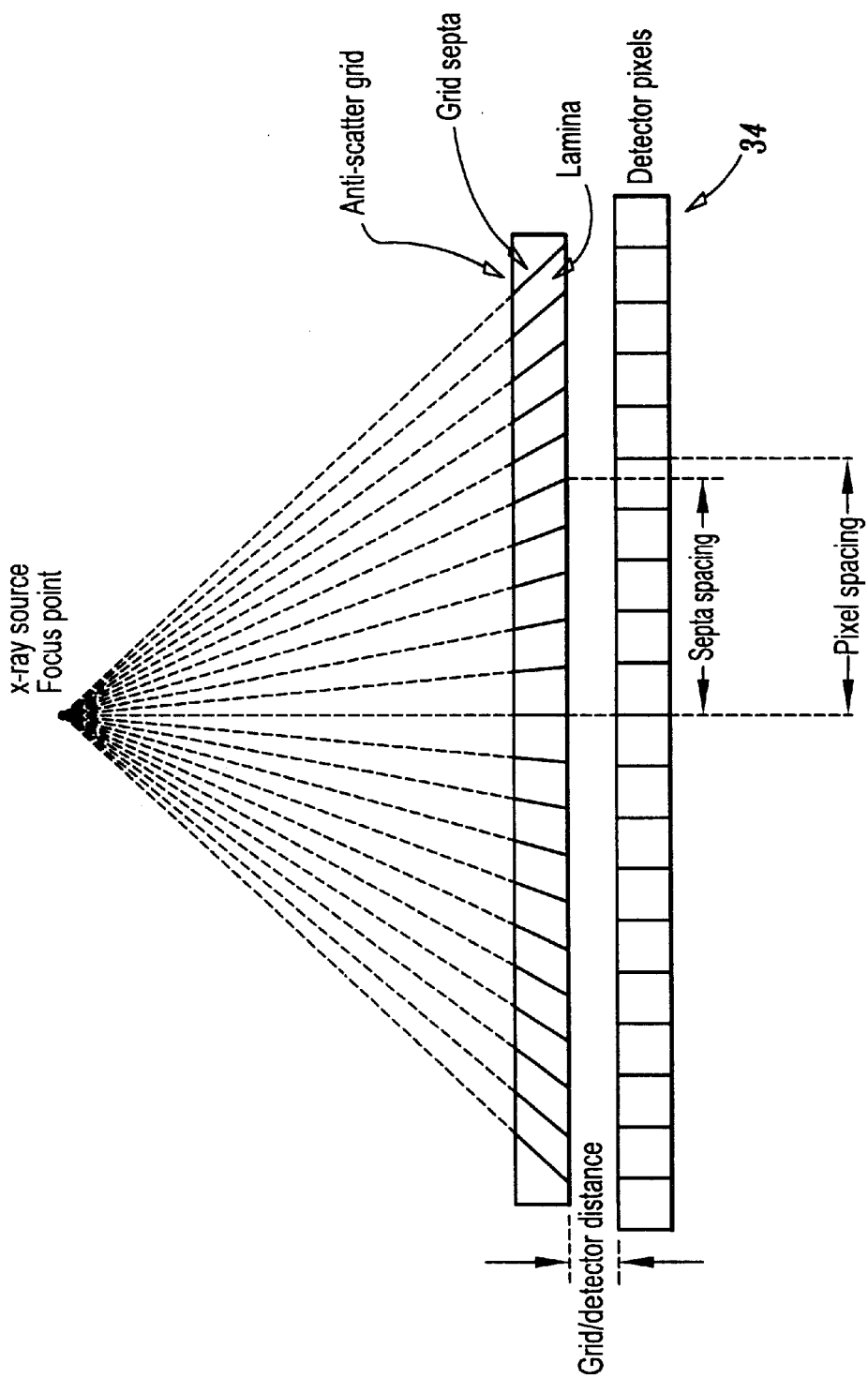
FIG. 60 illustrates a relationship between an anti-scatter grid and pixels of a flat panel digital x-ray detector.

FIG. 60 illustrates a focusing anti-scatter grid. In these grids, the pitch of the septa is different on the detector face relative to the object face. For these grids the relevant grid pitch that determines the moiré pattern is the pitch of the grid septa facing the detector.

Other system embodiments are desired or useful in a digital system. One preferred embodiment includes the capability of the system to perform a low-dose preview image prior to the final full-radiation image. In this procedure, the patient is positioned as desired, and a low-dose scout shot is performed. The resultant image is displayed, and is analyzed by the operator for proper positioning of the patient, detector, and x-ray tube. If the alignment is adequate, a second full-exposure image is acquired.

In some procedures the patient can cradle the image receptor, as with film. An example of this is a standing chest AP image, where the patient would desirably cradle his arms around the detector. Often the patient will also support his weight partially with the detector. To facilitate this, a preferred embodiment of the system will include handles on the detector housing, for patient gripping. If there are controls on the detector housing that could be touched by a patient, it is desirable to be able to disable these controls to prevent accidental engagement by the patient. For standing chest imaging where the patient is supporting his weight partly on the detector, sufficient braking resistance can be provided to prevent accidental detector motion. Imaging protocols on the bed can also benefit from patient handholds. An example would be images taken where the patient is standing on the bed. In some of the proposed embodiments, there is a vertical column that supports the detector, and patient handholds on this column can be useful for the above mentioned patient support reasons. Another use of the vertical column can be as a support stand for a display screen, useful for operator control use.

Another important design criteria for the system is to protect the detector from accidental entry of body fluids, blood, and other liquids that might be spilled. The entry of these liquids into sensitive electronics might be harmful to the system, and can present a cleaning challenge. In one preferred embodiment, the detector housing is designed for easy cleaning, such as with a flat front surface. The seam for the opening of the detector housing could be in the rear of the housing, away from the front surface. The flat front surface is easily cleaned, and the rearward mounted seam would be less likely to introduce liquid entry into the detector. The seam could be sealed with an o-ring to further discourage liquids. Simple draping of the detector housing in plastic might not be desirable, as it might interfere with cooling fans needed for the electronics. Practical designs for the detector housing should account for the heat generated by the electronics associated with the flat panel detector. Analog-digital converters, amplifiers, and other components often have undesirable temperature coefficients, and therefore the flat panel is optimally maintained at a given temperature. Thus, in a preferred embodiment, the detector housing can have means to maintain a stable temperature, or at least prevent the temperature from exceeding certain limits.

Other advantages of the digital flat panel arise from the digital nature of the image. In one preferred embodiment, the controlling computer system automatically keeps a log of system and operator performance. The system measures and stores a history of each exposure and its associated parameters, such as: exposure time, x-ray tube current and kV, source-detector and source-patient distances. The system also keeps a record of image retakes and the type of imaging protocol used. This database can be used to evaluate system and operator performance. In another embodiment, the system performs automatic quality control and calibration. For safety reasons, x-ray tube outputs need to be verified routinely by in-hospital physicists. This can prevent dangerous irradiation of patients by faulty equipment. A film system offers useful warning on x-ray malfunction, because the operator will notice that the film exposures are not optimal. A digital system has a greater dynamic range, and will tolerate a larger variation in x-ray output before a problem is noticed by image degradation. Therefore, a useful check of system performance is an algorithm that determines if the recorded image is in concert with the expected image based on tube voltage and currents. This analysis can be performed on images taken in a special quality control procedure, or on the routine patient images. Feedback to the user is provided when the system indicates a possible problem. Another preferred embodiment for quality control is a system that employs automated procedures that verify that the stored calibration files, such as pixel gain and offset, and bad pixel maps, are correct. This can include the system making exposures and testing the uniformity of a flood field. These calibrations can proceed essentially without user intervention, and can be performed on a routine basis automatically. In another preferred embodiment, the system can be controlled and accessed remotely, such as through a modem or network link, so that system debugging and maintenance can be offered by a service organization and provide faster service response without requiring a field service visit. In this system, the remote user would be able to access and analyze image and calibration files, and control the system to perform automatic tests.

In the system, the operator will control the exposure time and voltage, and determine the correct SID for the procedure, by selecting the desired protocol from a list containing the most commonly performed protocols. There are literally hundreds of possible protocols, and a convenient method of quickly accessing the desired one is useful. In a preferred embodiment, the set of acquisition protocols can be organized in a hierarchical folder arrangement. The hierarchy is most conveniently organized by body parts, with each lower level containing a list of more and more specific body regions. For example, the protocol AP Oblique of the Toes, is accessed through a folder selection like the following:

1. Lower limbs
2. Feet
3. Toes
4. AP Oblique.

Information on the acquisition protocol can also be automatically inserted into the patient record or DICOM header of the image file.

Currently, digital images have a greater dynamic range than that of the display device, and the image typically is processed before display to optimize its performance. The image contains areas of greatly varying x-ray exposure, from areas with little exposure directly under an attenuating body area to areas exposed to the direct x-ray beam with very large exposure. Preferably, the system will determine the location of the area of interest, and will adjust and map the image into one that optimizes the display of that area. In one preferred embodiment, the operator will indicate on the image the approximate region of the desired area for analysis, and the display will then be optimized to the exposure in that region. This system can take the form of a mouse-controlled cursor, which is used to click on or outline or otherwise define the area. In another preferred embodiment, the computer can use the knowledge of the protocol being employed and perform image analysis to locate the body part of interest and optimize the display of said part. For example, in an AP chest image, the display might optimize the display of the lungs, spine, or other organ depending on the image protocol. Preferably, information on the mapping transformation is stored or else both the original image and the remapped image are stored, so that the image can be reverted to the original or remapped with different parameters if so desired by the operator.

Yet another preferred embodiment refers to a convenient method for the operator to access the patient images that have been performed. Commonly, just a text listing of the studies is displayed on a computer screen, and the operator must read through the list to choose the desired images for display or transfer or storage. In this preferred system, a thumbnail image of the study is displayed next to the textual information. This provides a visual cue to the operator, facilitating the selection of the correct files. This patent specification incorporates by reference concurrently filed application Ser. No. 60/167,397 entitled Apparatus and Method for Correcting Image Non-uniformities in Diagnostic Radiology.

The following is the text of the "Detailed Description of Preferred Embodiments" of parent application Ser. No. 09/413,266, filed Oct. 6, 1999, which was allowed on Dec. 1, 2000 but is being merged with, and therefor abandoned in favor of, this application. FIGS. 1–10 of the parent application have been renumbered as FIGS. 61–70 of this application, and the reference numerals in the text from the parent application have been changed by adding the prefix 61 to each in the text below.

Figure 61:
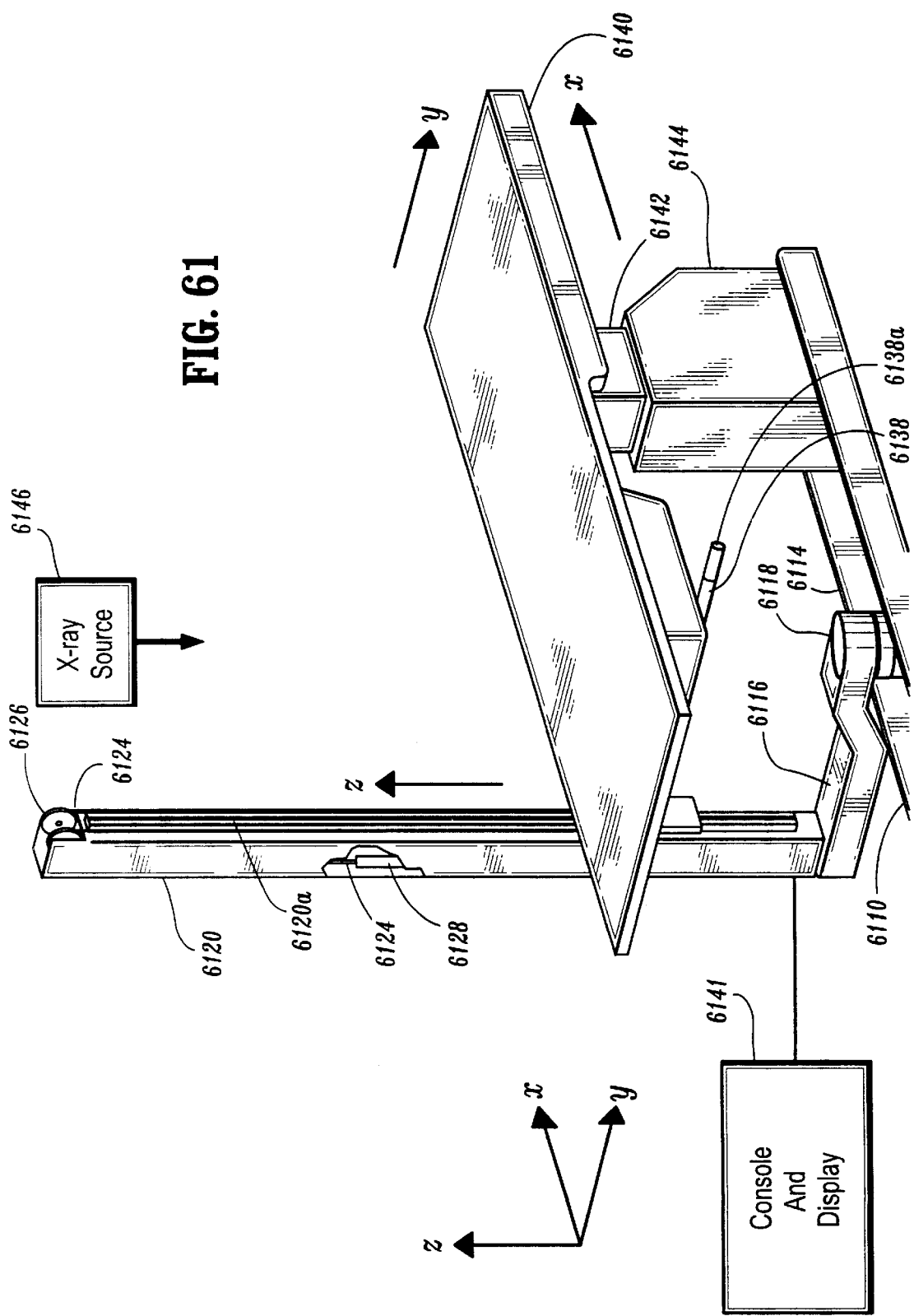
FIG. 61 illustrates a system for positioning a digital flat panel detector and a patient table, with the detector under the table, for example for an AP chest x-ray of a supine patient.

Referring to FIG. 61, a main support 6110 can be secured to the floor of a radiology room (or to a movable platform, not shown), and has a track 6112 (see FIG. 66) on which a horizontal slide 6114 rides for movement along an x-axis. Slide 6114 supports a generally horizontal lower arm 6116 through a bearing 6118 allowing rotation of arm 6116 about a z-axis. The distal end of arm 6116 in turn supports a column 6120 extending along the z-axis and having a vertical slot 6120a. A vertical slide 6122 (see FIG. 65) engages slot 6120a for vertical movement along the height of column 6120 and is supported by cables 6124 that reverse direction over pulleys 6126 and connect to counterweights 6128 riding vertically inside column 6120. Vertical slide 6122 in turn supports an upper arm 6130 through a bearing arrangement 6132 allowing rotation of upper arm 6130 about a horizontal axis extending along the length of arm 6130. Upper arm 6130 supports a cassette 6134 containing a flat panel detector of the type discussed in the U.S. patents cited above. Cassette 6134 can be connected to upper arm 6130 through a bearing arrangement 6136 to allow rotation of cassette 6134 about an axis normal to the x-ray receiving face of the flat panel detector. This can be desirable if the panel inside cassette 6134 is rectangular, to allow using it in portrait or landscape orientations, or if such rotation is desirable for other reasons. Alternatively, bearing arrangement 6136 can be omitted. A handle 6138 is attached to cassette 6134, when bearing 6136 is used, or can be attached directly to arm 6130 otherwise, and has a manual switch 6138a at its distal end that locks cassette 6134 in position or unlocks it to allow repositioning, or comprises several switches or other controls used for other purposes, such as to control motorized movements.

A patient table 6140 is supported on a telescoping column 6142 that moves table 6140 up and down, along the z-axis, within a guide 6144 secured to main support 6110. Table 6140 is made of a material that minimizes distortion of the spatial distribution of x-rays passing through it. If desired, table 6140 can be made movable along the x-axis, in a mainer similar to the bed in the QDR-4500 Acclaim system commercially available from the assignee of this patent specification, and/or can be made to tilt about one or both of the x-axis and the y-axis. A console and display unit schematically illustrated at 6141 can be connected by cable to cassette 6134 to supply power and control signals thereto and to receive digital image data therefrom (and possibly other information) for processing and display. The display at unit 6141 can be, for example, on a CRT or a flat panel display screen used in the usual manner. The usual image manipulation facilities can be provided at unit 6141, for example for level and window controls of the displayed digital x-ray image, for image magnification, etc. The cabling can be run through column 6120 and through bearing arrangement 6118 and lower arm 6116 to reduce interference with motion of slide 6114 along track 6112, rotation of arm 6116 about bearing 6118, and vertical motion of cassette 6134 along column 6120. Alternatively, cassette 6134 can be powered and controlled in some other way, and image data can be extracted therefrom in some other way. For example, cassette 6134 can be a self-contained cassette, with an internal power supply and with control switches on or in cassette 6134 can control its operation. Cassette 6134 can further contain storage for the data of one or more x-ray images. Image data can be taken out of cassette 6134 by way of a wireless connection, or by temporarily plugging in a cable therein when it is time to read image data.

For a chest AP image of a supine patient, table 6140 can be lowered to make it easier for the patient to get on. Of course, cassette 6134 that has to be in a position that allows table 6140 to be lowered. Otherwise, the operator trips switch 6138a to release cassette 6134, and moves it to the appropriate position manually, using handle 6138 to slide vertical slide 6122 up or down along column 6120. Alternatively, or in addition, the operator rotates lower arm 6116 about bearing 6118, for example to the position shown in FIG. 62 or FIG. 63. With the patient in the supine position, head at the left end of table 6140 as seen in FIG. 61, the operator can leave table 6140 at that position, or can move it up to a higher position. Table 6140 can be moved up or down by driving telescoping column 6142 with a motorized drive similar to that used in said QDR-4500 unit. Alternatively, another table elevating mechanism can be used. The operator then moves cassette 6134 to a position such as shown in FIG. 61, under table 6140, vertically aligned with the patient's chest. For that purpose, the operator trips switch 6138a to release cassette 6134, and manually moves cassette 6134 up or down column 6120 to the desired height, and can manually rotate lower arm 6116 about bearing 6118 and slide horizontal slide 6114 along track 6112. An x-ray source schematically illustrated at 6146 can be separate from the bed and detector system, and is aligned with and faces cassette 6134, and is energized in the usual way to produce the appropriate x-ray exposure at detector 6134. Source 6146 can be connected with console and display unit 6141 in the usual way, through cable or a wireless connection, to allow controlling x-ray source 6146 from unit 6141. Unit 6141 and x-ray source 6146 are not shown in the remaining figures, but it should be understood that they can be present there as well and are in the usual way for an x-ray exposure.

Figure 61A:
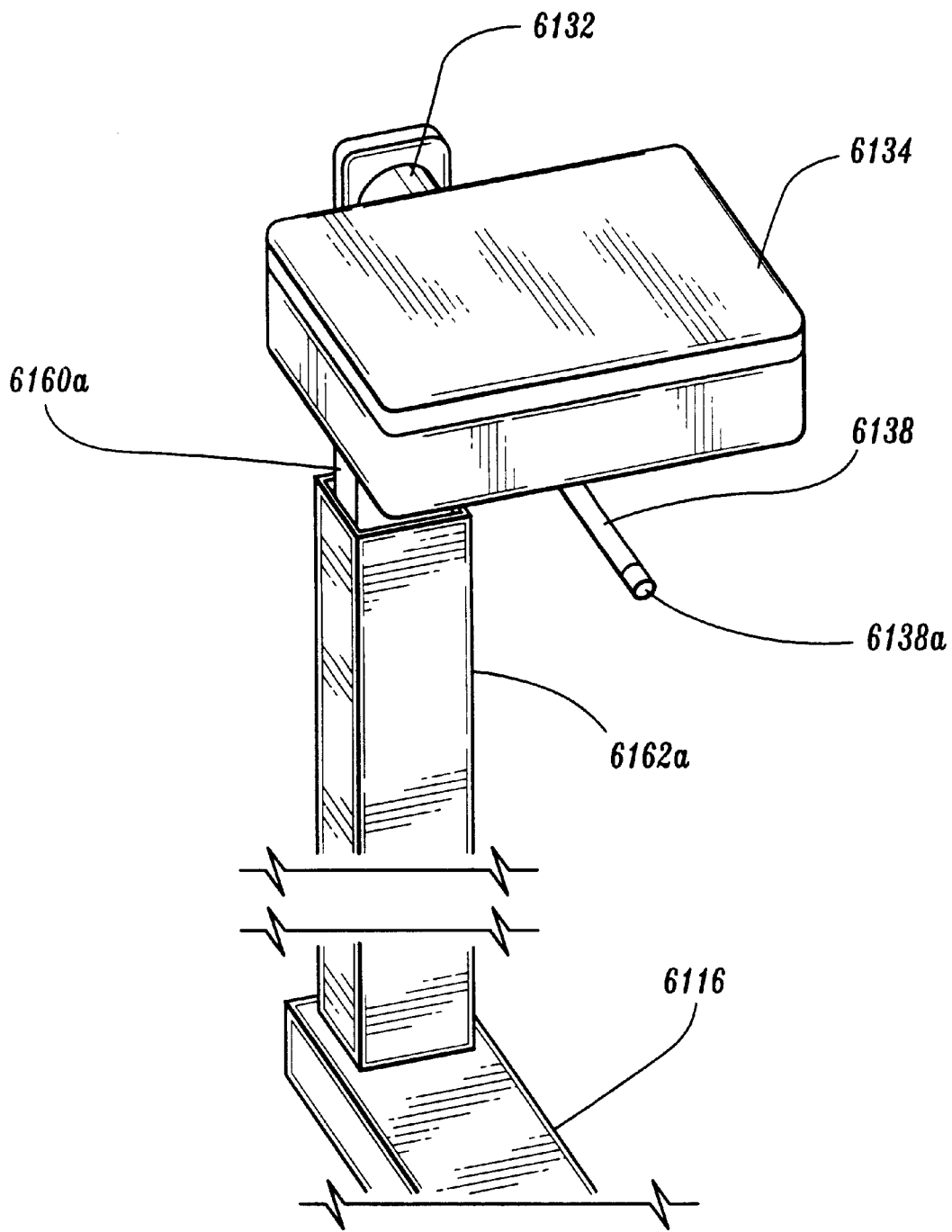
FIG. 61a illustrates a modification of the system of FIG. 61.

FIG. 61a illustrates a modification to implement a system that is otherwise the same or at least similar to the embodiment of FIG. 61 except for slide 6122 is secured to a telescoping column 6162a moving up and down in a guide 6160a instead of sliding along a column 6120 as in FIG. 61. In FIG. 61a, telescoping column 6162a carries slide 6122, and with it cassette 6134, up and down. This up and down movement can be done by hand or can be motorized, and can use counterweights or some other arrangement to make hand actuation easier, and can use lutches, brakes, etc. as for other movements discussed herein. In all other respect, the system of FIG. 61a is the same or at least similar to that of FIG. 61, although only a part of the system is illustrated in FIG. 61a.

Figure 62:
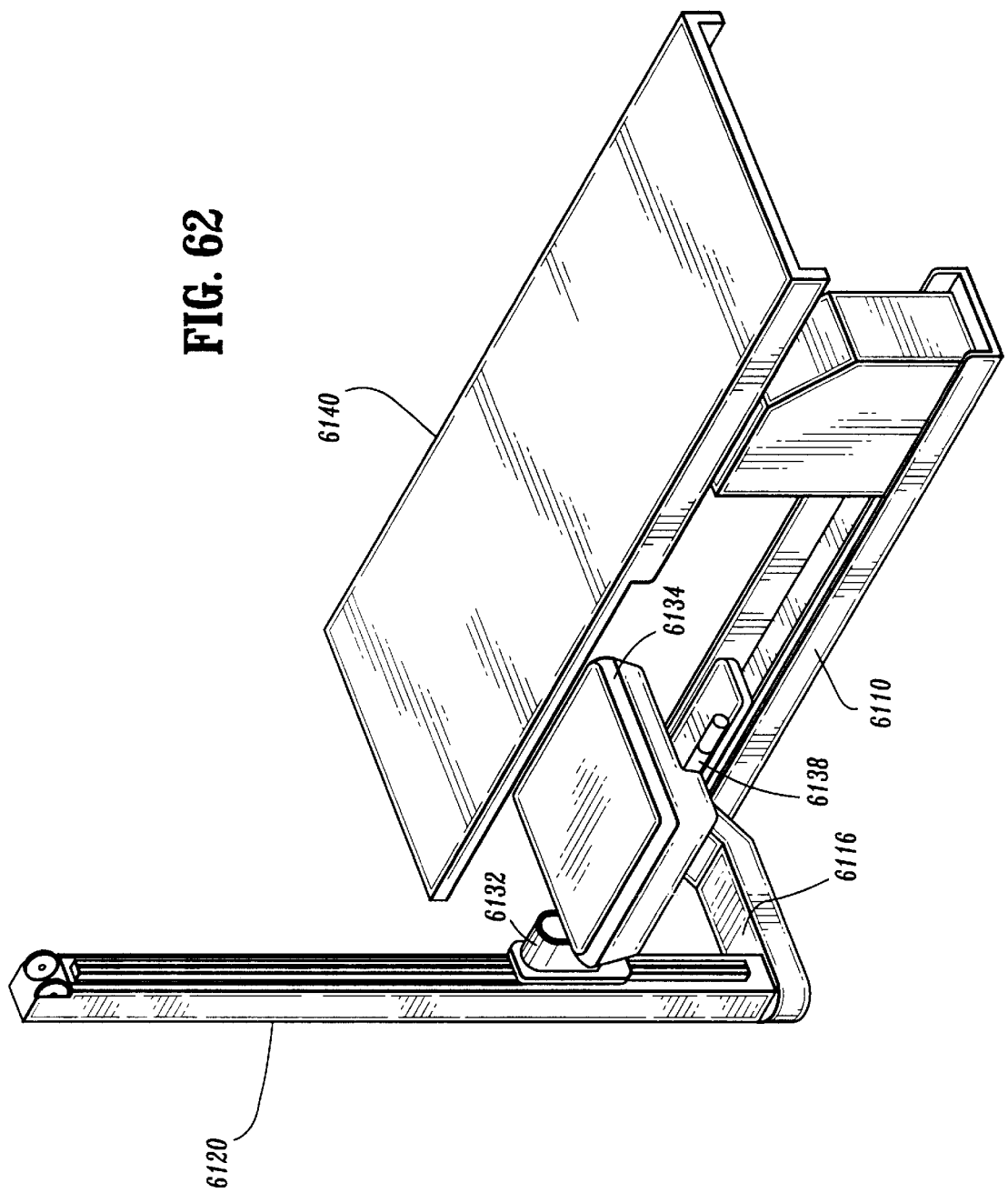
FIG. 62 is a similar illustration, showing the detector in a horizontal position adjacent a side of the patient table for example for imaging an extremity.

For imaging an arm or a hand, for example, cassette 6134 is positioned as illustrated in FIG. 62, by rotating lower arm 6116 about bearing 6118, moving cassette 6134 up or down along column 6120 and, if desired, sliding horizontal slide 6114 along track 6112 as earlier described. At the desired height of cassette 6134, and of table 6140 with the patient thereon, x-ray source 6146 is aligned and energized in the usual way for x-ray exposure.

Figure 63:
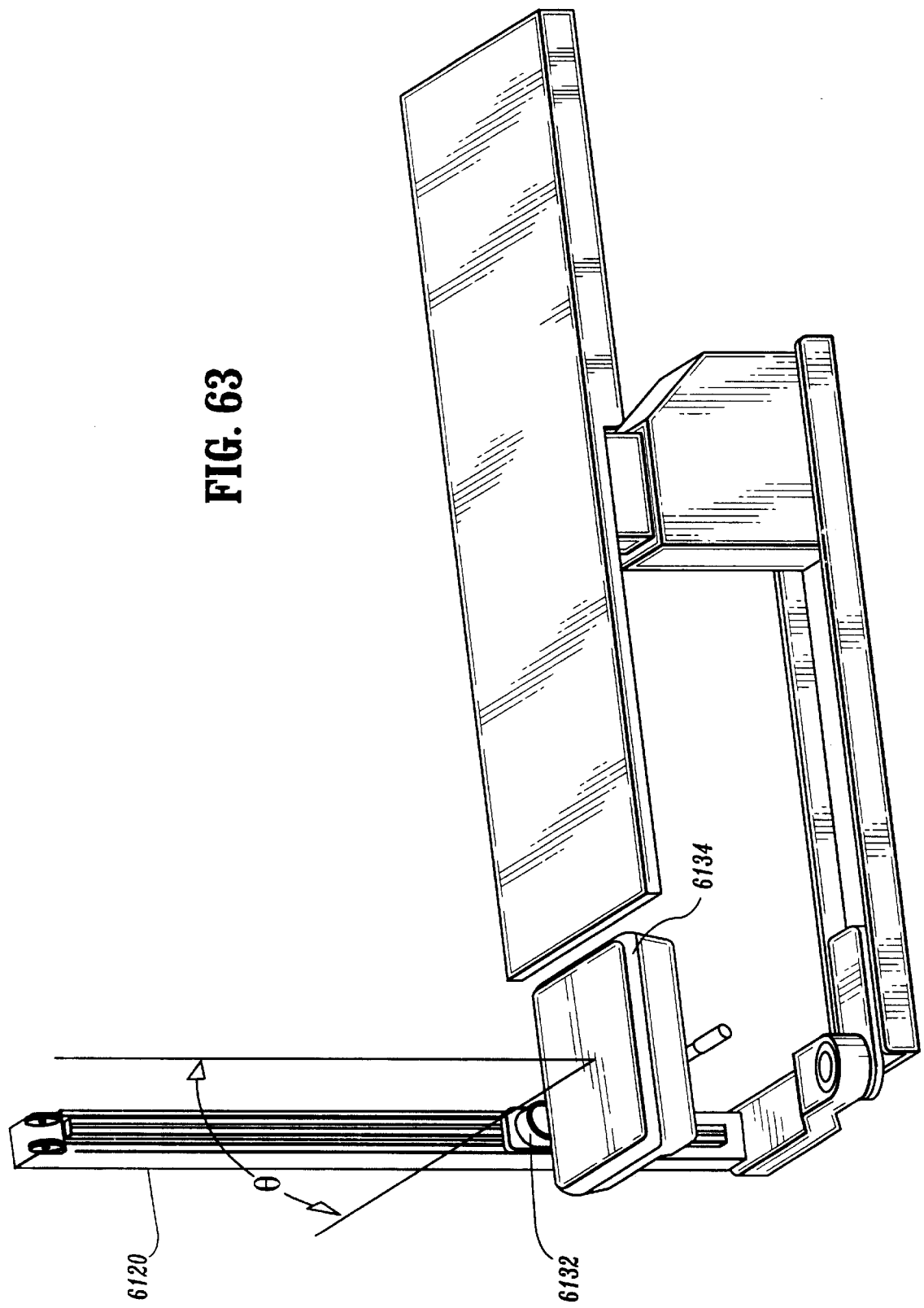
FIG. 63 is a similar illustration, showing the detector in a horizontal position but adjacent one of the ends of the patient table, for example for imaging a patient's head or feet.

For imaging the head or lower extremities of a patient, table 6140 and cassette 6134 can be positioned as illustrated in FIG. 63, moving one or both to the desired position using the motions described above, with the patient's head or, for example, foot, resting on cassette 6134. If desired, the operator can rotate cassette 6134 about an axis parallel to handle 6138 to incline cassette 6134, for example through an angle relative to the vertical, as illustrated in FIG. 63. X-ray source 6146 is aligned and energized the usual way.

Figure 64:
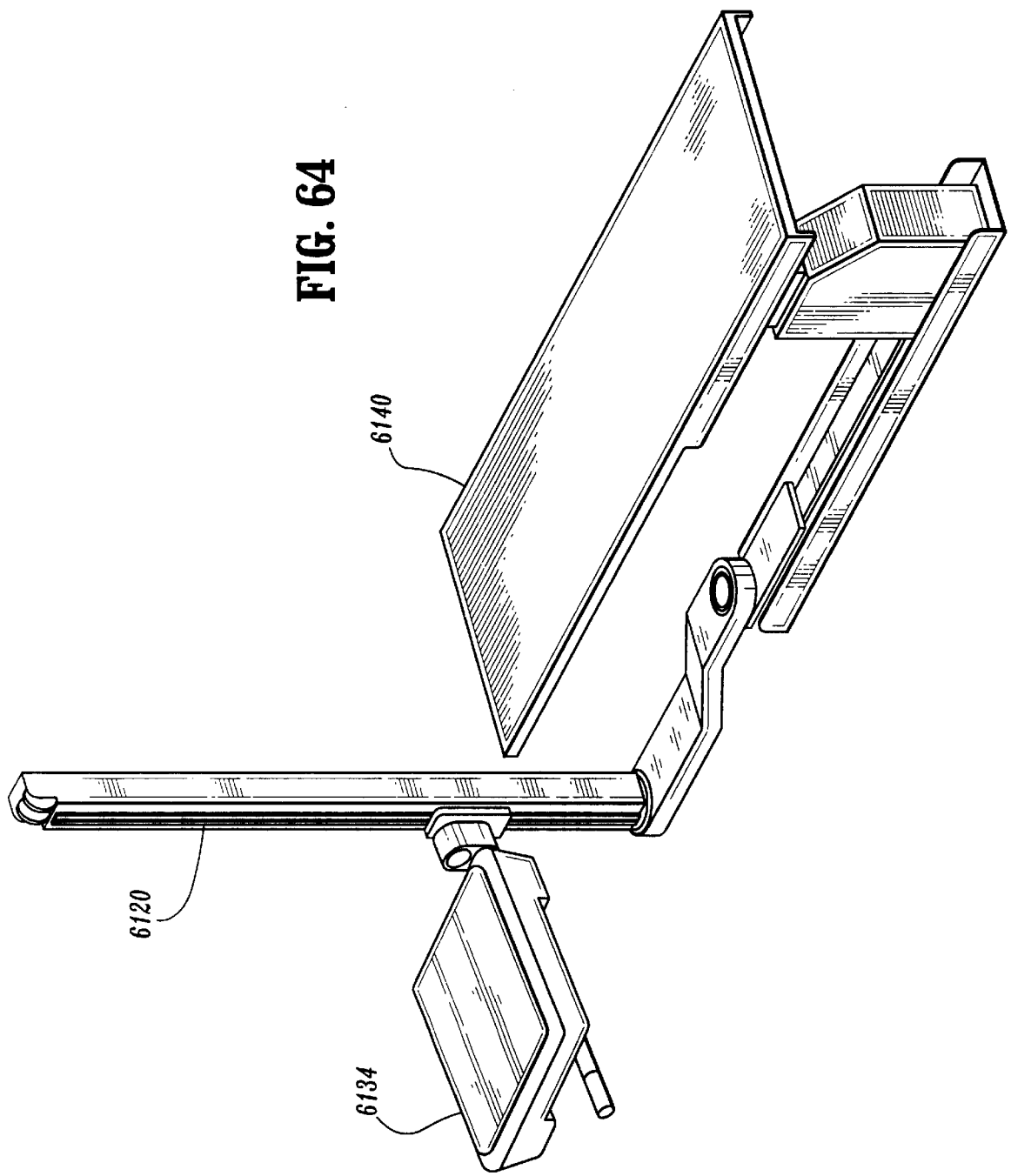
FIG. 64 is a similar illustration, showing the detector in a horizontal position, for example for imaging a patient in a wheelchair.

FIG. 64 illustrates cassette 6134 moved to a position away from patient table 6140, suitable for use with a patient in a wheelchair, for example. Cassette 6134 is positioned relative to the patient using some or all of the motions earlier described, and an x-ray exposure is taken.

Figure 65:
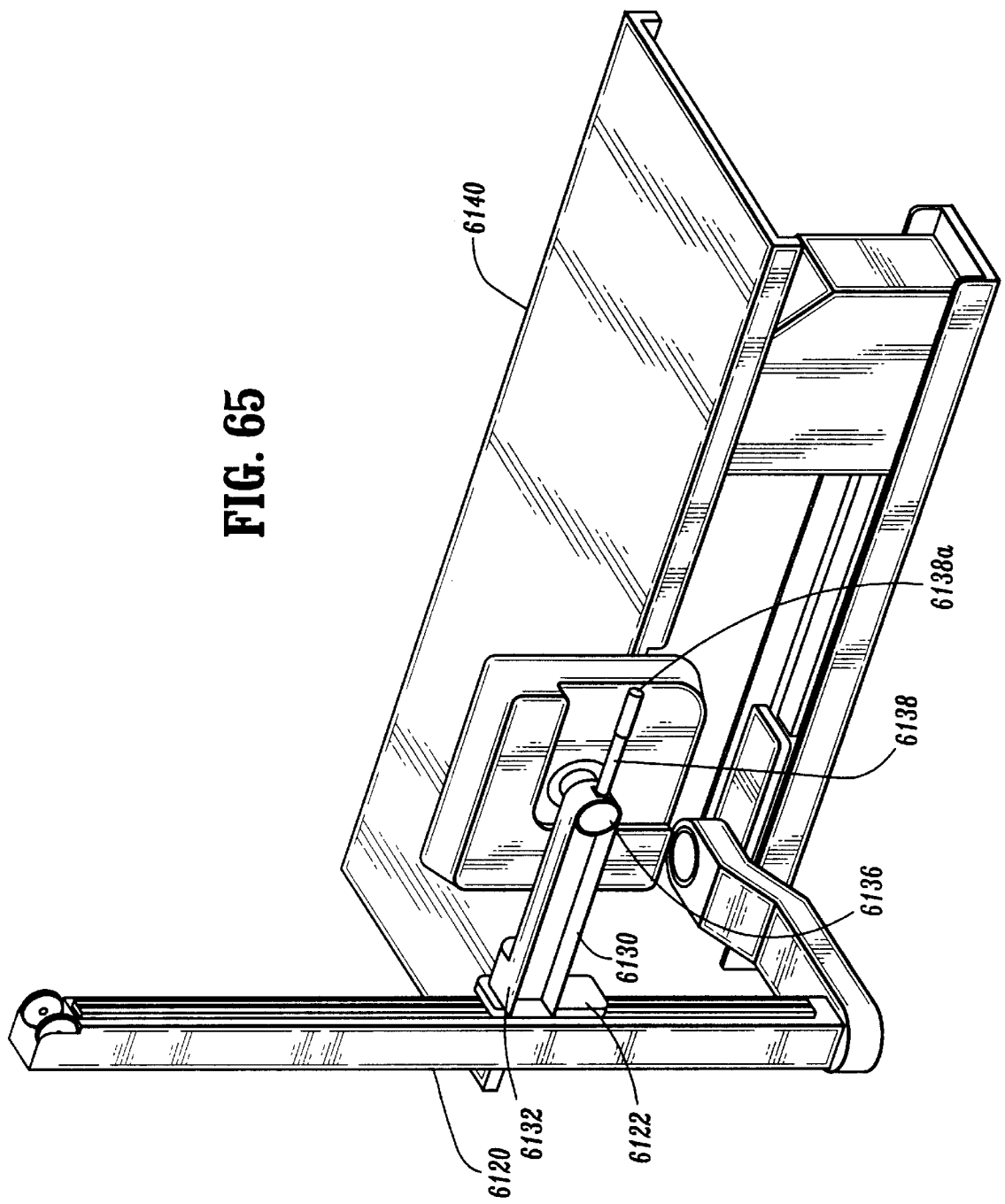
FIG. 65 is a similar illustration, showing the detector in a vertical position adjacent a side of the patient table, for example for cross-table lateral imaging.

In FIG. 65, cassette 6134 is oriented vertically, by releasing it through manual operation of switch 6138a and rotating about bearing 6132, in addition to some or all of the cassette and/or table motions earlier described. An x-ray source 6146 (not shown in this figure) faces cassette 6134 from across patient table 6140 and is aligned and energized in the usual manner for an exposure.

Figure 66:
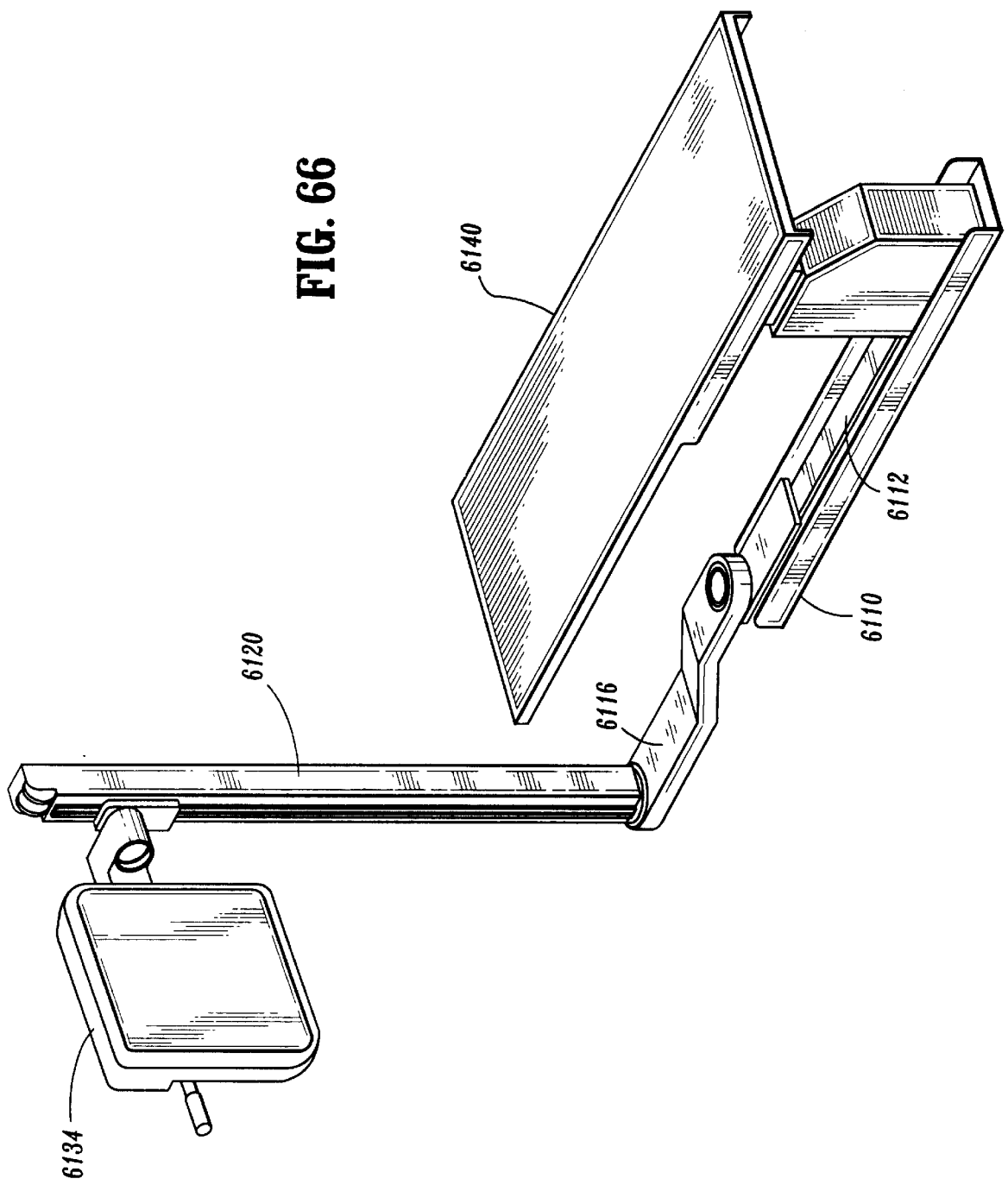
FIG. 66 is a similar illustration, showing the detector in a vertical position, for example for a chest x-ray of a standing patient.

FIG. 66 illustrates cassette 6134 in a vertical orientation, for example for an AP chest image of a standing patient. The operator moves cassette 6134 to the illustrated position using some or all of the motions earlier described to align cassette 6134 with the patient's chest. An x-ray source (not shown in this figure) that faces cassette 6134 from across the patient is aligned and energized in the usual way for an exposure.

Figure 67:
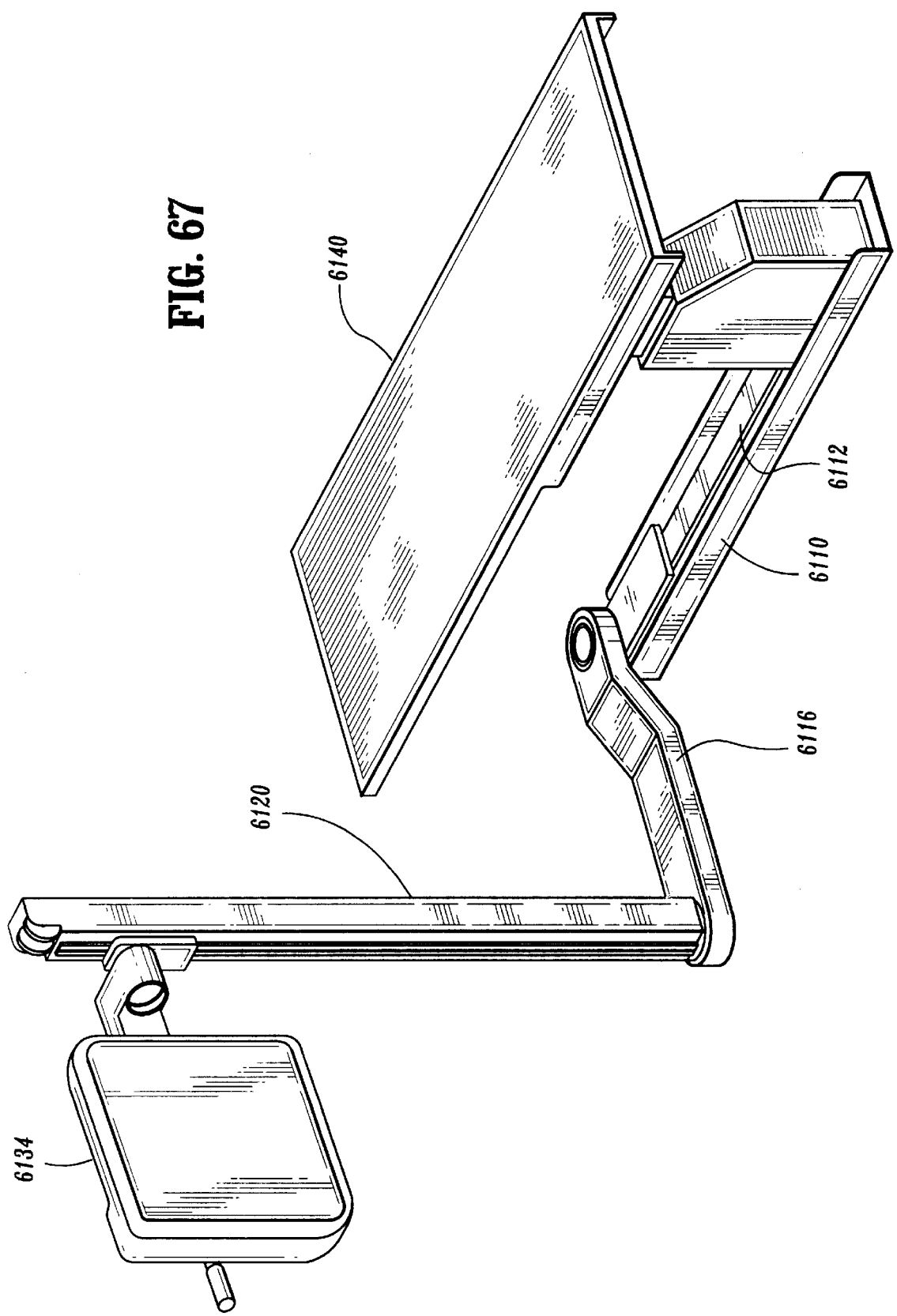
FIG. 67 is a similar illustration, showing the detector in a vertical position as in FIG. 66 but spaced further from the patient table.

FIG. 67 illustrates another position of cassette 6134 that can also be used for imaging the chest of a standing patient. It differs only in that, while in FIG. 66 lower arm 6116 extends along the same x-axis as track 6112, in FIG. 67 arm 6116 is normal to track 6112.

Figure 68:
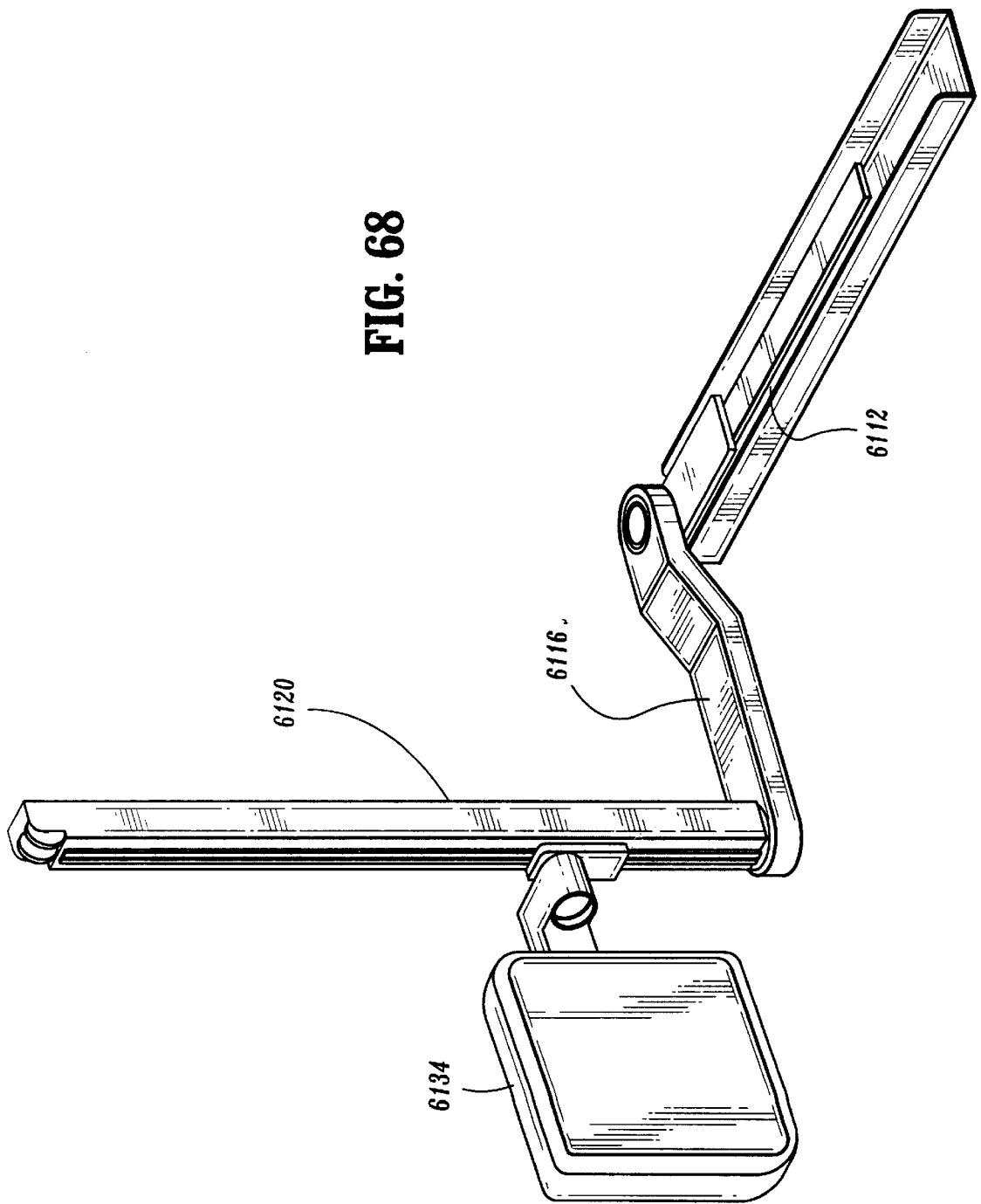
FIG. 68 is a similar illustration, showing the detector in a vertical position close to the floor, for example for imaging a lower extremity of a standing or sitting patient.

FIG. 68 illustrates cassette 6134 in a position suitable, for example, for imaging a lower extremity of a standing patient. Using some or all of the motions earlier described, the operator moves cassette 6134 to the illustrated position, aligned with the patient part to be imaged, and the suitably aligned x-ray source (not shown in this figure) is energized for an exposure. Patient table 6140 is not shown in FIG. 68. It may but need not, be present in all of the embodiments disclosed herein. For example, if there is no need to support a patient on a patient table, then table 6140 and its telescoping support 6142 and guide 6144 can be omitted, or can be offered only as an option to the arrangement shown in FIG. 68.

Figure 69:
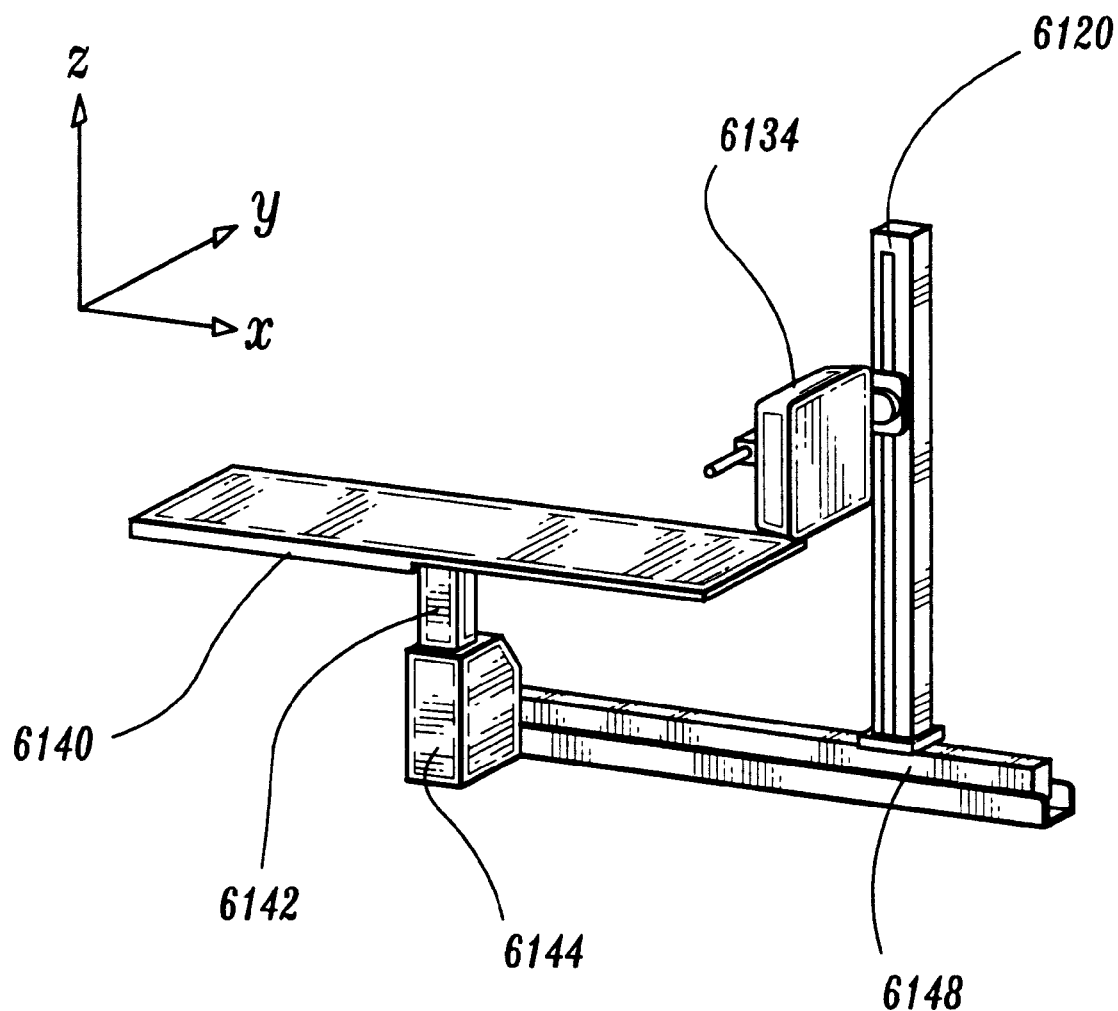
FIG. 69 illustrates another embodiment of such system.

FIG. 69 illustrates an alternative arrangement that differs from FIG. 61 in that a telescoping, horizontally extending rail 6148 secured to main support 6110 moves column 6120 along the x-axis, instead of using a horizontal slide 6114 riding on a track 6112 as in FIG. 61. Column 6120 can be moved in the y-direction using a sliding arrangement to permit it to move along the x-axis relative to rail 6148. Alternatively, rail 6148 can be pivotally mounted on support 6144 to allow it to pivot about the z-axis and thus move column 6120 in a direction transverse to the x-axis. Unit 6141 and x-ray source 6146 are not shown in FIG. 69 but can be present.

FIG. 70 illustrates yet another embodiment differing from FIG. 61 in that table 6140 is supported on two columns 6150 that could be telescoping for movement along the z-axis, and column 6120 is supported on a bracket 6152 that is in turn supported on a plate 6154. A main support 6156 has tracks 6158 supporting plate 6154 for movement along the x-axis. Bracket 6152 can be pivotally mounted, for rotation of column 6120 about a vertical axis, and can be mounted on tracks on plate 6154, for motion of column 6120 along the y-axis. Handles 6160, 6162 can be provided on or at cassette 6134 to help in manually positioning the cassette.

Using the motions previously described, the operator can position cassette 6134 in the embodiments of FIGS. 69 and 70 in a similar variety of positions, for similar x-ray imaging procedures. While an x-ray source and a unit 6141 are not shown in FIGS. 69 and 70, it should be understood that they can be present and can be used as earlier described.

In each embodiment, electronic, electromechanical and/or mechanical brakes and clutches can be used to immobilize and release the connections between parts that can move relative to each other. Using such brakes and clutches can allow the operator to move cassette 6134 to the desired position manually with ease, and can securely fix cassette 6134 in a position for exposure. For example, the operator can trip switch 6138a to engage such clutch or clutches and/or brake or brakes to thereby allow motion, and can trip the switch to disengage such clutch(es) and/or brake(s) to thereby prevent motion. Such a clutch and/or brake arrangement can be used for one or more of the motions described above. Separate such arrangements can be used for different ones of the motions.

To facilitate the selection of a position for cassette 6134, various detents and indicators can be provided. For example, in the embodiment of FIGS. 61–68 a detent can be provided at bearing arrangement 6118 to releasably lock arm 6116 at each 90° position along the x-axis and y-axis (and/or at different angular positions). A similar detent can be provided at bearing 6132 for each 15° of a movement (or a different angular increment) of cassette 6134 over a 180° rotation.

Instead of manually moving cassette 6134 to the desired position as described above, respective electric or other motors can be used to drive some or all of the motions discussed above, under operator control. Alternatively, some or all of the motions can be automated, so that the operator can select one of several preset motion sequences, or can select vertical, horizontal and angular positions for cassette 6134, and computer controls can provide the necessary motor control commands. Particularly when movements are power-driven rather than manual, proximity and/or impact sensors can be used at the moving parts as a safety measure, generating stop-motion signals when a moving part gets too close to, or impacts with, an object or a patient.

Cassette 6134 can contain a flat panel detector that converts x-rays directly into electrical signals representing the x-ray image, using a detection layer containing selenium, silicon or lead oxide. Alternatively, cassette 6134 can contain a flat panel detector that uses a scintillating material layer on which the x-rays impinge to generate a light pattern and an array of devices responsive to the light pattern to generate electrical signals representing the x-ray image.

The disclosed system can be used for tomosynthesis motion, where the x-ray source and the cassette move relative to each other and the patient, or at least one of the source and cassette moves, either in a continuous motion or in a step-and-shoot manner. The image information acquired at each step (or each time increment) can be read out and the detector reset for an image at the next step (or time increment).

The disclosed system provides for a number of motions to accommodate a wide variety of imaging protocols: the x-ray detector image plane rotates between vertical and horizontal and can be locked at intermediate angles as well; the cassette moves horizontally along the length of the patient table as well as across the length of the patient table so that it can be positioned at either side of the table; the cassette moves vertically, the cassette can move between portrait and landscape orientations for non-square detector arrays and/or for desired orientation of the array grid even for square arrays; and the cassette can combine some or all of these motions in order to get to any desired position and orientation.

Safety can be enhanced by moving the cassette by hand, so the operator can observe all motion and ensure safety. Sensors can be provided for collision detection when any motion is motorized. When any motion is motorized, easy-stall motors can be used to enhance safety. In addition, when any motion is motorized, encoders can be provided to keep track of the positions of moving components, and the encoder outputs can be used for software tracking and collision avoidance control. When motions are motorized, preset motor controls can be stored in a computer and used to drive the cassette motion for specified imaging protocols or cassette positions so that the cassette can automatically move to a preset position for a given imaging protocol. Undesirable motion can be avoided or reduced by using clutch controls, hand brakes, counter-balancing, and/or detents that help identify and maintain a desired cassette position and orientation and help prevent grid oscillation and focusing grid misalignment.

What is claimed is:

1. A system for positioning a digital detector of x-rays for diagnostic protocols comprising:
   a detector that is free of a mechanical connection with an x-ray source and includes a digital flat panel x-ray detector arrangement and an anti-scatter grid;
   a floor-supported base; and
   an articulated structure supported on the base and supporting the detector and selectively moving the detector with at least four degrees of freedom relative to the base to position the detector for any one of a variety of standard diagnostic x-ray protocols.

2. A system as in claim 1 wherein said articulated structure selectively moves the detector with at least five degrees of freedom relative to the base.

3. A system as in claim 1 including a patient table and a releasable coupling arrangement for selectively coupling the detector to the patient table with respect to at least one of said degrees of freedom of detector motion.

4. A system as in claim 1 including detents limiting at least some of said degrees of freedom of detector motion to preferred intermediate positions.

5. A system as in claim 4 in which at least one of said detents comprises a step detent biasing the detector to selected positions.

6. A system as in claim 4 in which at least one of said detents is a locking detent selectively locking said detector to prevent motion thereof relative to at least one of said degrees of freedom.

7. A system as in claim 1 including motorized drivers for moving the detector in at least one of said degrees of freedom.

8. A system as in claim 1 including collision avoidance system coupled with said support structure to prevent collisions involving the structure and detector.

9. A system as in claim 8 in which the collision avoidance system comprises collision sensors and circuits responsive thereto to arrest motion that would result in a collision.

10. A system as in claim 1 including encoders coupled with the structure to provide digital information regarding movement thereof, and a computer coupled with the encoders to receive digital information therefrom and programmed to utilize the information to control said movement.

11. A system as in claim 10 including motorized drivers for moving the detector in at least some of said degrees of freedom, wherein said computer utilizes the digital information at least for positioning the detector at a selected position through controlling said motorized drivers.

12. A system as in claim 1 in which said degrees of freedom include rotation about two vertical and one horizontal axes.

13. A system as in claim 11 in which said degrees of freedom further include translation along a horizontal axis.

14. A system as in claim 13 in which said degrees of freedom further include translation along a vertical axis.

15. A system for positioning a digital detector of x-rays for diagnostic protocols using an x-ray source and selectively using a patient table, comprising:
   a detector that includes a digital flat panel x-ray detector arrangement and an anti-scatter grid; and
   a floor-mounted articulated structure supporting and selectively moving the detector in at least two translational and two rotational motions to position the detector for any one of a variety of standard diagnostic x-ray protocols;
   wherein said motions are selectively independent of motions of the x-ray source and patient table.

16. A system as in claim 15 wherein said articulated structure selectively moves the detector in at least two translational and three rotational motions.

17. A system as in claim 15 including a patient table and a releasable coupling arrangement for selectively coupling the detector to the patient table with respect to one of said translational motions.

18. A system as in claim 15 including at least one detent limiting at least one of said motions of the detector to selected positions.

19. A system as in claim 15 including collision avoidance system coupled with said support structure to prevent collisions involving the structure and detector.

20. A digital flat panel detector system for diagnostic x-ray procedures using an independently mounted x-ray source and selectively using a patient table, comprising:
   a digital flat panel x-ray detector;
   a support structure coupled with the detector to selectively move the detector independently of the x-ray source and patient table along a length of the table and rotate the detector to thereby position the detector for any one of a variety of standard diagnostic x-ray protocols for standing, sitting and recumbent patients;
   wherein said support structure comprises:
      a main support extending along the patient table length;
      a lower slide mounted on the main support to move thereon along the patient table length;
      a lower arm having a near end mounted on the lower slide for rotation about a lower arm axis; and
      an upwardly extending column mounted on a far end of the lower arm for rotation about a column axis;
   wherein moving the lower slide along the main support and rotating one or both of the lower arm and the column selectively moves the detector along and across the patient table length.

21. A system as in claim 20 wherein said support structure further comprises:
   an upper slide mounted on the column to move along the column; and
   an upper arm having a near end mounted on the upper slide for rotation about an upper arm axis;
   wherein selectively moving the upper slide along the column and rotating the upper arm moves the detector up and down and rotates the detector.

22. A system as in claim 21 wherein the detector is mounted at a far end of the upper arm for rotation about a detector axis transverse to the upper arm axis.

23. A system as in claim 21 including a patient table selectively moving at least up and down, and a coupling arrangement for selectively coupling up and down movement of the table to up and down movement of the detector.

24. A system as in claim 21 including releasable detents locking the lower and upper arms and the column at selected rotational positions.

25. A system as in claim 24 in which at least one of the detents comprises at least a sector of a cogwheel and a cam urged against the cogwheel to enter valleys between teeth of the cogwheel when a sufficient force causes relative rotation between the cogwheel and the cam but to remain in a valley and thereby maintain a selected relative position between the cogwheel and the cam in the absence of said force.

26. A system as in claim 24 including a lock selectively and releasably locking the cam in a cogwheel valley.

27. A system as in claim 21 including collision avoidance circuits coupled with at least the detector to prevent collision thereof with objects.

28. A system as in claim 21 including at least one collision sensor to warn of a likely collision between at least the detector and objects.

29. A system as in claim 28 including at least one collision avoiding circuit coupled with said collision sensor and responsive to a warning therefrom of a likely collision to prevent such collision avoidance lock selectively and releasably locking the cam in a cogwheel valley.

30. A system for positioning a digital detector of x-rays for diagnostic protocols comprising:
   a detector that is free of a mechanical connection with an x-ray source;
   a main support; and
   an articulated structure mounted on the main support and supporting and selectively moving the detector along and transversely to a length of the main support, up and down relative to the main support, and rotationally between different orientations to position the detector for any one of a variety of standard diagnostic x-ray protocols;
   wherein said articulated structure comprises:
      a lower slide mounted on the main support for movement along the length thereof;
      a lower arm having a proximal end mounted on the lower slide for rotation about a proximal upwardly extending axis; and
      a column mounted on a distal end of the lower arm for rotation about a distal upwardly extending axis;
   wherein moving the lower slide along the length of the main support and rotation about one or both of said upwardly extending axes moves the detector along either or both the length and across the length of the main support.

31. A system as in claim 30 wherein said articulated structure further comprises:
   an upper slide mounted on said column for movement along the column; and
   an upper arm having a proximal end mounted on the upper slide for rotation about an upper slide axis;
   wherein moving the upper slide along the column and rotating the upper arm about the upper slide axis moves the detector up and down and about a first detector rotational axis.

32. A system as in claim 31 wherein said upper arm had a distal end and said detector is mounted thereon for rotation about a second detector axis transverse to the first detector axis and to a plane of said detector.

33. A system for positioning a digital detector of x-rays for diagnostic protocols comprising:
- a digital flat panel x-ray detector;
- a low, stepped platform for a patient to climb and step on a portion thereof; and
- a detector support structure supporting and selectively moving the detector with at least two degrees of freedom to selectively position the detector in a horizontal orientation under a portion of the stepped platform for an x-ray image of a patient standing thereon, and in a vertical orientation alongside a portion of the platform for an x-ray image of a patient standing thereon;
- wherein said detector is free of a mechanical connection with an x-ray source used for imaging the patient.

34. A system as in claim 33 wherein said degrees of freedom include a rotation and a translation of the detector.

35. A system as in claim 33 including in which the support structure moves the detector selectively between a horizontal position under the portion of said portion of the low platform and a vertical orientation beside and at least partly above said portions.

36. A system as in claim 33 including a support rail for supporting a patient climbing and standing on said low platform.

37. A method comprising:
- moving a floor-supported digital flat panel detector relative to a ceiling-mounted x-ray source to position the detector at any one of a number of standard x-ray protocols for standing, sitting and recumbent patients;
- wherein said moving comprises moving the detector with at least five degrees of freedom relative to the x-ray source.

38. A method as in claim 37 including selectively and releasably locking the detector against movement.

39. A method as in claim 37 in which the moving step comprises motor-driving the detector for motion in at least one of the degrees of freedom.

40. A digital, flat panel x-ray detector cassette and a positioning arrangement for said cassette, comprising:
- a digital, flat panel, two-dimensional x-ray detector cassette;
- an upper arm supporting the cassette;
- a first slide to which the upper arm is pivotally secured for rotation about a laterally extending axis;
- an upwardly extending column to which the slide is secured for movement along the height of the column;
- a lower arm to which the column is secured;
- a second slide to which the lower arm is pivotally secured for rotation about an upwardly extending axis;
- a main support having a laterally extending track along which said second slide rides; and
- a patient table having a long dimension extending along the length of the track and positioned at a higher level than the track;
- said first slide and second slide moving linearly and said upper arm and lower arm moving pivotally to position the cassette relative to the table at any one of a number of positions relative to the table, including under the table at a horizontal or inclined orientation for an AP image of a patient lying on the table, to the side of the table in a vertical or inclined orientation for a lateral image of a patient lying on the table, adjacent to a head or foot of the table and in a horizontal or inclined orientation for an image of the head or lower extremities of a patient lying on the table and on the cassette, to the side of the table in a horizontal or inclined orientation for an image of an extremity supported on the cassette, spaced from the table and in a vertical or inclined orientation for an image of a standing patient, and spaced from the table and in a horizontal or inclined orientation for an image of a patient on a support other than the table.

41. A digital, flat panel x-ray detector cassette and a positioning arrangement for said cassette, comprising:
- a digital, flat panel, two-dimensional x-ray detector cassette;
- an upper arm supporting the cassette;
- a first slide to which the upper arm is secured for movement therewith;
- an upwardly extending column to which the slide is secured for movement along the length of the column;
- said cassette pivoting about a horizontal axis through pivoting motion of at least one of the cassette relative to the upper arm or the upper arm relative to the column;
- a lower support to which the column is secured, said lower support selectively moving the column along each of two directions transverse to each other and to the length of the column; and
- a main support supporting said lower support.

42. A cassette and positioning arrangement as in claim 41 including a pivoting arrangement between the arm and the column to provide for said pivoting of the cassette between different orientations.

43. A cassette and positioning arrangement as in claim 41 in which said lower support comprises a telescoping support extending to the side of said main support and moving the column along a generally horizontal axis.

44. A cassette and positioning arrangement as in claim 43 including mounting said telescoping support for pivotal motion about an upwardly extending axis.

45. A cassette and positioning arrangement as in claim 41 in which said lower support comprises a plate mounted for sliding movement on said main support along a first direction.

46. A cassette and positioning arrangement as in claim 44 in which said cassette is mounted for movement relative to the main support along a second direction transverse to said first direction.

47. A cassette and positioning arrangement as in claim 45 in which said mounting of the cassette for movement along the second direction comprises mounting said column for sliding movement on said plate along said second direction.

48. A cassette and positioning arrangement as in claim 41 including a patient table having a width extending along one of said transverse directions and a length extending along the other, said first slide moving along said column and said cassette pivoting and said column moving along said mutually transverse directions to position the cassette at a selected horizontal and vertical positions relative to the length and width of the table for an x-ray exposure.

49. A method of using a digital, flat panel x-ray detector cassette comprising:
- securing a digital, flat panel x-ray detector cassette to an upper arm;
- securing the upper arm to a first slide moving up and down in the direction of an upwardly extending column;
- said securing comprising pivotally securing at least one of the cassette to the upper arm and the upper arm to the first slide, for pivoting the cassette between a vertical and horizontal orientations;

supporting the column relative a patient table for selective movement along a length and along a width of the table to thereby move the cassette to a selected vertical alignment relative to the patient table;

moving the cassette to a selected height, selected vertical alignment with the patient table and selected angular orientation by one or more of said pivoting movement of the first slide along the column, and movement of the column along the length and along the width of the patient table to thereby position the cassette at a selected position; and locking the cassette at said selected position for an x-ray exposure.

50. A method as in claim 49 in which said column telescopes to move said first slide up or down.

* * * * *